US008329888B2

(12) United States Patent
Wengel et al.

(10) Patent No.: US 8,329,888 B2
(45) Date of Patent: Dec. 11, 2012

(54) SMALL INTERNALLY SEGMENTED INTERFERING RNA

(75) Inventors: Jesper Wengel, Odense (DK); Jorgen Kjems, Risskov (DK)

(73) Assignee: Santaris Pharma A/S, Horsholm (DK)

( * ) Notice: Subject to any disclaimer, the term of this patent is extended or adjusted under 35 U.S.C. 154(b) by 0 days.

(21) Appl. No.: 12/294,126

(22) PCT Filed: Mar. 23, 2007

(86) PCT No.: PCT/DK2007/000146
§ 371 (c)(1),
(2), (4) Date: Feb. 12, 2009

(87) PCT Pub. No.: WO2007/107162
PCT Pub. Date: Sep. 27, 2007

(65) Prior Publication Data
US 2009/0182136 A1  Jul. 16, 2009

(30) Foreign Application Priority Data

Mar. 23, 2006 (DK) .................................. 200600433
Sep. 28, 2006 (DK) .................................. 200601254

(51) Int. Cl.
C07H 21/04 (2006.01)
(52) U.S. Cl. ...................................................... 536/24.5
(58) Field of Classification Search .................. 536/24.5
See application file for complete search history.

(56) References Cited

U.S. PATENT DOCUMENTS

| | | | |
|---|---|---|---|
| 5,898,031 | A | 4/1999 | Crooke |
| 6,107,094 | A | 8/2000 | Crooke |
| 6,506,559 | B1 | 1/2003 | Fire |
| 7,056,704 | B2 | 6/2006 | Tuschl |
| 7,078,196 | B2 | 7/2006 | Tuschl |
| 7,432,250 | B2 | 10/2008 | Crooke |
| 7,589,190 | B2 | 9/2009 | Westergaard et al. |
| 2002/0068709 | A1 | 6/2002 | Orum et al. |
| 2003/0108923 | A1 | 6/2003 | Tuschl et al. |
| 2004/0014956 | A1* | 1/2004 | Woolf et al. .................. 536/23.1 |
| 2004/0053875 | A1 | 3/2004 | Kreutzer et al. |
| 2004/0180351 | A1 | 9/2004 | Giese et al. |
| 2005/0234007 | A1 | 10/2005 | Tuschl et al. |
| 2005/0261212 | A1 | 11/2005 | McSwiggen |
| 2007/0191294 | A1 | 8/2007 | Elmen |
| 2008/0249039 | A1 | 10/2008 | Elmen |
| 2009/0176977 | A1 | 7/2009 | Elmen |

FOREIGN PATENT DOCUMENTS

| | | |
|---|---|---|
| AU | 2006311912 | 5/2007 |
| CA | 2459532 | 2/2003 |
| EP | 0928290 | 3/2005 |
| EP | 1214945 | 6/2005 |
| EP | 1407044 | 9/2007 |
| EP | 1550719 | 12/2008 |
| WO | WO 99/14226 | 3/1999 |
| WO | WO 00/56746 | 9/2000 |
| WO | WO 00/56748 | 9/2000 |
| WO | WO00/66604 | 11/2000 |
| WO | WO 01/25248 | 4/2001 |
| WO | WO 02/28875 | 4/2002 |
| WO | WO02/44321 | 6/2002 |
| WO | WO 03/006475 | 1/2003 |
| WO | WO03/070918 | 8/2003 |
| WO | WO 03/095467 | 11/2003 |
| WO | WO2004/041889 | 5/2004 |
| WO | WO 2004/042046 | 5/2004 |
| WO | WO2004/083430 | 9/2004 |
| WO | WO 2004/099387 | 11/2004 |
| WO | WO2005/073378 | 8/2005 |
| WO | WO 2006/050734 | 5/2006 |
| WO | WO2007/056153 | 5/2007 |
| WO | WO2007/085485 | 8/2007 |
| WO | WO2008/049078 | 4/2008 |

OTHER PUBLICATIONS

Yu et al. PNAS 2002, 99, 6047-6052.*
Alexopoulou et al., (2001) Nature, 413:732-738.
Amarzguioui et al., ( 2003) Nucl. Acid Res., 31:589-595.
Bosher and Labouesse, (2000) Nature Cell Biology, 2:E31-E36.
Boutla et al., (2001) Curr. Biol., 11:1776-1780.
Braasch et al., (2003) Biochemistry, 41:4503-4510.
Braasch et al., (2003) RNA interference in mammalian cells by chemically-modified RNA, Biochemistry, 42:7967-7975.
Elbashir et al., (2001) Nature, 411: 494-498.
Elbashir et al., (2001) "Functional anatomy of siRNAs for mediating efficient RNAi in *Drosophila melanogaster* embryo lysate", The EMBO Journal, 20: 6877-6888.
Elbashir et al., (2001) Gen. Dev., 15:188-200.
Fire et al., (1998) Nature 391:806-811.
Fire, (1999) Trends in Genetics, 15:358-363.
Frieden et al., (2003) "Expanding the design horizon of antisense oligonucleotides with alpha-L-LNA," Nucl. Acids, Res. 31(21):6365-6372.
Hamada et al., (2002) Antisense and Nucl. Acid Drug Dev., 12:301-309.
Hammond et al., (2000) Nature, 404:293-296.
Hayakawa, (2001) Bull. Chem. Soc. Jpn. 74:01547-1565.
Hohjoh, (2002) FEBS Lett., 521:195-199.
Holen et al., (2002) Nar, 30:1757-1766.
Kumar et al., (1998) The first analogues of LNA . . . , Bioorg. & Medicin. Chem. Letters, 8:2219-2222.
Martinez et al., (2002) Cell, 110:563-574.
McManus and Sharp, (2002) Nature Reviews Genetics, 3:737-747.
Nykanen et al., (2001) Cell, 107:309-321.
Parrish et al., (2000) "Functional anatonmy of dsRNA trigger: differential requirement for the two trigger strands in RNA interference", Molecular Cell, 6:1077-1087.
Samuel, (2001) Clin. Micro. Rev., 14:778-809.
Stark et al., (1998) Annu. Rev. Biochem., 67:227-264.
Thompson, (2002) DDT, 7:912-917.
Wargelius et al., (1999) Biochem. Biophys. Res. Corn., 263:156-161.
Wianny and Zernicka-Goetz, (2000) Nature Cell Biology, 2:70-75.
Zamore et al., (2000) Cell, 101:25-33.
Birmingham et al., "'3' UTR seed matches, but not overall identity, are associated with RNAi off-targets" (2006) Nature Methods, vol. 3, No. 3, pp. 199-204.

(Continued)

*Primary Examiner* — Brian Whiteman
(74) *Attorney, Agent, or Firm* — Fish & Richardson P.C.

(57) ABSTRACT

The present invention is directed to pharmaceutical and therapeutic compositions which comprise RNA complexes comprising an antisense strand and a discontinued passenger strand capable of regulating gene expression. The use of a discontinued passenger strand reduces off target effects of the RNA complexes and also has other advantages.

10 Claims, 27 Drawing Sheets

OTHER PUBLICATIONS

Bramsen et al., "Improved silencing properties using small internally segmented interfering RNAs". Nucleic Acids Research vol. 35, No. 17: pp. 5886-5897 (2007).

Elmen et al., "Locked nucleic acid (LNA) mediated improvements in siRNA stability and functionality" (2005) Nucleic Acids Research, vol. 33, No. 1:pp. 439-447.

Jackson et al., "Expression profiling reveals off-target gene regulation by RNAi" (2003) Nature Biotechnology, vol. 21, No. 6, pp. 635-637.

Jackson et al., "Widespread siRNA "off-target" transcript silencing mediated by seed region sequence complementarity" (2006) RNA Journal, vol. 12, pp. 1179-1187.

Leuschner et al. "Cleavage of the siRNA passenger strand during RISC assembly in human cells". EMBO Reports vol. 7, No. 3:pp. 314-320 (2006).

Maiti et al., "QIP, a putative exonuclease, interacts with the Neurospora Argonaute protein and facilitates conversion of duplex siRNA into single strands". Genes & Development 21:590-600 (2007).

Matranga et al., "Passenger-Strand Cleavage Facilitates Assembly of siRNA into Ago2-Containing RNAi Enzyme Complexes" Cell vol. 123, pp. 607-620 (2005).

Petersen and Wengel, "LNA: a versatile tool fro therapeutics and genomics" (2003) Trends in Biotechnology, vol. 21, No. 2:pp. 74-81.

Schwarz et al., "Asymmetry in the Assembly of the RNAi Enzyme Complex" (2003) Cell, vol. 115:pp. 199-208.

Soutschek et al., "Therapeutic silencing of an endogenous gene by systemic administration of modified siRNAs" (2004) Nature, vol. 432 (11):pp. 173-178.

Imanishi et al., "Synthesis and Property of Novel Conformationally Constrained Nucleoside and Oligonucleotide Analogs," The Sixteenth International Congress of Heterocyclic Chemistry 1015:PO1-101 (1997).

Singh et al., "LNA (locked nucleic acids): synthesis and high-affinity nucleic acid recognition," Chem. Commun, 1998:455-456.

Paushkin et al., "The SMN complex, an assemblyosome of ribonucleoproteins," Curr. Opin. in Cell Biol., 14:305-312 (2002).

\* cited by examiner

Figure 1A
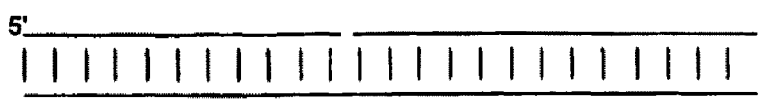
Figure 1B
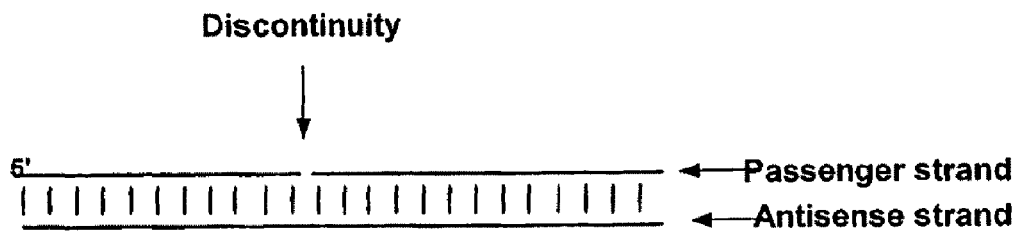
Fig. 1

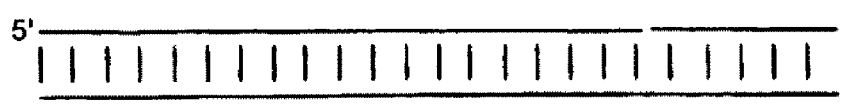
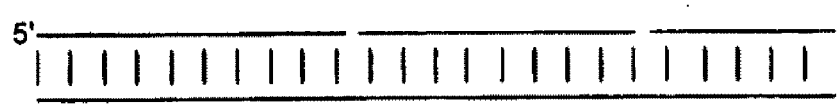
Fig. 3

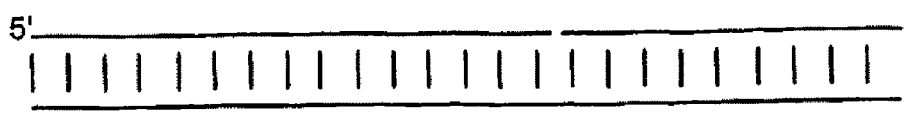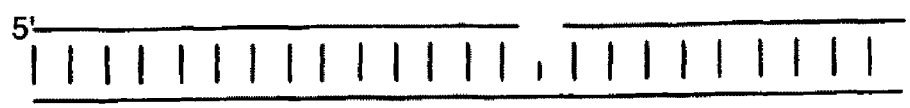
Fig. 4

A.
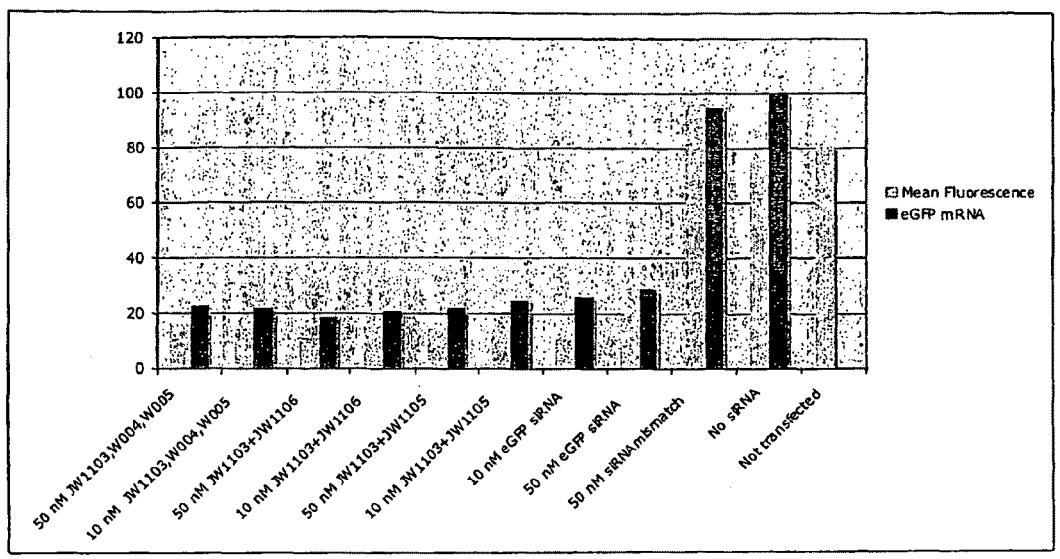
B.
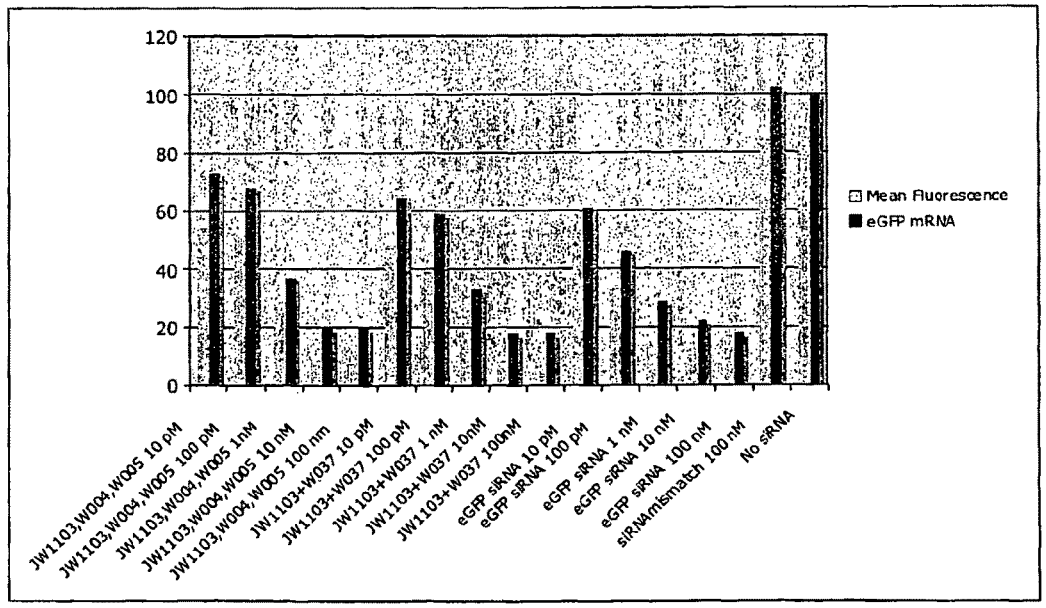
Fig. 11

□ sense target
■ off-target

A
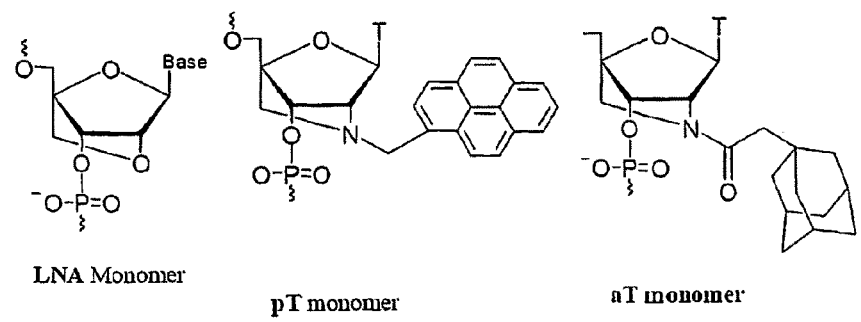
LNA Monomer    pT monomer    aT monomer
B
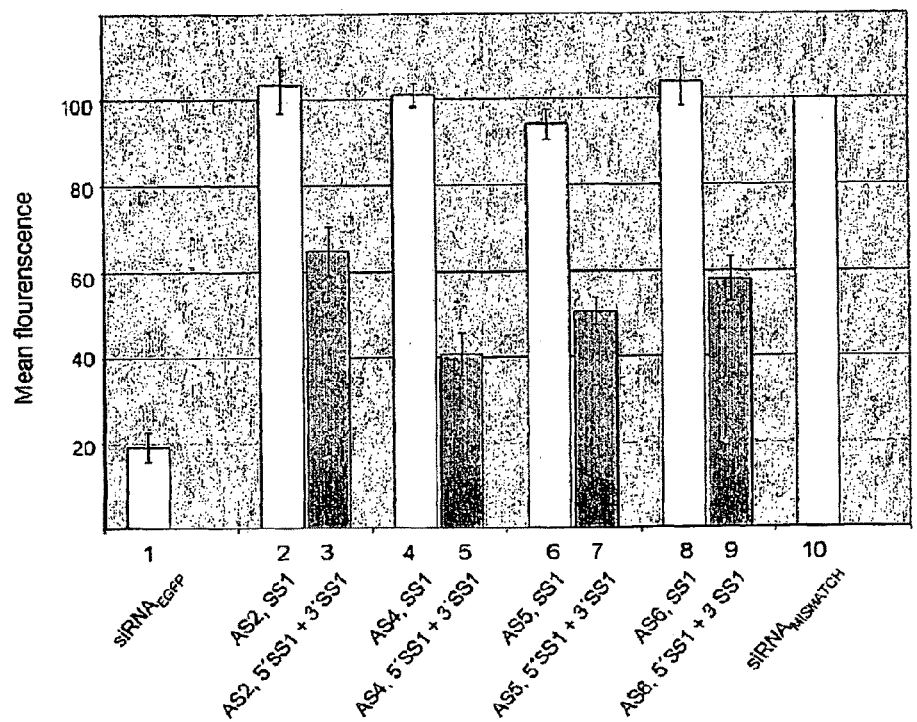
Fig.18 A & B

LNA-modified siRNA – LNA/DNA mixmer as sense strand

| Sense / Antisense (50 nM) | Monomers | Mean GFP | EGFP mRNA |
|---|---|---|---|
| GACGUAAACGGCCACAAGUUCU-3'<br>3'-UCGCUGCAUUUGCCGGUGUUCA | RNA<br>RNA | 13% | 16% |
| dddddddddddddddddddLLd-3'<br>3'-rLLrrrrrrrrrrrrrrrrrrrr | DNA / LNA<br>RNA / LNA | 60% | 38% |
| ddLddLddLddLddLddLdLLd-3'<br>3'-rLLrrrrrrrrrrrrrrrrrrrr | DNA / LNA<br>RNA / LNA | 35% | 21% |

- LNA/DNA mixmer sense strand mimics RNA

Fig.19

LNA-modified and unmodified sisiRNA constructs in cell culture

| Sense / Antisense (50 nM) | Monomers | Mean GFP | EGFP mRNA |
|---|---|---|---|
| GACGUAAACGGCCACAAGUUCU-3'<br>3'-UCGCUGCAUUUGCCGGUGUUCA | RNA<br>RNA | 13% | 16% |
| rrLrrrrrLr<br>3'-rLLrrrrrrrrrrrrrrrrrrrr | RNA / LNA<br>RNA / LNA | 10% | 18% |
| rrrrrrrrrr<br>3'-rLLrrrrrrrrrrrrrrrrrrrr | RNA / RNA<br>RNA / LNA | 35% | 45% |
| rrLrrrrrLrr<br>3'-rLLrrrrrrrrrrrrrrrrrrrr | RNA / LNA<br>RNA / LNA | 12% | 16% |

Fig.20

2'-F-DNA- and 2'-O-Me-RNA-modified sisiRNA

| Sense / Antisense (50 nM) | Monomers | Mean GFP | EGFP mRNA |
|---|---|---|---|
| GACGUAAACGGCCACAAGUUCU-3' | RNA | 13% | 16% |
| 3'-UCGCUGCAUUUGCCGGUGUUCA | RNA | | |
| rrFrrrrrFr | 2'-F / RNA | 44% | |
| 3'-rLLrrrrrrrrrrrrrrrrrrrr | RNA / LNA | | |
| rrMrrrrrMr | 2'-O-Me / RNA | 46% | |
| 3'-rLLrrrrrrrrrrrrrrrrrrrr | RNA / LNA | | |

F = 2'-F-DNA    M = 2'-O-Me-RNA

Fig.21 sisiRNA with functionalised sense strands

| Sense / Antisense (50 nM) | Monomers | Mean GFP | EGFP mRNA |
|---|---|---|---|
| GACGUAAACGGCCACAAGUUCU-3' | RNA | 13% | 16% |
| 3'-UCGCUGCAUUUGCCGGUGUUCA | RNA | | |
| rrrrXrrrrrrrrrrrrrrXLr-3' | RNA / LNA | 46% | |
| 3'-rLLrrrrrrrrrrrrrrrrrrrr | RNA / LNA | | |
| rrLrXrrrLr     X | RNA / LNA | 18% | |
| 3'-rLLrrrrrrrrrrrrrrrrrrrr | RNA / LNA | | |

X = 2'-adamantyl-amino-LNA

Fig.22 sisiRNA with LNA-modified antisense strand

| Sense / Antisense (50 nM) | Monomers | Mean GFP | EGFP mRNA |
|---|---|---|---|
| GACGUAAACGGCCACAAGUUCU-3'<br>3'-UCGCUGCAUUUGCCGGUGUUCA | RNA<br>RNA | 13% | 16% |
| rrLrrrrrLrrrLrLrrrrLLr-3'<br>3'-rLLrrrrrrrrrrrrrrrrrr | RNA / LNA<br>RNA / LNA | 9% | 18% |
| rrLrrrrrLrrrLrLrrrrLLr-3'<br>3'-rLLrrrrrLrrLrrrrLrrLrr | RNA / LNA<br>RNA / LNA | 98% | 96% |
| rrLrrrrrLr<br>3'-rLLrrrrrLrrLrrrrLrrLrr | RNA / LNA<br>RNA / LNA | 18% | 22% |

Fig.23 sisiRNA with fully 2'-F/2'-OMe-modified antisense strand

| Sense / Antisense (50 nM) | Monomers | Mean GFP | EGFP mRNA |
|---|---|---|---|
| GACGUAAACGGCCACAAGUUCU-3'<br>3'-UCGCUGCAUUUGCCGGUGUUCA | RNA<br>RNA | 13% | 16% |
| rrLrrrrrLrrrLrLrrrrLLr-3'<br>3'- MFMFMFMFMFMFMFMFMFMFM | RNA / LNA<br>2'-F / 2'-O-Me | 78% | 68% |
| rrLrrrrrLr<br>3'- MFMFMFMFMFMFMFMFMFMFM | RNA / LNA<br>2'-F / 2'-O-Me | 29% | 35% |

F = 2'-F-DNA   M = 2'-O-Me-RNA

Fig.24 sisiRNA with functionalised antisense strand

| Sense / Antisense (50 nM) | Monomers | Mean GFP | EGFP mRNA |
|---|---|---|---|
| GACGUAAACGGCCACAAGUUCU-3' | RNA | 13% | 16% |
| 3'-UCGCUGCAUUUGCCGGUGUUCA | RNA | | |
| rrLrrrrrLrrrLrLrrrrLLr-3' | RNA / LNA | 95% | 100% |
| 3'-rLLrXrrrrrrrrrrrrrrrrr | RNA / LNA | | |
| rrLrrrrrLr | RNA / LNA | 39% | 50% |
| 3'-rLLrXrrrrrrrrrrrrrrrrr | RNA / LNA | | |

X = 2'-adamantyl-amino-LNA

Fig. 25

SMALL INTERNALLY SEGMENTED INTERFERING RNA

FIELD OF THE INVENTION

The invention belongs to the field of in vivo down-regulation of gene expression using modified siRNA complexes. By way of example, the RNA complexes according to the invention may be used in pharmaceutical compositions or for in vivo analysis of gene function.

BACKGROUND

The field of RNA interference has attracted massive attention in recent years, as it can provide specific gene knockouts. Obviously, this is very important in basic research when studying genetic and biochemical pathways or the function of individual genes and gene products. In line with this, RNA interference has become a very important tool for target validation in the pharmaceutical industry. Moreover, substantial investments are made with the goal of developing RNA complexes capable of mediating RNA interference that can be used as drugs.

The attractiveness of RNAi for use in therapy lies in its sensitivity and sequence specificity. However, concerns have arisen concerning sequence specificity, e.g. because the wrong strand of the RNA complex may direct the response to the wrong target nucleic acids. Moreover, RNA complexes of a certain size induce a non-specific interferon dependent response, which is also undesirable.

Patent application US2003/0108923 describes RNA complexes capable of mediating RNAi comprising an antisense strand and a passenger strand, wherein the strands are 21-23 nucleotides in length. It is suggested that the RNA complexes are used for therapeutic applications.

Similarly, patent application US2005/0234007 describes RNA complexes capable of mediating RNAi comprising an antisense strand and a passenger strand, wherein the complex comprises 3'-overhangs. It is suggested that the RNA complexes are used for therapeutic applications.

WO2005/073378 describes RNAi complexes capable of mediating RNAi comprising an antisense strand and a passenger strand. The RNA complexes described in the specification comprise LNA residues and it is stated that incorporation of LNA residues near the 5' end of one of the strands can control which strand is incorporated in the RISC complex, because the strand that forms the weakest base pair at its 5-end is incorporated into the RISC complex. Matranga et al. (2005, Cell Vol 123, pp 607-620), discloses that the maturation of the active RISC complex requires the cleavage of the passenger strand by Ago-2. The cleavage of the passenger strand occurs between nucleotides 9 and 10 during RISC assembly.

Leuschner et al., (EMBO Reports, published online 20 Jan. 2006) discloses RNAi-induced silencing complexes which have a discontinuous passenger strand. Leuschner et al also used 2'-O methyl ribose units at position 9 of the passenger strand (5' to 3'). The RNAi complexes are tested in an in vitro cell extract experiment. The use of discontinuous passenger strands was found to result in efficient target RNA cleavage, as did RNAi complexes where the 2'-O methyl ribose unit was located at the passenger site cleavage site (9). However, when the 2'-O methyl ribose unit was located further upstream of the cleavage site there was a reduction in target RNA cleavage.

Neither Leuschner et al nor Matranga et al. disclose or suggest that RNAi-induced silencing complexes which have a discontinuous passenger strand are preferable RNAi complexes for use in therapy.

The use of synthetic siRNAs in vivo is currently hampered by lack of efficient means of siRNA delivery, low biostabililiy in biological fluids and low specificity of action due to inherent gene off-target effects associated with the microRNA-like behaviour of all investigated siRNAs (Jackson, A. L et al., (2003) Nat Biotechnol, 21, 635-637; Birmingham, A et al., J. et al. (2006) Nat Methods, 3, 199-204; Jackson, A. L et al., (2006) Rna, 12, 1179-1187.). Several attempts to reduce off-target effects through chemical modification of synthetic siRNA have been made (Jackson, A. L et al., (2003) Nat Biotechnol, 21, 635-637; Birmingham, A et al., J. et al. (2006) Nat Methods, 3, 199-204; Jackson, A. L et al., (2006) RNA, 12, 1179-1187; Elmen, J et al. (2005) Nucleic Acids Res, 33, 439-447; Jackson, A. L et al. (2006) RNA). Since both sense- and antisense-strands can contribute to off-target effects (Jackson, A. L et al., (2003) Nat Biotechnol, 21, 635-637), minimizing sense strand incorporation into activated RISC should significantly increase targeting specificity and thereby reduce sense strand off-targeting. It is well established that the siRNA strand with the thermodynamically least stable 5' end is preferentially utilized as antisense strand in activated RISC (Schwarz, D. S et al., (2003) Cell, 115, 199-208.).

Double stranded RNA complexes can mediate various modifications of target nucleic acids in the cell. In this process, the antisense strand of the complex acts as a guide, as the antisense strand can hybridise to target nucleic acids that have stretches of sequence complementarity to the antisense strand.

Before targeting a target nucleic acid, the antisense strand is often incorporated into an RNA guided protein complex (RGPC), which can act upon the target nucleic acid. One example of a RNA guided protein complex is the RNA Induced Silencing Complex (RISC). It is believed that other such RGPCs exist and that the RNA complexes of the present invention will also be of advantage, when used with these other RGPCs.

However, when used in vivo as a therapeutic agent or gene discovery tool, the silencing complex such as RISC is unable to distinguish which of the two strands of a siRNA silencing complex is the intended antisense strand, and which is the passenger or guide strand. The loading of a passenger strand into the silencing complex may well result in unintentional silencing of off-targets, i.e. unintentional targets which have sufficiently high complementarity to the passenger strand. The risk of such off-target events is therefore a major issue when considering the development of both therapeutic and gene discovery agents based upon siRNA complexes.

The selection of the strand for insertion into the RISC complex depends, in one aspect, upon the strength of the hydrogen bonding between the 5' of each strand. By designing siRNAs to ensure the 5' base of the passenger strand is a G or C and the 5' base of the antisense strand is a A or T, it is possible to preferentially bias the selection of the antisense strand for incorporation into the RISC silencing complex. However this does not prevent loading of the passenger strand into the RISC silencing complex.

The incorporation of affinity enhancing nucleotide analogues at the 5' end of the passenger strand can further reduce the proportion of passenger strand loading into the RISC silencing complex. Accordingly, selective thermodynamic stabilization of sense strand 5 ends by Incorporation of locked nucleic acids (LNA) has been shown to reduce unwarranted gene silencing by the sense-strand (Elmen, J et al. (2005)

Nucleic Acids Res, 33, 439-447; Petersen, M. and Wengel, J. (2003) Trends Biotechnol, 21, 74-81.).

Incorporation of nucleotide analogues at positions 10 and 12 (from the 5' end) of the passenger strand can prevent the RISC cleavage event as these residues are thought to align to the catalytic centre of the RISC complex. However, the incorporation of affinity enhancing nucleotide analogues reduces the efficacy of the modified siRNA complexes, possibly by increasing the resistance of the siRNA to the action of the RISC complex helicase. The incorporation of high loads of affinity enhancing nucleotide analogues has therefore been limited due to the negative effect such analogues have on silencing efficacy.

The introduction of dsRNA complexes into a mammalian cell can result in induction of the interferon response, which leads to cell death. Whilst it has previously been considered that the interferon effect has been limited to the presence of longer dsRNA molecules, such as those associated with viral infection and replication, it is now known that short siRNA like entities can also induce the interferon response. It has been suggested that the introduction of nucleotide analogues within the siRNA can be used to limit or even prevent the induction of the interference effect. Therefore, it has been considered desirable to introduce nucleotide analogues into siRNA like complexes for use in in vivo applications.

Incorporation of nuclease resistant nucleotide analogues is thought to be beneficial to protect the 3' overlapping ends of smRNAs. As the 3' overlaps do not contribute to the strength of the hybridisation between the sense and passenger strand these do not have a negative effect on the action of the RISC complex helicase.

There is therefore a critical problem which limits the success and efficacy of siRNA in in vivo applications such as therapeutic and gene discovery applications, how to prevent off target effects due to unintentional silencing caused by the passenger strand, whilst avoiding the undesirable inhibitor effects associated with the use of affinity enhancing nucleotide analogues.

BRIEF DESCRIPTION OF THE FIGURES

FIGS. 1-6 illustrate examples of different architectures of the RNA complexes of the invention. It will be apparent for the skilled man that the various features illustrated can be combined, e.g. a particular pattern of overhangs may be combined with one or several discontinuities at particular positions that may or may not be linked. Thus, the figures should be interpreted as non-limiting, such that e.g. the nature and position of the discontinuity can be changed and additional features can be added.

FIG. 1 illustrates the basic structural features of RNA complexes of the invention. A: Shows the core double-stranded region of the RNA complexes of the invention. B: Indicates the antisense strand (the lower strand) and the discontinued passenger strand (the upper strand). The discontinuity of the passenger strand is also indicated. Note that the shown discontinuity is an exemplary nick, and that other kinds of discontinuities are described in the specification.

FIG. 2 illustrates various combinations of overhangs and blunt ends.

FIG. 3 illustrates that one or more discontinuities may be used in the passenger strand.

FIG. 4 illustrates that the size of the discontinuities may be varied.

FIG. 5 illustrates that one or more linkers may be used to connect the antisense strand with the passenger strand and/or to connect a first and a second RNA molecule of the passenger strand.

FIG. 6 illustrates that the position of the discontinuity may be varied.

FIGS. 7-12 shows experimental data obtained as described in the examples section.

FIG. 7: Serum stability of siRNA, siLNA and sisiRNA. Duplexes of siRNA (eGFPsiRNA), siLNA (JW1103, W1106) and sisiRNA (JW1103, W004, W005) were incubated for the indicated time at 20 µM concentration at 37° C. in 10%-foetal bovine serum, and were then subjected to non-denaturing polyacrylamide gel electrophoresis and visualised by SYBR gold staining. A straight line is included just above the expected migration of uncleaved oligonucleotides.

FIG. 8: Fluorescence microscopy analysis of eGFP expression. Testing the knock down of sisiRNA and related constructs. HT1089 cells where treated with 50 nM of the indicated combinations of RNA/LNA and analysed 48 hours after for eGFP expression. The EGFP expression was assessed both at the RNA and protein level. (A) Fluorescence microscopy analysis of EGFP expression in cells. Cells where treated with 50 nM of the indicated combinations of RNA/LNA oligos and analyzed 48 hours after for EGFP expression. (C) Northern blot showing EGFP mRNA expression after 48 hours (lanes 1-6) and 120 hours (lanes 7-12).

FIG. 9: Analysis of eGFP mRNA and protein expression in sisiRNA treated cells. A. Western blot showing the expression of eGFP protein in cells treated with 50 nM of the indicated combinations of oligonucleotides. The filter was reprobed with an antibody specific to hnRNPC1 protein as a loading control. B Northern blot investigating eGFP mRNA expression after 48 hours (lanes 1-6) and 120 hours (lanes 7-12). The filter was reprobed for hnRNP A1 expression as a loading control. The RNA samples was analysed in duplicates under the same conditions.

FIG. 10: Analysis of eGFP expression over an extended period of time. 10A: Western blot showing the expression of eGFP at 48, 120 and 180 h after transfection using the indicated combinations of oligonucleotides. The hnRNP C1 protein was included as internal control. The filter was reprobed for hnRNP A1 expression as a loading control (lanes 1-12). The RNA samples were analyzed in duplicates under the same conditions. 10B: Flow analysis of the mean fluorescence of 50.000 cells (based on three experiments).

FIG. 11: Comparison of the knock down efficiency between sisiRNA and other siLNAs and siRNAs targeting the same sequence. A. Knock down efficiency between sisiRNA, siLNA and siRNA. B. Analysing the concentration dependence on knock down efficiency. The protein quantification is based on the mean eGFP expression of approximately 50.000 cells measured by flowcytometry and the eGFP mRNA was quantified from Northern blots similar to the one shown in FIG. 3. siRNA mismatch represent an siRNA that contains 4 mismatches to the eGFP target (see sequence below).

FIG. 12: Optimisation the sisiRNA design. eGFP knock down efficiency using different variants of sisiRNA designs with a discontinuous passenger strand. The protein quantification is based on the mean eGFP measured by flowcytometry. The siRNA mismatch represents a siRNA that contains 4 mismatches to the eGFP target (see sequence below). A comparison between column 3 and 4 illustrates that the nick position can be moved from position 10 to 11 without any detrimental effect; Column 7 shows that the passenger strand can be just RNA, but passenger strands which include nucleotide analogues such as LNA are better; the comparison between column 6 and 8 show that sisiRNA can accept an LNA-modified antisense strand (within the duplex region) whereas this eliminates the activity in the corresponding normal siRNA construct containing a similarly LNA-modified antisense strand.

FIG. 19 shows a comparison between siRNA complexes which comprise a passenger strand which comprises of only DNA and LNA units, either in blocks, where the second and third most 3' residues of the passenger strand are LNA within a DNA passenger strand or an alternating pattern of two DNA and a single LNA unit. It shows that non RNA passenger strands can be functional within the context of a siRNA silencing complex.

FIG. 20 shows a comparison of LNA-modified and unmodified sisiRNA constructs in cell culture and illustrates that the introduction of LNA into a discontinuous passenger strand enhances the silencing effect, and that shifting the nick from position 10 to position 11 of the passenger strand has little effect in the efficacy of silencing. The expression levels shown for Mean GFP and EGFP mRNA are estimated values based on the experiments performed.

FIG. 21 shows a comparison of 2'-F-DNA and 2'-O-Me-RNA modified sisiRNAs and illustrates that passenger strands which comprise such modifications shows some level of silencing but this is not as effective as was seen with LNA (FIG. 20). The expression levels shown for Mean GFP and EGFP mRNA are estimated values based on the experiments performed.

FIG. 22 shows a comparison of discontinuous and continuous LNA modified passenger strands of sisiRNAs and illustrates that the more functionalised passenger strands are allowed with LNA modified sisiRNA as compared to siLNA (LNA modified siRNA). The expression levels shown for Mean GFP and EGFP mRNA are estimated values based on the experiments performed.

FIG. 23 shows a comparison of sisiRNA with LNA modified antisense strands which clearly illustrates that the presence of a discontinuous passenger strand overcomes the inhibitory effect of heavy modification of antisense strands, particularly in the areas which form the hybrid with the passenger strand. The expression levels shown for Mean GFP and EGFP mRNA are estimated values based on the experiments performed.

FIG. 24 shows a comparison of sisiRNA with 2'-F/2'-OMe LNA modified antisense strands which illustrates that the use of a discontinuous passenger strand allows for the use of a completely modified antisense strand. The expression levels shown for Mean GFP and EGFP mRNA are estimated values based on the experiments performed.

FIG. 25 shows that the use of a discontinuous passenger strand also allows for the use of 2'adamantyl-amino LNA within the antisense strand. The expression levels shown for mean GFP and EGFP mRNA are estimated values based on the experiments performed.

SUMMARY OF THE INVENTION

Figure 2:
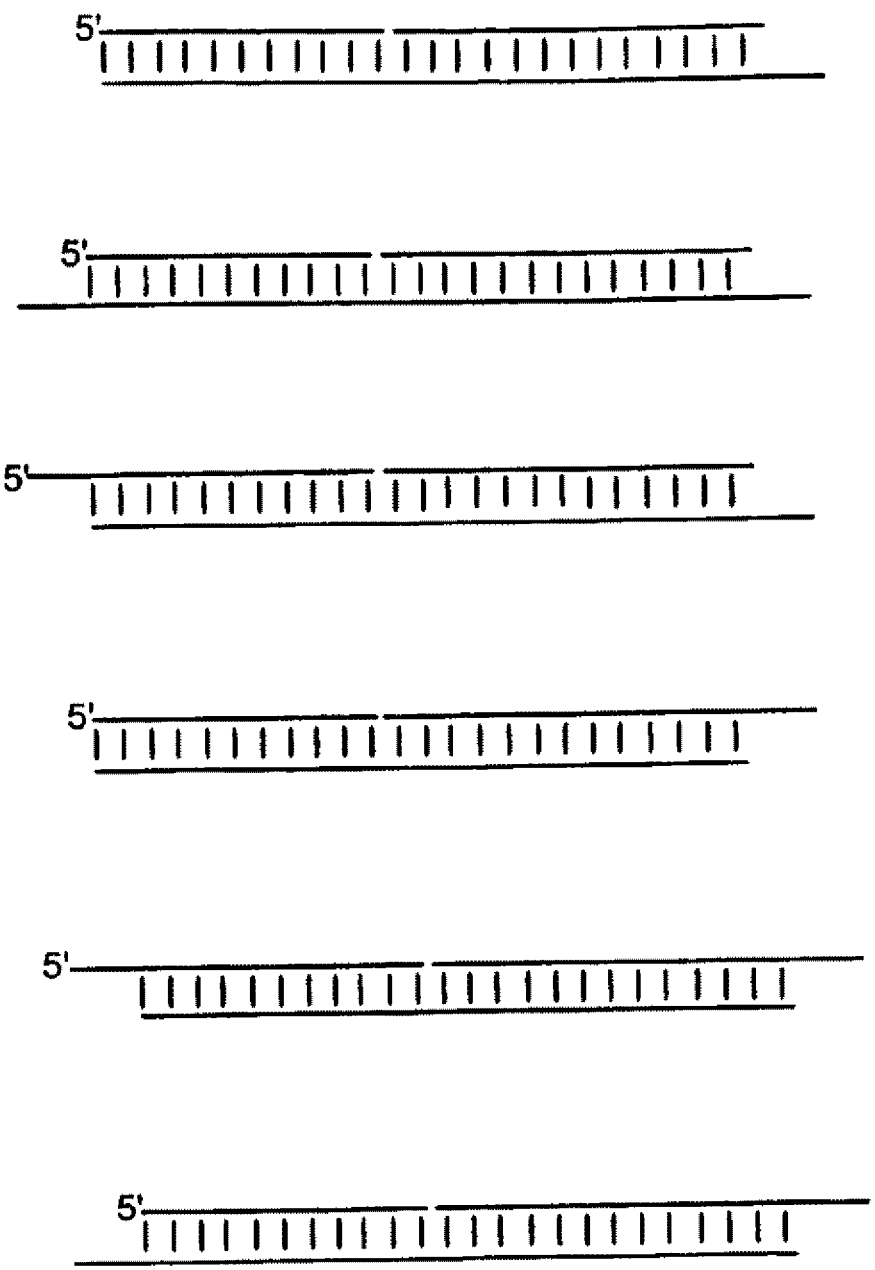

The present invention provides a radically different design of therapeutic silencing complex characterized by an intact antisense strand complemented with a discontinuous sense (passenger) strand, typically comprising of two nucleotides sense strands each being of between 9-13 nucleobases in length. We show that only the antisense strand of this construct is capable of gene silencing thereby significantly increasing targeting specificity.

Furthermore, whilst the use of a discontinuous passenger strand may, in some cases, lead to a reduced stability of the silencing complex due to a possible enhanced probability of disassociation of the passenger and antisense strands prior to interaction with the RISC complex, we have surprisingly found that the use of affinity enhancing nucleotide analogues within the duplex formed between a discontinuous passenger strand and the antisense strand can be used to effectively stabilise the duplex in vivo, without unduly effecting the functionality of the silencing complex in terms of silencing of the intended target of the antisense strand. The invention therefore provides both a solution to the avoidance of passenger strand mediated off target effects, but also, quite remarkably a solution which allows the introduction of a high load of nucleotide analogues within the duplex of the silencing complex, providing considerable benefit in terms of stability of the duplex in vivo, resistance to nuclease attack, and avoidance of the interferon response.

A duplex between two RNA molecules typically exists in an A-form conformation, where as a duplex between two DNA molecules typically exits in a B-form conformation. A duplex between a DNA and RNA molecule typically exists in a intermediate conformation (A/B form). The use of nucleotide analogues, such as beta-D-oxy LNA can be used to promote a more A form like conformation.

As recruitment by the RISC complex is thought to be dependent upon the specific structural conformation of the siRNA, it is preferable that the nucleotide analogues used within the duplex either promote or do not disrupt the formation of the A-form conformation of the double stranded RNA complex. Standard NMR or CD methods may be used to determine whether the duplex forms an A-form conformation.

However, we have also determined that the use of nucleotide analogues which promote the B-form structure can also be effective, such as the alpha-L isomer of LNA, which in the context of the present invention is a preferred nucleotide analogue monomer unit, such as for incorporation into the passenger strand. We therefore believe that it is not essential that the passenger strand forms a A-form conformation with the antisense strand, but it may form an intermediate A/B-form conformation, of even, in one embodiment a B-form conformation.

In one embodiment the passenger strand consists of oligonucleotides which comprise both LNA and 2'OMe or 2' fluoro nucleotide analogues, as referred to herein. In such an embodiment, it is envisaged that one construct may comprise passenger strands which comprise of alternating LNA and 2'OMe nucleotide analogue residues, or alternative LNA and 2'fluoro, or combinations of LNA and 2'OMe/2'fluor nucleotide analogues.

Moreover, incorporation of nucleotide analogues, such as LNA monomer units into the disrupted sense strand significantly increases serum stability and prolongs target knock down. Interestingly, the sisiRNA design can functionally accommodate heavily modified antisense strands that are non-functional as standard siRNAs. This is critically important for siRNA application in vivo, particularly for use as a therapeutic agent or as a functional genomics tool.

The present invention provides RNA complexes with a discontinued passenger strand to be used in relation to RNA-guided gene regulation, in particular RNA interference. Thus, it is an object of the present invention to provide RNA complexes, which have reduced off target effects as compared to the RNA complexes typically used. Another object is to provide RNA complexes which a reduced interferon response. Still another object is to provide RNA complexes with improved properties with regard to synthesis and feasibility of chemical modifications. The RNA complexes may be in the form of a pharmaceutical (therapeutic) composition which comprise the RNA complex and a pharmaceutically acceptable diluent, carrier, or adjuvant.

DETAILED DESCRIPTION OF THE INVENTION

In the present invention we have developed a new design of therapeutic (or in vivo) siRNA composed of an intact antisense strand complemented with a discontinuous passenger strand, typically two shorter 9-13 nucleotides sense strands. We show that such a construct is fully functional and that it has several advantages over the standard 21 nt duplex siRNAs designs:

1. The segmented nature of the passenger strand completely alleviates its contribution to unwarranted gene knock down thereby greatly increasing targeting specificity and expectably reducing off-target effects.
2. The sisiRNA design has the ability to rescue the function of chemically modified antisense strands (such as antisense strands which include nucleotide analogues, such as LNA) that are non-functional within the context of a standard siRNA duplex thereby allowing more chemical modification (e.g. nucleotide analogues) to be incorporated into the antisense strand.
3. The sisiRNA design has at least six terminal ends compared to four in normal siRNA which can conveniently be used for tethering functional chemical groups to enhance e.g. cellular delivery. For instance, it is possible to tether bulky groups like cholesterol to the 5' end of the downstream sense strand without loosing activity.
4. As the yield of synthesis is usually higher for shorter RNA strands, the cost of large-scale synthesis in connection with therapeutic application may be reduced using an sisiRNA design.
5. The use of nucleotide analogues, particularly LNA in the sisiRNA passenger strand greatly enhances stability in serum leading to potent and prolonged gene silencing as compared to standard siRNAs.

Figure 17:
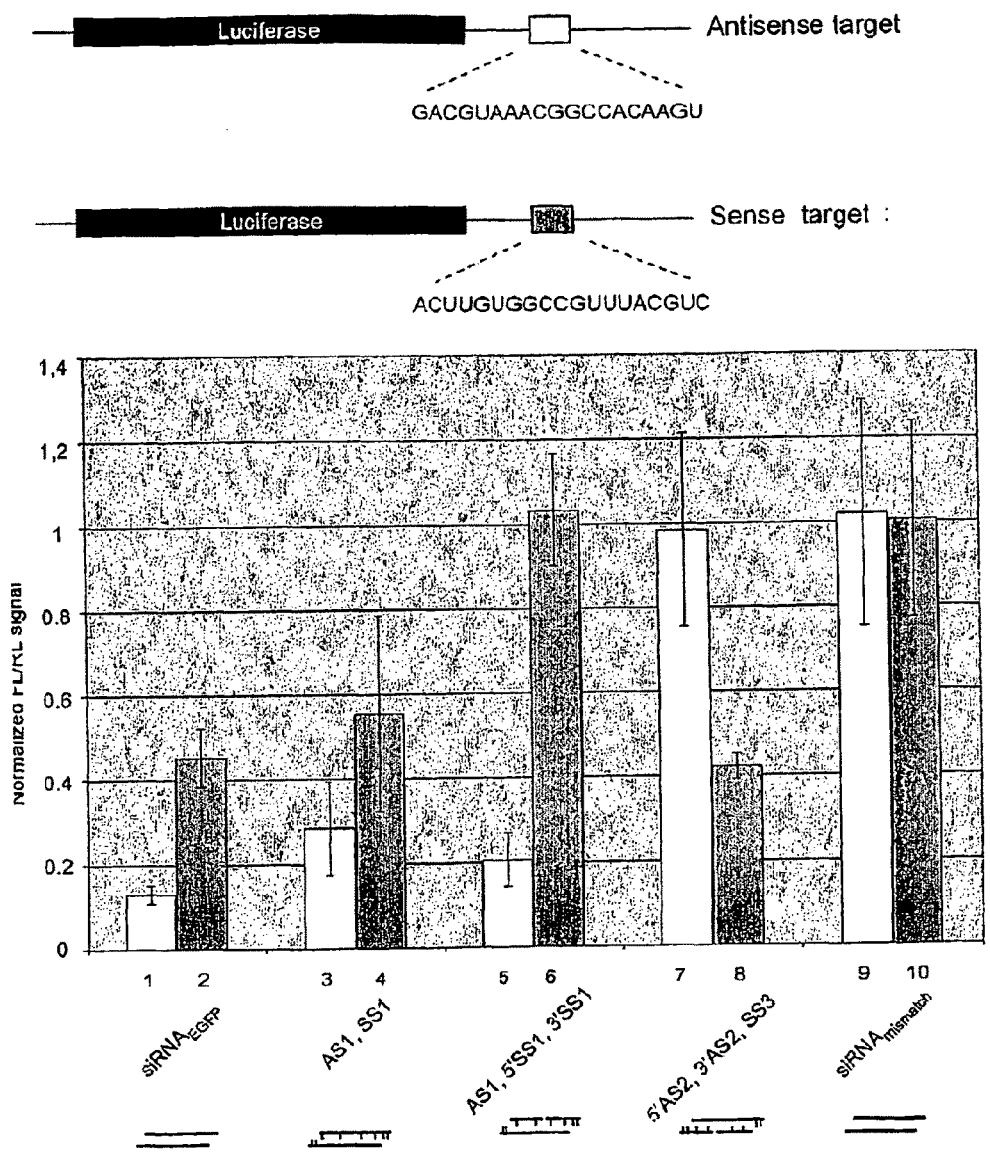
FIG. 17. The sisRNA design increases the specificity of gene silencing. The knockdown activity of the two strands was assessed by measuring luciferase expression from reporter constructs containing either the target sequence in the sense or the antisense orientation (white and grey bars, respective). The reporter constructs are drawn above (not to scale) and the siRNA constructs are indicated schematically below. The values are averaged over three completely independent experiments. The luciferase values of each experiment are normalized to make the sums of the luciferase activities in each of the experiments equal. For each reporter construct the firefly luciferase (FL)/renilla luciferase (RL) ratio was normalized to mismatch controls.

An important feature of the sisiRNA design is the ability to completely eliminate the contribution of the segmented strand to gene silencing while, leaving the RNAi activity of the opposing strand intact (as shown in FIG. 17). The resultant increase in gene silencing specificity can be expected to reduce the genome-wide off-targets effects from the sense strand that has been observed for other investigated siRNAs (Jackson, A. L. et al., (2003) Nat Biotechnol, 21, 635-637). Furthermore, as strand selection is primarily determined by the thermodynamic asymmetry of siRNA duplex ends, highly efficient siRNA may be difficult to design if the target sequence is restricted to a thermodynamically unfavorable region, e.g. when the intension is to target single nucleotide mutation or junctions between fused genes. In these instances, the sisiRNA design will ensure that only the unsegmented strand can contribute to gene silencing irrespectively of the thermodynamic profile of the sisiRNA duplex and will thereby eliminate the significant unwarranted silencing conferred by the thermodynamically-favored opposing strand.

Figure 15A:
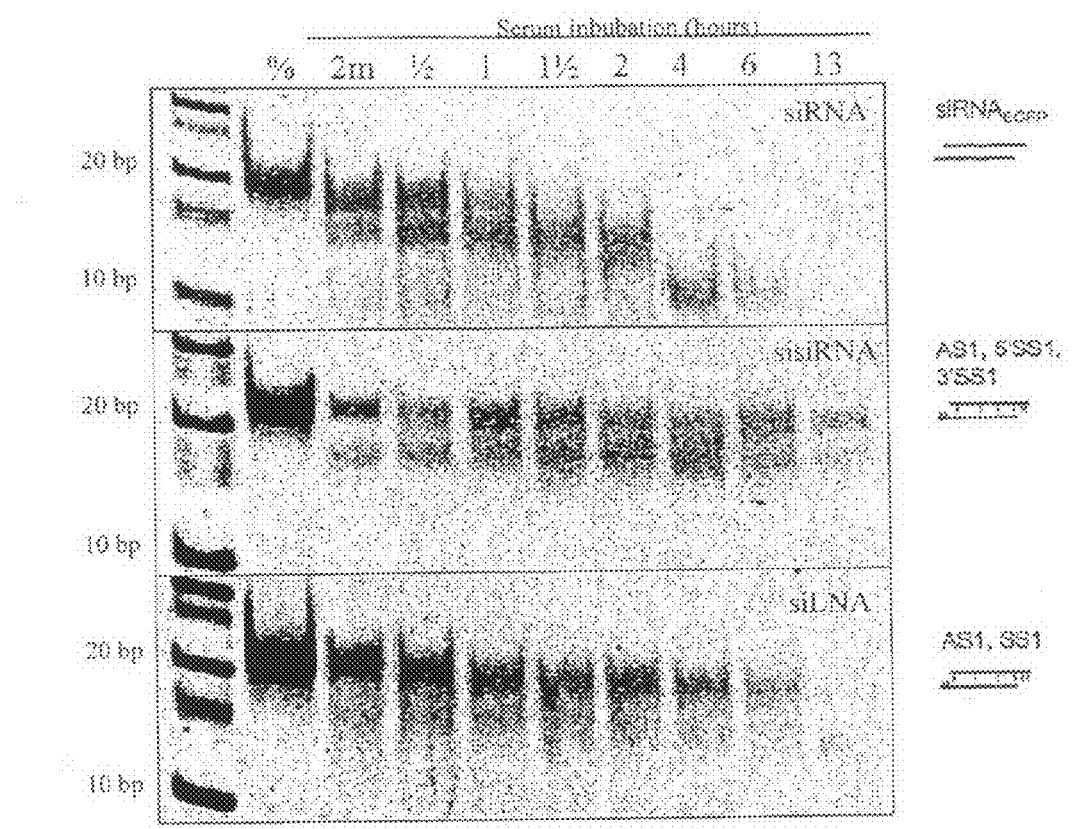
FIG. 15. sisiRNA and siLNA exhibit increased serum stability compared unmodified to siRNA Serum stability of the sisiRNA design. (A) LNA-modified sisiRNA and LNA-modified siRNA have increased serum stability compared to unmodified siRNA. The siRNA variants were incubated in 80% FCS and aliquots taken at indicated time points. Serum-stability was evaluated by PAGE followed by SYBR Gold® staining. Whereas siRNA is degraded within 1-1½ hours of serum incubation, significant amount of LNA-modified sisiRNA and LNA-modified siRNA are still present after 13 hours of incubation. A size marker is indicated to the left. (B) LNA-base pairing is essential for the integrity of sisiRNA molecules upon incubation in 10% FCS. The indicated sisiRNA molecules carrying different or no LNA modifications were incubated in the presence (+) or absence (−) of 10% FCS for 24 hours and duplex stability was evaluated by PAGE followed by SYBR Gold® staining. sisiRNA constructs with LNA in both strands exhibited full stability whereas sisiRNA containing only RNA were completely degraded upon serum incubation. The position of the LNA modifications are indicated schematically (vertical lines).

Leuchner et al. have previously demonstrated that pre-cleaved siRNA, similar to our unmodified sisiRNA, is capable of RISC loading and target cleavage in a cell extract. However, we find that sisiRNAs with passenger strands without LNA residues are non-functional in a cellular context (i.e. in viva), even if 2'OMe modified residues are introduced in the short sense strands. Based on our stability assays (FIG. 15A), the most likely explanation is that the unmodified strands in sisiRNA are dissociating and degraded in vivo and that only the significant increase in $T_m$, provided by the nucleotide analogue units, such as LNA units, renders the duplex sufficiently stable under these conditions.

Figure 16:
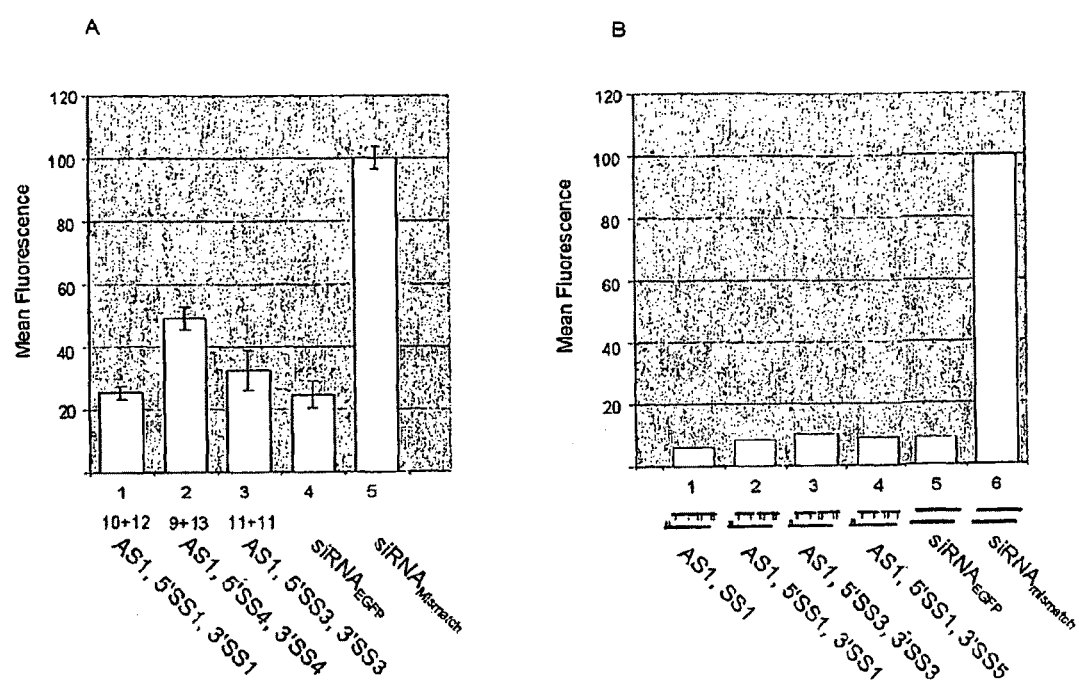
FIG. 16. Optimization the sisiRNA design. The knock down efficiencies between different sisiRNA and siRNA designs were compared by targeting EGFP mRNA. (A) Analyzing the effect of different gap positions in the sense strand. The numbers correspond to the size of the 5' and 3' fragment of the sense strand, respective. (B) Analyzing the effect of modifications at the 3' terminal nucleotide on the sense strand. Schematic drawings of the duplexes are indicated below. The Mean fluorescence of approximately 50.000 cells was measured by flow cytometry. The siRNA mismatch represents a siRNA that contains four mismatches to the EGFP target.

An interesting observation is that sisiRNA function does not rely strictly on exact structural mimicry of an intermediate Ago2-cleavage product as the strand nick can be moved 1-2 nt without major loss of silencing efficiency (FIG. 16A). In particular, the sisiRNA design mimicking the "natural" Ago2-cleavage product (sisiRNA$_{9+13}$) seems less efficient than when moving the nick 1 and 2 nt towards the 3 end of the sense strand (sisiRNA$_{10+12}$ and sisiRNA$_{11+11}$). Based on in vitro data from Leuchner et al. these constructs are most likely cleaved by Ago2, liberating one or two nucleotides, respectively. It is therefore possible that allowing a "natural" Ago2 cleavage event in the sisiRNA$_{10+12}$ and sisiRNA$_{11+11}$ designs may further help RISC activation by facilitating subsequent steps in RISC activation such as e.g. sense strand elimination. Hence we consider that the sisiRNA$_{10+12}$ design introduces novel improvements in siRNAs function beyond those offered by the structural mimicry of natural Intermediates in the RNAi pathway.

We and others have observed that extensive chemical modifications in the antisense strand of siRNAs generally are incompatible with their function in gene silencing. Interestingly, the sisiRNA design can ensure loading of heavily modified antisense strands into activated RISC that will subsequently guide efficient Ago2-mediated target mRNA cleavage. In the present invention we show that the inability of extensively LNA-modified, LNA/adamantyl and LNA/pyrenyl-modified antisense strands to support RISC activity can be partially rescued by the sisiRNA-design, whereas similarly modified ordinary siRNAs are non-functional (FIG. 18). This shows that modifications in the central part of the antisense strand do not impair the target cleavage reaction by activated RISC itself, but rather the recruitment of the siRNA to the RLC, sense strand cleavage and/or the unwinding of the duplex. Furthermore, the observation that multiple modifications in the antisense also do not appear to induce sense strand incorporation into activated RISC implies that it is not simply a shift in strand selection (FIG. 18). In agreement with this, the rescue of silencing by the sisiRNA design seems not to rely on alteration of the siRNA thermodynamic profile as the adamantyl and pyrenyl modifications, if anything, slightly destabilize siRNA duplexes in contrast to the stabilizing effect of the LNA-residues. Therefore the most obvious explanation for sisiRNA effect is that heavily modified siRNAs may either be too rigid or bulky to be recognized by Ago2 during RISC activation resulting in loss of sense-strand cleavage and its subsequent removal. Although not wishing to be bound to a specific theory, we consider a plausible explanation is that the central strand nick in the sisiRNA design may provide more structural flexibility to the sisiRNA duplex allowing it to better position itself for Ago2 cleavage during RISC activation.

Introducing extensive chemical modifications into a siRNA may have beneficial properties for steps both upstream and downstream of RISC activation in the RNAi pathway. Introducing lipophilic groups like adamantyl and pyrenyl may increase cellular uptake of siRNA duplexes and unnatural modifications in general will increase siRNA biostability in intra- and extracellular compartments. Furthermore, modifications in the seed region (nucleotide 2-8 of the antisense strand) may prove essential to minimize inherent gene off-target effects by siRNAs as it has been previously been demonstrated for position 2 in the antisense strand (Jackson, A. L. et al. (2006) RNA). We also consider that increased numbers of LNA residues in the antisense strand may improve the target specificity and affinity towards the target.

One object of the present invention is to control which strand of a double stranded RNA complex will actually function as a guide RNA in a RGPC. By definition, the antisense strand is intended to be the guide strand. But it is to be understood that a concern in using double stranded RNA complexes to mediate modification of target nucleic acids is that the wrong strand of the complex will act as a guide strand. Thus, it is not intended that the passenger strand should mediate any modification of target nucleic acids.

In other words, it is an object of the invention to secure that only the antisense strand, and not the passenger strand, will mediate modifications of target nucleic acids. The fulfillment of this object will provide RNA complexes with less off target effects.

The basic idea of the invention is to use a discontinuous passenger strand, as such discontinuous passenger strand will most likely not be incorporated into an RGPC in the cell, and consequently not be able to guide any modifications of target nucleic acids. In other words, the discontinuity defines the passenger strand by bringing an asymmetry to the duplex.

As the name implies, the discontinuous passenger strand comprises a discontinuity. The discontinuity may e.g. be a nick or a gap or it could be a linker, as will be clear from the specification below.

RNA complexes of the invention comprising a discontinuous passenger strand are also herein termed small internally segmented interfering RNA (sisiRNA).

The passenger strand may comprise several separate RNA molecules, such as 1, 2, 3 or 4 RNA molecules. These RNA molecules may be linked to each other and they may also be linked to the antisense strand. Accordingly when referring to the passenger strand, what is meant is generally the RNA molecule or RNA molecules that are hybridised to the antisense strand, notwithstanding that they are separated by a discontinuity. The passenger strand is also herein referred to as the sense strand.

The function of passenger strand may be to aid the antisense strand in reaching its destination and in incorporation of the antisense strand into the RGPC, which among others means that the passenger strand increases the bioavailability and biostability of the antisense strand. Thus, in one embodiment, discontinuous passenger strands of the invention are any that satisfy the above-mentioned functions, while at the same time fulfilling the structural claims described for the RNA complexes of the invention.

In one aspect, the present invention provides an RNA complex capable of mediating nucleic acid modifications of a target nucleic acid. The RNA complex comprises a core double stranded region comprising an antisense strand and a discontinuous passenger strand that is hybridised to the antisense strand. Some structural features of such a complex are given in FIGS. 1A and 1B.

A target nucleic acid as referred to in the present context is a nucleic acid which has significant complementarity to the antisense strand of the complex. Preferably, complementarity is perfect over a stretch of several nucleotides.

Thus, in one embodiment, complementarity is perfect over a stretch of 25 nucleotides.

In other embodiments, complementarity is perfect over a stretch of 24 nucleotides, 23 nucleotides, 22 nucleotides, 21 nucleotides, 20 nucleotides, 19 nucleotides, 18 nucleotides, 17 nucleotides, 16 nucleotides, 15 nucleotides, 14 nucleotides, 13 nucleotides, 12 nucleotides, 11 nucleotides, 10 nucleotides, 9 nucleotides or 8 nucleotides, respectively.

In one embodiment, the stretch of complementarity (such as those listed as 'perfect' above) comprises 1 mismatch. In other embodiments, the stretch of complementarity comprises 2 mismatches, 3 mismatches or 4 mismatches, respectively. A mismatch of 1 is a region in the stretch of complementarity where a base pair cannot form, e.g. when G is opposite to A. When more mismatches are present they may be adjacent to each other or they may be spaced in different regions of the stretch of complementarity.

The RNA complex comprises a core double-stranded region, which is a substantially double-stranded region. Single-stranded regions in the RNA complex are primarily related to the discontinuity of the passenger strand and to overhangs of the complex. Overhangs are by their nature single stranded and the discontinuity may give rise to single stranded regions in the antisense strand or the discontinuity may in itself be a single stranded region (a bulge). In addition to single-stranded regions related to the discontinuity of the passenger strand, the substantially double-stranded region may comprise a mismatch.

Thus, in one embodiment, the double-stranded region comprises 1 mismatch. In other embodiments, the double-stranded region comprises 2 mismatches, 3 mismatches and 4 mismatches, respectively.

As used herein, the term "target nucleic acid" may encompass any RNA/DNA that would be subject to modulation guided by the antisense strand, such as targeted cleavage or steric blockage. The target RNA/DNA could, for example be genomic DNA, genomic viral RNA, mRNA, a pre-mRNA, or a non-coding RNA. The preferred target is mRNA, such as the mRNA encoding a disease associated protein, such as ApoB, Bcl2, Hif-1alpha, Survivin or a p21 ras, such as Ha.ras, K-ras or N-ras.

As used herein, the term "target nucleic acid modification" means any modification to a target nucleic acid, including those that affect the activity of the target nucleic acid, without affecting the structure of the target nucleic acid.

The term "pharmaceutical composition" as used herein is equivalent to and interchangeable with the term "therapeutic" or "therapeutic composition". In this respect, the composition of the invention may be used prophylactically or in response to the presentation of a disease phenotype or diagnosis.

The terms "corresponding to" and "corresponds to" refer to the comparison between either a nucleobase sequence of the compound of the invention, and the reverse complement thereof, or in one embodiment between a nucleobase sequence and an equivalent (identical) nucleobase sequence which may for example comprise other nucleobases but retains the same base sequence, or complement thereof. Nucleotide analogues are compared directly to their equivalent or corresponding natural nucleotides. Sequences which form the reverse complement of a sequence are referred to as the complement sequence of the sequence.

A preferred target nucleic acid of the invention is mRNA. Accordingly, in one embodiment the nucleic acid modification mediated by the RNA complex is RNA interference (RNAi). In a preferred embodiment, RNAi mediates degradation of the mRNA. In another preferred embodiment, RNAi mediates translational inhibition of the mRNA. In another embodiment, the RNAi mediates both translational inhibition and degradation of the mRNA.

In one embodiment the nucleic acid modification mediated by the RNA complex is gene silencing, such as gene-suppression. The gene-silencing may be partial of complete, and for example may be mediated by RNA cleavage, RNA degradation and/or translational inhibition.

In other embodiments, the target nucleic acid is a non-coding RNA, e.g. a tRNA, miRNA and their precursors, snRNA, snoRNA or an rRNA.

In still another embodiment, the target nucleic acid is genomic DNA. In such embodiments, preferred nucleic acid modifications include DNA methylation and DNA deletion.

As used herein, the term "nucleobase" means a nucleotide, such as DNA or RNA or nucleotide analogue.

When referring to the length of a nucleotide molecule as referred to herein, the length corresponds to the number of monomer units, i.e. nucleobases, irrespective as to whether those monomer units are nucleotides or nucleotide analogues. With respect to nucleobases, the terms monomer and unit are used interchangeably herein.

The size of the RNA complex of the invention can be varied while still fulfilling on or more objects of the invention. This e.g. applies where the particular object is reduced off-target effect.

Thus, the core double-stranded region may comprise a number of base pairs selected from the group of 10 base pairs, 11 base pairs, 12 base pairs, 13 base pairs, 14 base pairs, 15 base pairs, 16 base pairs, 17 base pairs, 18 base pairs, 19 base pairs, 20 base pairs, 21 base pairs, 22 base pairs, 23 base pairs, 24 base pairs and 25 base pairs, 26 base pairs, 27 base pairs, 28 base pairs, 29 base pairs, 30 base pairs.

Thus, in the same or different embodiment, the core double-stranded region may comprise a number of base pairs selected from the group of 35 base pairs, 40 base pairs, 42 base pairs, 45 base pairs, 50 base pairs, 55 base pairs, 60 base pairs or 62 base pairs.

In one embodiment, the core double stranded region comprises between 15 and 40 base pairs.

In another preferred embodiment, the core double stranded region comprises 18-22 base pairs.

In one embodiment, the core double stranded region is even longer than 40 base pairs, although it is known that in some cells, the introduction of longer double stranded RNA complex increases the probability of induction of an interferon dependent non-specific response. In one such embodiment, it is contemplated that the complex is processed to shorter double-stranded RNA complexes before engaging with a RGPC. An RNase III like enzyme such as DICER may execute processing.

In a preferred embodiment of the invention, the RNA complex comprises overhangs. An overhang as used in the present context refers to a short single-stranded region following a double-stranded region. Various examples of RNA complexes comprising overhangs are shown in FIG. 2.

In one embodiment, the antisense strand of the RNA complex comprises a 3'-overhang.

In another embodiment, the passenger strand comprises a 3'-overhang

In yet another embodiment, the antisense strand comprises a 5'-overhang

In still another embodiment, the passenger strand comprises a 5'-overhang

In a preferred embodiment, both the antisense strand and the passenger strand comprise a 3'-overhang Other combinations of overhangs will be apparent from FIG. 2.

The overhangs of the RNA complex can be of varying length, without interfering with the basic function of the complex. Thus, in one embodiment the overhangs are selected from the group of overhangs with a length of 1 nucleotide, 2 nucleotides, 3 nucleotides, 4 nucleotides, 5 nucleotides, 6 nucleotides, 7 nucleotides and 8 nucleotides.

Most preferred overhangs are overhangs with a length of 1, 2 and 3 nucleotides, respectively.

In one embodiment, the overhang of the antisense strand has the same length as the overhang of the passenger strand.

In another embodiment, the overhang of the antisense strand does not have the same length as the overhang of the passenger strand In still another embodiment of the invention, the RNA complex comprises at least one blunt end. A "blunt end" refers to an end of a double-stranded nucleic acid, which does not have any protruding nucleotides, i.e. both strands of the double-stranded nucleic acid ends at the same position.

In another embodiment, the RNA complex is blunt ended at both ends.

Preferred RNA complexes of the invention are similar in structure to the products of DICER processing of longer double stranded RNA complexes, except for the discontinuity of the passenger strand.

Other preferred RNA complexes are similar in structure to the products of Ago2 endonuclease processing of the passenger strand. Not intended to be bound by theory, recent data suggest that the catalytic core protein of RISC, the Ago2 endonuclease, initiates passenger strand elimination by cleaving it 9 nucleotides form its 5'-end during RISC activation.

Other preferred RNA complexes of the invention are complexes wherein the core double-stranded region comprises 18-22 base pairs, and wherein the antisense strand and the passenger strand each comprise a 3'-overhang of 1-3 nucleotides (i.e. 1, 2 or 3).

The antisense strand of the RNA complex of the invention can have varying lengths, without interfering with the function of the complex. Thus, in some embodiments, the antisense strand is a 15-mer, 16-mer, 17-mer, 18-mer, 19-mer, 20-mer, 21-mer, 22-mer, 23-mer, a 24-mer, a 25-mer, a 26-mer, a 27-mer, a 28-mer, 29-mer, 30-mer, 31-mer, 32-mer, 33-mer, 34-mer, 35-mer, 36-mer, 37-mer, 38-mer, 39-mer, 40-mer, 41-mer, 42-mer, 43-mer, 44-mer, 45-mer, 46-mer, 47-mer, 48-mer, 49-mer, 50-mer, 51-mer, 52-mer, 53-mer, 54-mer, 55-mer, 56-mer, 57-mer, 58-mer, 59-mer, 60-mer, 61-mer or a 62-mer, respectively.

It is to be understood that e.g. a 19-mer is an antisense strand of 19 monomers, i.e. nucleotides/nucleotide analogues (nucleobases).

In another preferred embodiment, the antisense strand of the RNA complex is selected from the following group of antisense strands: An 18-mer, 19-mer, 20-mer, 21-mer, 22-mer and a 23-mer.

In one embodiment, the antisense strand is discontinuous. Preferred discontinuities of the antisense strands are the same as the preferred discontinuities of the passenger strand.

As outlined earlier, the passenger strand of the invention is discontinuous. In a preferred embodiment of the invention, the passenger strand comprises several separate RNA molecules. The number of RNA molecules may for example be 1, 2, 3, 4, 5 or 6. RNA complexes with several separate RNA molecules are outlined in FIG. 3.

In a preferred embodiment, the length of individual RNA molecules of the passenger strand is above 4 monomers. In other preferred embodiments, the length of individual RNA molecules of the passenger strand is above 5 monomers, 6 monomers, 7 monomers, 8 monomers, 9 monomers, 10 monomers, 11 monomers and 12 monomers, respectively.

In another embodiment, the length of individual RNA molecules of the passenger strand is below 4 monomers. In other embodiments, the length of individual RNA molecules of the passenger strand is below 5 monomers, 6 monomers, 7 monomers, 8 monomers, 9 monomers, 10 monomers, 11 monomers and 12 monomers, respectively.

In a preferred embodiment of the invention, the discontinuous passenger strand comprises a first and a second RNA-molecule, which together forms the discontinuous passenger strand, wherein the first RNA molecule is hybridised to the downstream part of the antisense strand and the second RNA molecule is hybridised to the upstream part of the antisense strand.

In one embodiment the passenger strand comprises of at least a first and a second RNA molecule, which together form the discontinuous passenger strand.

In one embodiment the passenger strand comprises of only two RNA molecules, the first and the second RNA molecules referred to above.

In one embodiment the passenger strand comprises of both the first and the second RNA molecules referred to above and at least one further RNA molecule.

An interesting embodiment is when the first RNA molecule comprises at least 3, such as 4, 5, 6, 7, 8, 9, 10, 11, 12 or 13 nucleotide analogue units, such as LNA units. In such as embodiment the second RNA molecule may contain only a few nucleotide analogue units, such as 3, 2, 1 or even no nucleotide analogue units. Alternatively it may be the second RNA molecule which comprises at least 3, such as 4, 5, 6, 7, 8, 9, 10, 11, 12 or 13 nucleotide analogue units, such as LNA units, and the first RNA molecule which may contain only a few nucleotide analogue units, such as 3, 2, 1 or even no nucleotide analogue units. Alternatively both first and second strand may comprise at least 3, such as 4, 5, 6, 7, 8, 9, 10, 11, 12 or 13 nucleotide analogue units, such as LNA units.

The at least on further RNA molecule preferably has a length of at least 3 nucleobase units, such as between 3 and 9 nucleobase units, such as 3, 4, 5, 6, 7, 8 or 9 nucleobase units, or such as between 4 and 6 nucleobase units.

Typically, the shorter the length of the RNA molecule(s) which form up the passenger strand a higher load of nucleotide analogues is preferred to ensure that the strength of the duplex is sufficient to allow for sufficient in vivo stability.

In one embodiment the passenger strand comprises of both the first and the second RNA molecules referred to above and between 1 and 4 further RNA molecules as referred to above, such as 1, 2, 3 or 4 further RNA molecules.

In one embodiment, the passenger strand comprises a first RNA molecule which is between 8 and 13 nucleobases units in length, such as 8, 9, 10, 11, 12 or 13 nucleobases units in length, such as between 9 and 12 nucleobases units in length, such as between 9 and 11 nucleobases in length. We have found that passenger strands with a first RNA molecule which is 9, 10 or 11 nucleobases in length are particularly effective. During processing in the RISC complex the passenger strand is typically nicked at position 9 of the passenger strand. We have surprisingly found that in the context of the RNA complexes according to the present invention that introducing a nick into a synthetic siRNA at position 10 or 11 by provision of first RNA molecule which is 10 or 11 nucleobase units in length provides very effective siRNA molecules which appear to be enhanced over similar siRNA complexes which comprise a second RNA molecule which has a length of 9 nucleobase units. In such embodiments there may be no further RNA molecules in the discontinuous passenger strand.

In one embodiment which may be the same or different to the above embodiment, the passenger strand comprises a second RNA molecule which is between 8 and 14 nucleobases units in length, such as 8, 9, 10, 11, 12, 13 or 14 nucleobases units in length, such as between 9 and 13 nucleobases units in length, such as between 10 and 13 nucleobases in length. We have found that passenger strands with a first RNA molecule which is 11, 12 or 13 nucleobases in length may be particularly effective. In such embodiments there may be no further RNA molecules in the discontinuous passenger strand.

In one embodiment, the passenger strand comprises a first RNA molecule which has a length of 9 nucleobase units and a second RNA molecule which has a length of either 12 or 13 nucleobase units. Preferably the total length of the discontinuous passenger strand is 21 (9/12) or 22 (9/13) nucleobases. In such embodiments there may be no further RNA molecules in the discontinuous passenger strand.

In one embodiment, the passenger strand comprises a first RNA molecule which has a length of 10 nucleobase units and a second RNA molecule which has a length of either 11 or 12 nucleobase units. In such embodiments there may be no further RNA molecules in the discontinuous passenger strand.

In one embodiment, the passenger strand comprises a first RNA molecule which has a length of 11 nucleobase units and a second RNA molecule which has a length of either 10 or 11 nucleobase units. In such embodiments there may be no further RNA molecules in the discontinuous passenger strand.

In one embodiment, the combined length of the first and second and optionally further RNA molecules (i.e. the discontinuous passenger strand, excluding any optional linking nucleobases) is between 18 and 25 nucleobases, such as 18, 19, 20, 21, 22, 23, 24 or 25 nucleobases in length, preferably between 21 and 23 nucleobases in length (21, 22 or 23).

Suitably, in one embodiment, the length of the antisense strand, excluding any optional linking nucleobases, is the same as the length of the discontinuous passenger strand.

In one embodiment, the first, second and/or further RNA molecules may comprise a nucleotide analogue. The use of nucleotide analogues can be used to create a molecule which forms an RNA like structure and/or functions like an RNA molecule within the context of the invention whilst comprising fewer RNA molecules than the passenger strand of an equivalent unmodified siRNA, including few or even no actual RNA monomers. For example the use of sufficient LNA units within a DNA molecule can create a molecule which functions as a passenger strand. In such an embodiment, within the context of a first, second and/or further RNA molecule (i.e. the RNA molecules which form the discontinuous passenger strand) molecules which comprise or consist of nucleobases other than RNA may be used so long as the molecule functions as if it was an RNA molecule in the context of an siRNA silencing complex. Suitably, in one embodiment the passenger strand, such as the first, second and/or further RNA molecules, comprise at least one LNA monomer and optionally DNA monomers, such as the passenger strand, such as the first, second and/or further RNA molecules consist of LNA and DNA monomers. Suitable patterns of inclusion of LNA into DNA molecules to produce an RNA like molecule include the insertion of an LNA at every other, or at every third nucleobase position (as shown in FIG. 19).

In one embodiment the passenger strand comprises nucleobase units which are only LNA and DNA, such as alternating LNA and DNA units.

In one embodiment the passenger strand comprises nucleobase units which are only LNA and RNA, such as alternating LNA and RNA units.

It is also envisaged that unmodified DNA residues may be used in the passenger strands or even in one embodiment the antisense strand.

However in one embodiment the passenger strands and/or antisense strands do not comprise unmodified DNA nucleotides.

Combination of LNA and other nucleotide analogues such as 2'OMethyl (2'OMe) and 2'fluoro (2° F.) are also considered as possible designs for the discontinuous passenger strands or individual RNA molecules which form the discontinuous passenger strand and/or in one embodiment the antisense strand. For example alternating LNA and 2'OMethyl (2'OMe), alternating LNA and 2'fluoro, alternating 2'OMethyl (2'OMe) and 2'fluoro. Such analogue rich strands are considered especially useful when considering RNA complexes which otherwise have a low $T_m$. An additional advantage of such analogue rich 'RNA' molecules and strands is that they can be used to provide a highly stable and nuclease resistant molecule in vivo, even when the internucleoside linkages are or include linkages which otherwise would be nuclease sensitive, such as phosphodiester or phosphate linkages. RNA complexes which comprise primarily or completely phosphodiester linkages may be preferable as they typically show a lower toxicity at high dosages as compared to equivalent molecules with phosphorothioate linkages.

However, in some embodiments, such as when using RNA molecules or strands which have a high DNA or RNA content it may be preferable to use nuclease resistant linkages such as phosphorothioate linkages. However, for some applications the use of RNA complexes with phosphorothioate linkages can cause toxicity problems, for instance when using the oligonucleotides within the brain or spinal cord/fluid.

Phosphorothioate linkages may be used in either the antisense and/or passenger strand molecules. Such strand/molecules may in one embodiment comprise other linkages, or mixtures of different linkages—for example both phosphate and phosphorothioate linkages, or just phosphate linkages, or other linkages as disclosed herein.

The internucleoside linkage may be selected form the group consisting of: —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —OPO(R$^H$)—O—, —O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, —NR$^H$—CO—NR$^H$—, and/or the internucleoside linkage may be selected form the group consisting of, —O—CO—O—, —O—CO—NR—, —NR$^H$—CO—CH—, —O—CH$_2$—CO—NR$^H$—, —O—CONR$^H$—CH$_2$—, CH$_2$—NR$^H$—CO—, —O—CH$_2$—CH$_2$—S—, —S—CH$_2$—CH$_2$—O—, —S—CH$_2$—CH$_2$—S—, —CH$_2$—SO$_2$—CH$_2$—, —CH$_2$—CO—NR$^H$—, —O—CH$_2$—CH$_2$—NR$^H$—CO—, —CH$_2$—NCH$_3$—O—CH$_2$—, where R$^H$ is selected from hydrogen and C$_{1-4}$-alkyl, Suitably, in some embodiments, sulphur (S) containing internucleoside linkages as provided above may be preferred The introduction of nicks (or in one embodiment, gaps) into the passenger strand will result in an effective reduction in the melting temperature of the RNA complex, thereby making the complex more prone to disassembly. In one embodiment the melting temperature of for each discontinuous strand molecule (i.e. each of the first, second or further RNA molecules which forms the discontinuous passenger strand) is above 37° C., such as at least 40° C., such as at least 45° C., preferably such as at least 50° C. If the length or GC content of part of a discontinuous strand molecule is too low so as to result in disassociation of the duplex in vivo, affinity enhancing nucleotide analogues can be used to increase the T$_m$. However, within the context of the present invention it is thought that each discontinuous strand molecule should be at least 3 nucleobases in length, such as at least 4, or at least 5, or at least 6, or at least 7, or at least 8 nucleobases in length.

Between the first and second RNA molecules, and optionally further RNA molecules, which together form the passenger strand there exists a discontinuity.

A highly preferred discontinuity of the invention is a nick. A nick is to be understood as a discontinuity in one strand of a double-stranded nucleic acid caused by a missing phosphodiester bond (a suitable inter-nucleobase linkage), however, without the double-stranded nucleic acid missing a nucleotide. Thus, the bases opposite to the nick will still be hybridised to bases on the nicked strand.

Another discontinuity of the invention is an alternative nick, which is understood as a discontinuity in one strand of a double-stranded nucleic acid caused by one missing bond, or more than one missing bond in the sugar-phosphate backbone, (in one embodiment, other than a phosphodiester bond), however, without the double-stranded nucleic acid missing a nucleobase. Thus, the bases opposite to the nick may still be hybridised to bases on the nicked strand.

It will be recognised that in some embodiments, the term nick as used herein can include the term 'alternative nick'.

A gap as used in the present context refers to a discontinuity where at least one nucleotide or nucleoside or a nucleobase is missing in the double-stranded nucleic acid.

In a preferred embodiment of the invention, a nick separates the first and the second RNA molecule, and optionally one or more further RNA molecules that form the discontinuous passenger strand.

In one preferred embodiment the discontinuous passenger strand does not comprise any gaps between the first and second and optionally further RNA molecules.

However, it is envisaged that in one embodiment the discontinuous passenger strand does comprise one (or optionally more) gaps between the first and second and optionally further RNA molecules.

In one embodiment, a gap separates the first and the second RNA molecule. In one embodiment, the gap is a 1-nucleotide gap. In other embodiments, the gap is a 2-nucleotide gap, a 3-nucleotide gap, a 4-nucleotide gap, a 5-nucleotide gap, a 6-nucleotide gap, a 7-nucleotide gap, an 8-nucleotide gap, a 9-nucleotide gap, a 10-nucleotide gap, an 11-nucleotide gap and a 12-nucleotide gap, respectively.

Figure 5:
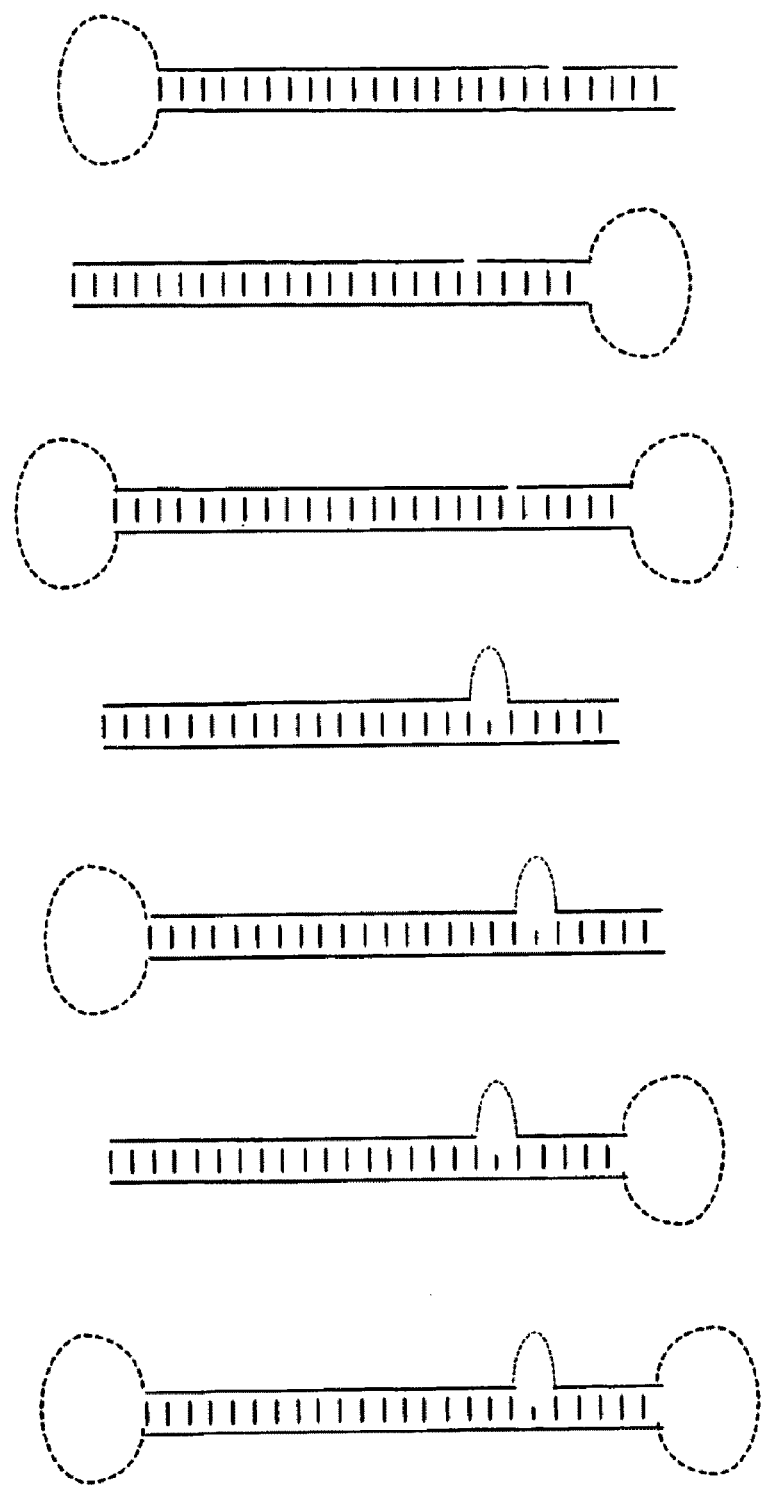
Figure 6:
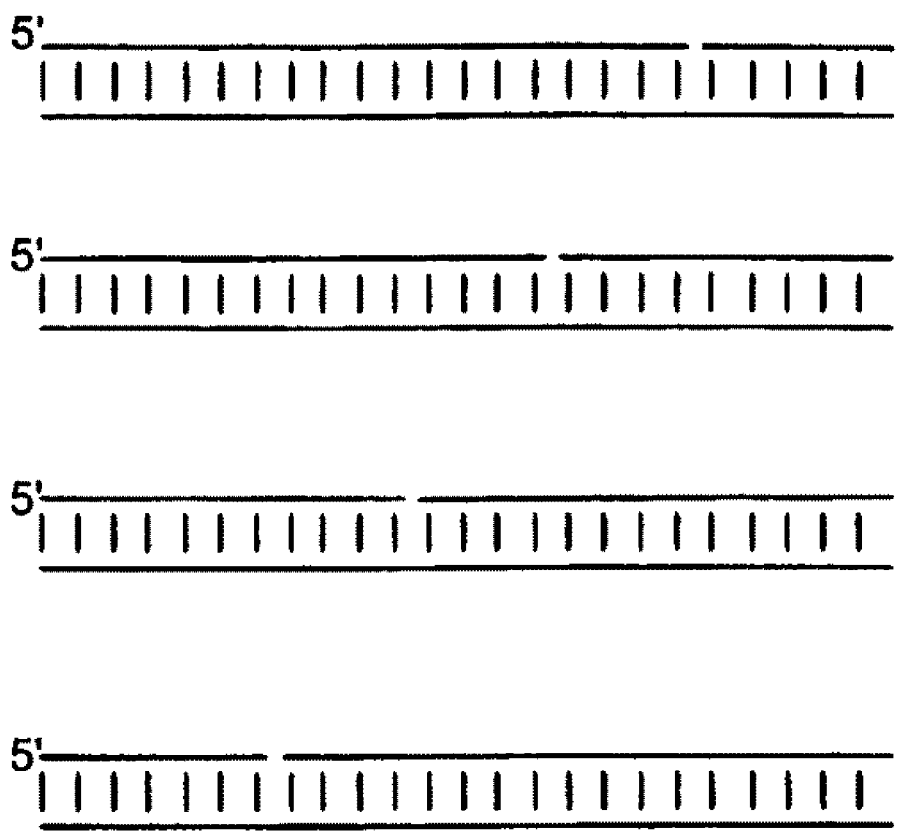

In one embodiment, the discontinued passenger strand of the RNA complex may be linked to the antisense strand. Various RNA complexes wherein the discontinued passenger strand is linked to the antisense strand are outlined in FIG. 5.

Thus, in one embodiment of the invention, the first RNA molecule is connected to the antisense strand by a linker.

In another embodiment, the second RNA molecule is connected to the antisense strand by a linker.

In still another embodiment, both the first and the second RNA molecule are connected to the antisense strand by a linker.

In yet another embodiment of the invention, a linker connects the first and the second RNA molecule of the discontinued passenger strand; wherein said linker is not a simple internucleoside linkage as referred to herein, such as a phosphodiester bond (if the linker is a simple phosphodiester bond, the passenger strand is a typical continuous passenger strand).

Preferred linkers of the invention are single stranded DNA, single stranded RNA and a PEG linker. If the first and the second RNA molecule are connected by a single stranded RNA (or other nucleobase sequence), the resulting discontinuity is actually what is often termed a bulge, i.e. at the discontinuity site the passenger strand comprises an additional nucleobase sequence which is not complementary to the antisense strands, which typically consists of at least one, such as at least two or at least three non-complementary nucleobases. It will be recognised that the inclusion of a bulge may interfere with the formation of the RISC complex, and therefore it will be desirable to keep the size of the bulge to a minimum, suitably the bulge is typically less than 10 non-complementary nucleobases in length.

In one embodiment, anything capable of functionally linking the RNA molecules of the RNA complex may be used as a linker. However it is typical that the linker is an organic entity which is covalently bound to each of the linked molecules, and is other than the internucleobase linkages which form the backbone (i.e. the nucleobases which form complementary hybrids with the opposite strand, taking into account the possibility of a mismatch and a 3' overhang) of the antisense or first, second or optionally further RNA molecules that form the discontinuous passenger strand.

However, in a preferred embodiment, the linker is not a single stranded RNA.

In one embodiment the linker is not a single stranded DNA molecule.

In one embodiment the linker does not comprise nucleobases.

In one embodiment, linkers of the invention are chosen such as to not affect the base pairing properties of the antisense strand and/or the passenger strand.

However, if the melting temperature of the first RNA molecule is too low for base pairing at a given temperature, connecting said first RNA molecule to the antisense strand to the antisense strand might increase the effective melting temperature. Thus, in another embodiment, linkers are chosen as to increase melting temperature of at least the first RNA molecule.

Linkers of the invention may also be chosen such as to provide conjugation sites that allow conjugation of other molecules to the RNA complex. Such other molecules may e.g. be carriers aiding the uptake of the RNA complex into a cell or organism. Or it may be molecules that directly affect the incorporation of guide strand into a RGPC, e.g. to further ensure that only the antisense strand is incorporated.

In a preferred embodiment of the invention, the passenger strand of the RNA complex comprises a first and a second RNA molecule that are not covalently linked to each other and also not covalently linked to the antisense strand. Thus, the RNA complex may comprise three individual RNA molecules, namely the antisense strand, and the first and the second RNA molecule, which together form the discontinued passenger strand. Clearly, in the case that the passenger strand comprises further RNA molecules, the RNA complex may comprise more than three individual RNA molecules.

In one embodiment, the use of the term RNA in this context refers to a polynucleobase sequence which, when hybridised to the antisense strand forms a complex which is capable of functioning as a siRNA and/or is capable of forming an A-form conformation.

In one embodiment the RNA molecules/passenger strand/antisense strand comprise at least 10% RNA nucleotides compared to the total number of nucleobases in the RNA molecules/passenger strand/antisense strand respectfully, such as at least 20%, such as at least 30%, such as at least 40%, such as at least 50%, such as at least 60%, such as at least 70%, such as at least 80%, such as at least 900% RNA nucleotides, or even 100% RNA nucleotides.

In another preferred embodiment, the passenger strand of the RNA complex comprises 3 RNA molecules that are not covalently linked. In other embodiments, the passenger strand comprises 4, 5 and 6 RNA molecules that are not covalently linked to each other and also not linked to the antisense strand.

When using a passenger strand of the RNA complex, which comprises two or more RNA molecules that are not covalently linked, chemical synthesis, may be more facile as compared to the synthesis of a continuous passenger strand, i.e. it is more facile to synthesize and purify two or more short RNA molecules than one longer RNA molecule.

Moreover, the use of two or more RNA molecules gives more synthetic freedom with regards to conjugation to the RNA molecules. One advantage is that separate RNA molecules can be conjugated separately, thus the same chemistry can be used on each RNA molecule. Another advantage is more conjugation points. E.g. the two 5-ends may each be conjugated to a particular group such as a ligand or an effector molecule.

The passenger strand of the RNA complex of the invention may comprise more than one discontinuity. In one embodiment, the passenger strand comprises 2 discontinuities. In other embodiments, the passenger strand comprises 3 discontinuities, 4 discontinuities and 5 discontinuities, respectively.

The discontinuity of the discontinued passenger strand may be located at various positions. Thus, in one embodiment, the discontinued passenger strand has a discontinuity at position 3 calculated in the 5' to 3' direction from the first nucleotide of the passenger strand base paired to the antisense strand.

In other embodiments, the discontinuity is at position 4, position 5, position 6, position, position 7, position 8, position 9, position 10, position 11, position 12, position 13, position 14, position 15, position 16, position 17, position 18, position 19, position 20, position 21, position 22, position 23, position 24, position 25 and position 26, respectively.

Preferred discontinuities may be selected form the group consisting of position 8, 9, 10, 11, 12, or 13 as counted from the 5' end of the passenger strand, most a single discontinuity in the passenger strand at one of these positions, such as between positions 9-12.

Preferably, the 5'-ends of the RNA complex is phosphorylated or is available for phosphorylation. Available for phosphorylation means that the 5'-hydroxy group has not been blocked e.g. by direct conjugation or by other conjugation to other groups in the vicinity of the 5'-hydroxy group, which will prevent the 5'-hydroxy group from being phosphorylated.

Hence, in a preferred embodiment of the invention, the first RNA molecule comprises a 5'-phosphate and a 3'-hydroxy group.

In another embodiment, the second RNA molecule comprises a 5'-end phosphate and a 3'-hydroxy group.

In yet another embodiment, the antisense strand comprises a 5'-end phosphate and a 3'-hydroxy group.

In a preferred embodiment, the RNA molecules which form the discontinuous passenger strand, such as the first RNA molecule, the second RNA molecule and/or further RNA molecules are capable of hybridising against the antisense strand to form a duplex with a $T_m$ of at least 37° C., such as at least 40° C., at least 50° C., at least 55° C., or at least 60° C. In one aspect the $T_m$ is between 37° C. and 80° C., such as between 50 and 70° C.

Measurement of $T_m$

A 3 µM solution of the compound in 10 mM sodium phosphate/100 mM NaCl/0.1 nM EDTA, pH 7.0 is mixed with its complement DNA or RNA oligonucleotide (preferably RNA) at 3 µM concentration in 10 mM sodium phosphate/100 mM NaCl/0.1 nM EDTA, pH 7.0 at 90° C. for a minute and allowed to cool down to room temperature. The melting curve of the duplex is then determined by measuring the absorbance at 260 nm with a heating rate of 1° C./min. in the range of 25 to 95° C. The $T_m$ is measured as the maximum of the first derivative of the melting curve.

In the context of the present invention "complementary" refers to the capacity for precise pairing between two nucleotides sequences with one another. For example, if a nucleotide at a certain position of an oligonucleotide is capable of hydrogen bonding with a nucleotide at the corresponding position of a DNA or RNA molecule, then the oligonucleotide and the DNA or RNA are considered to be complementary to each other at that position. The DNA or RNA and the oligonucleotide are considered complementary to each other when a sufficient number of nucleotides in the oligonucleotide can form hydrogen bonds with corresponding nucleotides in the target DNA or RNA to enable the formation of a stable complex. To be stable in vitro or in vivo the sequence need not be 100% complementary to its target nucleic acid, i.e. they may comprise one or more nucleotides or nucleotide analogues which do not pair with the corresponding nucleotide in the target DNA or RNA, these are referred to herein as "mismatches". The terms "complementary" and "hybridisable" thus imply that the compound of the invention binds sufficiently strongly and specifically to the target molecule to provide the desired interference with the normal function of the target(s). Suitably, the sequence of may comprise one mismatch or two mismatches. However, in one embodiment, apart from the possibility of 3' overhands, the discontinuous passenger strand and the antisense strand of the RNA complex according to the invention are complementary without any mismatches. In one embodiment the term complimentary means 100% complementary over the region of the duplex (i.e. excluding the 3' overhangs).

In some embodiments of the invention, it is preferred that the RNA complex comprises one or more nucleotide analogues.

The use of nucleotide analogues may be favoured for several reasons. They may e.g. be used to increase the melting temperature of the core double stranded region. If the first and/or second RNA molecules are short, they may have a melting temperature, which do not support stable base paring at a given temperature. In such a case, nucleotide analogues such as LNA may be used to increase the melting temperature. Nucleotide analogues may also be used to decrease the melting temperature of the core double stranded region. For this purpose, a basic nucleotides may be used. Moreover, nucleotide analogues may be used for reasons related to cost or ease of synthesis.

Accordingly, in a preferred embodiment, the antisense strand comprises nucleotide analogues.

In another preferred embodiment, the discontinued passenger strand comprises nucleotide analogues.

In yet another preferred embodiment, the first and the second RNA molecule of the passenger strand each comprise nucleotide analogues.

In one embodiment of the invention, the number of nucleotide analogues in the antisense strand is 10. In other embodiments of the invention, the number of nucleotide analogues in the antisense strand is 9, 8, 7, 6, 5, 4, 3, 2 or 1, respectively.

In another embodiment, all nucleotides of the antisense strand are nucleotide analogues.

In one embodiment of the invention, the number of nucleotide analogues in the antisense strand is 25, 24, 23, 22, 21, 20, 19, 18, 17, 16, 15, 14, 13, 12, or 11.

In one embodiment the antisense strand comprises between 0 and 10, such as between 1 and 8, such as between 2 or 3 and 8 nucleotide analogues.

Likewise, in another embodiment of the invention, the number of nucleotide analogues in the passenger strand is 10. In other embodiments of the invention, the number of nucleotide analogues in the passenger strand is 9, 8, 7, 6, 5, 4, 3, 2 or 1, respectively.

In another embodiment, all nucleotides of the passenger strand are nucleotide analogues.

In one embodiment of the invention, the number of nucleotide analogues in the passenger strand is 25, 24, 23, 22, 21, 20, 19, 18, 17, 16, 15, 14, 13, 12, or 11.

In one embodiment the passenger strand comprises between 0 and 10, such as between 1 and 8, such as between 2 or 3 and 8 nucleotide analogues.

In a preferred embodiment, both the antisense strand and the passenger strand comprise nucleotide analogues.

In one embodiment, the nucleotide analogues of the RNA complex are identical, i.e. they are for example all LNA. In another embodiment, various different nucleotide analogues are used in the same RNA complex.

In one embodiment, the nucleotide analogues of the passenger strand are identical, i.e. they are for example all LNA. In another embodiment, various different nucleotide analogues are used in the same passenger strand.

In one embodiment, the nucleotide analogues of the antisense strand are identical, i.e. they are for example all LNA. In another embodiment, various different nucleotide analogues are used in the same antisense strand.

In one embodiment the first RNA molecule of the passenger strand comprises one or more nucleotide analogues.

In one embodiment the first RNA molecule of the passenger strand comprises at least 2 nucleotide analogues.

In one embodiment the second RNA molecule of the passenger strand comprises one or more nucleotide analogue.

In one embodiment the second RNA molecule of the passenger strand comprises at least 2 nucleotide analogues.

In one embodiment a nucleotide analogue is located within the three terminal (5' or 3' respectfully) nucleobase units of the first and/or second RNA molecule, such as position 1, 2 or 3 of the respective terminal nucleobase units.

In one embodiment at least one of the further RNA molecules of the passenger strand comprise at least one nucleotide analogue.

In one embodiment each further RNA molecule which forms part of the discontinuous passenger strand comprises at least one nucleotide analogue.

In one embodiment the discontinuous passenger strand comprises a nucleotide analogue at positions 10 and 12 from the 5' end of the passenger strand.

In one embodiment each RNA molecule which forms part of the discontinuous passenger strand comprises at least one nucleotide analogue.

In one embodiment the melting temperature ($T_m$) of for each of the first, second and optionally further RNA molecules which form the discontinuous passenger strand is at least 40° C.

In one embodiment the length of each of the first, second and optionally further RNA molecules which form the discontinuous passenger strand is at least three nucleobase units.

In one embodiment the antisense strand comprises at least 1 nucleotide analogue.

In one embodiment the antisense strand comprises at least 1 nucleotide analogue within the duplex region formed with the discontinuous passenger strand.

In one embodiment the antisense strand comprises at least one nucleotide analogue at a position which is within 4 nucleobases as counted from the 3' end of the antisense strand, such as position 1, 2, 3 and/or 4 from the 3' end of the antisense strand.

In one embodiment at least one of the nucleobases present in the 9 5' most nucleobase units of the antisense strand is a nucleotide analogue.

In one embodiment at least one of the nucleobases present in the region within 4-10 nucleobases from the 3' end 10 of the antisense strand is a nucleotide analogue.

In one embodiment the antisense strand has a nucleotide analogue at position 11 from the 5' end of the antisense strand.

In one embodiment the antisense strand has RNA nucleotides at position 10 and 12 from the 5' end of the antisense strand.

In one embodiment the 5' most nucleobase units of the antisense strand is an RNA nucleotide unit.

In one embodiment the antisense strand comprises at least 2 nucleotide analogues.

In one embodiment the nucleotide analogues are compatible with the formation of an A-form (or in one embodiment an A/B form—i.e. a form between the A and B form conformation) conformation when in a duplex with a complementary RNA molecule consisting of only RNA units linked by phosphate bonds.

In one embodiment the nucleotide analogues present in antisense strand and/or passenger strand are independently selected from the group consisting of: 2'-o-alkyl-RNA monomers (such as 2'OME), 2'-amino-DNA monomers, 2'-fluoro-DNA monomers, arabino nucleic acid (ANA) monomers, 2'-fluoro-ANA monomers, LNA monomers, INA monomers.

In one embodiment the nucleotide analogues present in discontinuous passenger strand (or antisense strand, or both, either as separate entities or as a combined total of nucleotide analogues within the RNA complex) include at least one of the above nucleotide analogues (either individually, e.g. just 2'OME or collectively, such as selected from the above), such as 1, 2, 3, 4, 5, 6, 7, 8, 9, 10, 11, 12, 13, 14, 15, 16, 17, 18, 19, 20, 21, 22, 23, 24 or 25 nucleotide monomers.

Preferred nucleotide monomers, apart from LNA include 2'-O-alkyl-RNA monomers (such as 2'OME), and 2'-fluoro-DNA monomers.

In one embodiment the number of nucleotide analogues present in the antisense strand or passenger strand (or both, either as separate entities or as a combined total of nucleotide analogues within the RNA complex) is selected from the group consisting of: at least one nucleotide analogue, such as at least 2, at least 3, at least 4, at least 5, at least 6, at least 7, at least 8, at least 9, at least 10, at least 11, at least 12, at least 13, at least 14, at least 15, at least 16, at least 17, at least 18, at least 19 or at least 20, at least 21, at least 22, at least 23, at least 24 and at least 25 nucleotide analogues. Suitably the number of nucleotide analogues may be less than 20, such as less than 18, such as less than 16, such as less than 14, such as less than 12, such as less than 10.

In one embodiment the nucleotide analogues present in discontinuous passenger strand (or antisense strand, or both, either as separate entities or as a combined total of nucleotide analogues within the RNA complex) include at least one 2'-O-alkyl-RNA monomer (such as 2'OME), such as 1, 2, 3, 4, 5, 6, 7, 8, 9, 10, 11, 12, 13, 14, 15, 16, 17, 18, 19, 20, 21, 22, 23, 24 or 25 2'-O-alkyl-RNA monomers (such as 2'OME), In one embodiment, which may be the same of different, the nucleotide analogues present in discontinuous passenger strand (or antisense strand, or both, either as separate entities or as a combined total of nucleotide analogues within the RNA complex) include at least one 2'-fluoro-DNA monomer, such as 1, 2, 3, 4, 5, 6, 7, 8, 9, 10, 11, 12, 13, 14, 15, 16, 17, 18, 19, 20, 21, 22, 23, 24 or 25 2'-fluoro-DNA monomers.

In one embodiment the nucleotide analogues present in discontinuous passenger strand include at least one Locked Nucleic Acid (LNA) unit.

In one embodiment, which may be the same of different, the nucleotide analogues present in discontinuous passenger strand (or antisense strand, or both, either as separate entities or as a combined total of nucleotide analogues within the RNA complex) include at least one LNA monomer, such as 1, 2, 3, 4, 5, 6, 7, 8, 9, 10, 11, 12, 13, 14, 15, 16, 17, 18, 19, 20, 21, 22, 23, 24 or 25 LNA monomers.

In one embodiment the LNA unit or units are independently selected from the group consisting of oxy-LNA, thio-LNA, and amino-LNA, in either of the D-$\beta$ and L-$\alpha$ configurations or combinations thereof.

In one embodiment the nucleotide analogues present in the antisense strand include at least one Locked Nucleic Acid (LNA) unit, such as at least 2, at least 3, at least 4, at least 5, at least 6, at least 7, at least 8, at least 9, at least 10, at least 11, at least 12, at least 13, at least 14, at least 15, at least 16, at least 17, at least 18, at least 19 or at least 20 LNA units. Suitable the number of LNA units may be less than 20, such as less than 18, such as less than 16, such as less than 14, such as less than 12, such as less than 10.

In one embodiment all the nucleotide analogues present in antisense strand are Locked Nucleic Acid (LNA) units.

In a preferred embodiment, the antisense strand only comprises a few nucleotide analogue units, such as LNA units. Typically it is preferred the nucleotide units present in the antisense strand a positioned within the 3' half of the antisense strand such as between positions 1 and 9 of the antisense strand, such as position 1, 2, 3, 4, 5, 6, 7, 8, or 9 of the antisense strand, such as within the region of a 3 over-hang, or within the first 3, such first, second or third, nucleobase positions of the duplex as measured from the 3' end of the antisense strand.

In one embodiment the nucleotide analogues present in the passenger strand (or antisense strand, or both, either as separate entities or as a combined total of nucleotide analogues within the RNA complex) include at least one Locked Nucleic Acid (LNA) unit such as at least 2, at least 3, at least 4, at least 5, at least 6, at least 7, at least 8, at least 9, at least 10, at least 11, at least 12, at least 13, at least 14, at least 15, at least 16, at least 17, at least 18, at least 19 or at least 20 LNA units. Suitable the number of LNA units may be less than 20, such as less than 18, such as less than 16, such as less than 14, such as less than 12, such as less than 10.

In one embodiment all the nucleotide analogues present in passenger strand are Locked Nucleic Acid (LNA) units.

In one embodiment at least one of the nucleotide analogues present in the discontinuous passenger strand forms a base pair with a complementary nucleotide analogue present in the antisense strand.

In one embodiment all the nucleotide analogues present in the discontinuous passenger strand forms a base pair with a complementary nucleotide analogue present in the antisense strand, other than those nucleotide analogue present in the 3' overhang (if present).

In one embodiment all the nucleotide analogues present in the antisense strand forms a base pair with a complementary nucleotide analogue present in the discontinuous passenger strand, other than those nucleotide analogue present in the 3' overhang (if present).

In one embodiment the passenger strand consists or comprises of a 9-11 nucleotide (nucleobase) RNA molecule, such as a 10 nucleotide RNA molecule, with between 1 and five nucleotide analogues, such as LNA units, such as two LNA units and a 11-13 nucleotide RNA molecule, such as a 12 nucleotide RNA molecule, comprising between 1 and 5 nucleotide analogue units, such as LNA units, such as three LNA residues.

In one embodiment at least one of the three 3' terminal nucleobases of the second RNA molecule of the passenger strands is a nucleotide analogue, such as LNA. In such an embodiment the 3' terminal nucleobases of the second RNA molecule of the passenger strand may comprise one of the following nucleobase motifs Xxx-3', XXx-3', xXx-3', xxX-3', XXX-3' wherein x represents a RNA monomer, and X represents a nucleotide analogue unit, such as and LNA unit. In this embodiment the second RNA molecule of the passenger strands may comprise one or more further nucleotide analogue monomers, such as one or more further LNA monomer at a position, such as at a position 4, 5, 6, 7, 8, 9, 10, 11, 12 or 13 as counted from the 3' termini of the second RNA molecule. In one embodiment, the second RNA molecule of the passenger strand comprises 3, 4 or 5 nucleotide analogue units such as LNA monomer units.

In one embodiment at least one of the three 3' terminal nucleobases of the second RNA molecule of the passenger strands is a nucleotide analogue, such as LNA. In such an embodiment the 3' terminal nucleobases of the second RNA molecule of the passenger strand may comprise one of the following nucleobase motifs Xxx-3', XXx-3', xXx-3', xxX-3', XXX-3' wherein x represents a RNA monomer, and X represents a nucleotide analogue unit, such as and LNA unit. In this embodiment the second RNA molecule of the passenger strands may comprise one or more further nucleotide analogue monomers, such as one or more further LNA monomer at a position, such as at a position 4, 5, 6, 7, 8, 9, 10, 11, 12 or 13 as counted from the 3' termini of the second RNA molecule. In one embodiment, the second RNA molecule of the passenger strand comprises 3, 4 or 5 nucleotide analogue units such as LNA monomer units.

In one embodiment at least one of the three 5' terminal nucleobases of the first RNA molecule of the passenger strands is a nucleotide analogue, such as LNA. In such an embodiment the 5' terminal nucleobases of the first RNA molecule of the passenger strand may comprise one of the following nucleobase motifs 5'-Xxx, 5'-XXx, 5'-xXx, 5'-xxX, 5'-XXX wherein x represents a RNA monomer, and X represents a nucleotide analogue unit, such as and LNA unit. In this embodiment the first RNA molecule of the passenger strands may comprise one or more further nucleotide analogue monomers, such as one or more further LNA monomer at a position, such as at a position 4, 5, 6, 7, 8, 9, 10, 11, 12 or 13 as counted from the 5' termini of the first RNA molecule. In one embodiment, the first RNA molecule of the passenger strand comprises 3, 4 or 5 nucleotide analogue units such as LNA monomer units.

Suitably, the passenger strand may comprise 1, 2, 3, 4, 5, 6, 7, 8, 9, 10, 11, 12, 13, 14, 15, 16, 17, 18, 19, 20, 21, 22, 23 or 24 nucleotide analogues, such as an nucleotide analogue such as an LNA monomer at a position from the 5' end selected from the group consisting of: position 1, position 2, position 3. position 4, position 5, position 6, position 7, position 8, position 9, position 10, position 11, position 12, position 13, position 14, position 15, position 16, position 17, position 18, position 19, position 20, position 21, position 22, position 23 or position 24.

In one embodiment, the second RNA molecule of the discontinuous passenger strand comprises one or more 2'adementyl-amino and/or 2'pyrene LNA units.

FIG. 20 illustrates that the introduction of LNA into the first and second RNA molecules of the discontinuous passenger strand of the RNA complex according to the invention provides for a highly effective silencing of the target RNA as compared to an equivalent RNA molecule where the passenger strand comprises only RNA units. Indeed, a combination of both the incorporation nucleotide analogues such as LNA into the passenger strand and the discontinuity of the passenger strand allows for the production of a highly effective and stable RNA silencing complex, suitable for use in therapy (see FIG. 20).

Suitably the nucleotide analogues present in the passenger strand may be a 2' substituent modified nucleotides (RNA or DNA) such as a 2' halo substituted RNA or DNA units (such as 2'-F-DNA) or 2'-O-Me-RNA (see FIG. 21).

FIG. 22 illustrates that by the introduction of a discontinuous passenger strand, such as the discontinuous passenger strands according to the present invention, we have found that the passenger strand can tolerate more modified or functionalized nucleotide analogues, such as LNA or functionalized LNA.

In further embodiments, the second RNA molecule of the discontinuous passenger strand has a sequence (5'-3') selected from the group consisting of: xxXxXxxxxXXx, xxxXxxxxXXx, wherein x represents a RNA monomer, and X represents a nucleotide analogue unit, such as and LNA unit.

In a further embodiments, which may be the same of different to the one above, the first RNA molecule of the discontinuous passenger strand has a sequence (5'-3') selected from the group consisting of: xxXxxxxxXx wherein x represents a RNA monomer, and X represents a nucleotide analogue unit, such as and LNA unit.

The use of antisense strand which comprise nucleotide analogues, such as LNA can significantly reduce or even destroy the silencing capability of an RNA silencing complex. This sensitivity of the antisense strand to nucleotide modification (introduction of analogues), has been a hinderance in the development of siRNA based therapeutics as the introduction of nucleotide analogues, deemed necessary for in vivo stability, may effectively destroy the therapeutic capabilities of the molecule, particularly at the dosage of stabilizing nucleotide analogues necessary for sufficient in vivo stability. By the introduction of a discontinuous passenger strand, such as the discontinuous passenger strands according to the present invention, we have found that the antisense strand can tolerate considerably higher dosages of nucleotide analogues, such as LNA (see FIGS. 23, 24, & 25) and other nucleotide analogues, such as 2'-F-DNA) or 2'-O-Me-RNA. The advantage is seen even when the antisense strand has nucleotide analogues in the region upstream of the three 3' terminal nucleobase units of the antisense strand (typically the area least sensitive to nucleotide modifications). Indeed, in FIG. 24 we show that a antisense strand comprising only of nucleotide analogues, such as 2'-F-DNA or 2'-O-Me-RNA can, when paired with a discontinuous passenger strand, still provide a reasonable silencing effect on the target.

In one embodiment, the antisense strand comprises at least 1 nucleotide analogue which is outside of the three 3' terminal nucleobase residues of the antisense strand.

In one embodiment all the nucleobases of the antisense strand are nucleotide analogues, such as nucleotide analogues with a 2' substitution such as 2'-F-DNA or 2'-O-Me-RNA.

In one embodiment the antisense strand may comprise one of the following nucleobase motifs 5'-Xxx, 5'-XXx, 5'-xXx, 5'-xxX, 5'-XXX wherein x represents a RNA monomer, and X represents a nucleotide analogue unit, such as and LNA unit.

Suitably, the antisense strand may comprise 1, 2, 3, 4, 5, 6, 7, 8, 9, 10, 11, 12, 13, 14, 15, 16, 17, 18, 19, 20, 21, 22, 23 or 24 nucleotide analogues, such as an LNA monomer at a position from the 5' end selected from the group consisting of: position 1, position 2, position 3. position 4, position 5, position 6, position 7, position 8, position 9, position 11, position 13, position 14, position 15, position 16, position 17, position 18, position 19, position 20, position 21, position 22, position 23 or position 24. The antisense strand may comprise nucleotide analogues with the 3 prime over hang, such as in positions 1, 2, 3 form the 3' end, and/or within the duplex with the passenger strand. In one embodiment the 5' most monomer of the antisense strand is an RNA nucleotide. The passenger strand may comprise nucleotide analogues with the 3 prime over hang, such as in positions 1, 2, 3 form the 3' end, and/or within the duplex with the antisense strand.

In one embodiment, which may be the same or different the antisense strand comprises at least three nucleotide analogues, such as LNA units. Suitably at least one of the nucleotide analogue units is located outside of the three 3' terminal nucleobase monomers of the antisense strand, such as at least two of the nucleotide analogue units is located outside of the three 3' terminal nucleobase monomers of the antisense strand, such as at least 3, 4, 5, 6, 7, 8, 9, 10, 11, 12, 13, 14, 15, 16, 17, 18, 19, 20, 21, 22 of the nucleotide analogue units is located outside of the three 3' terminal nucleobase monomers of the antisense strand, such as between 1 and 10 of the nucleotide analogue units is located outside of the three 3' terminal nucleobase monomers of the antisense strand.

In one embodiment, the antisense strand comprises between 3 and 10 nucleotide analogues units, such as LNA monomers, such as between 4 and 6 nucleotide analogue monomers.

In a preferred embodiment, the antisense strand comprises one or more nucleotide analogues, such as LNA within the region of the antisense strand which forms a complementary duplex with the passenger strand.

In one embodiment the antisense strand may comprise a nucleobase motif 5'-xxXxxX.

In one embodiment the antisense strand may comprise one of the following nucleobase motifs 5'-Xxx, 5'-XXx, 5'-xXx, 5'-xxX, 5'-XXX wherein x represents a RNA monomer, and X represents a nucleotide analogue unit, such as and LNA unit.

In one embodiment the antisense strand may comprise one of the following nucleobase motifs 5'-xxxxX, 5'-xxxXx, 5'-xxXxx, 5'-xXxxx, 5'-Xxxxx, 5' xxxXX, 5' xxXXx, 5' xXXxx, 5' XXxxx, 5' xxxXx, 5' xXXXx, 5' XXXxx, 5' xXXXX, 5' XXXXX, 5' XxxxX, 5' XxxXx, 5' XxXxx, 5' XXxxx, 5' XXxxX, 5' XxxXX, 5' XXxXX, 5' XXXxX, 5' XXXXX, wherein x represents a RNA monomer, and X represents a nucleotide analogue unit, such as and LNA unit.

In one embodiment the antisense strand may comprise a sequence 5'xxXxxXxxxxXxxXxxxxxXXx3', wherein x represents a RNA monomer, and X represents a nucleotide analogue unit, such as and LNA unit.

In one embodiment at least one of the three 3' terminal nucleobases of the second RNA molecule of the passenger strands is a nucleotide analogue, such as LNA. In such an embodiment the 3' terminal nucleobases of the second RNA molecule of the passenger strand may comprise one of the following nucleobase motifs Xxx-3', XXx-3', xXx-3', xxX-3', XXX-3' wherein x represents a RNA monomer, and X represents a nucleotide analogue unit, such as and LNA unit. In this embodiment the second RNA molecule of the passenger strands may comprise further nucleotide analogue units, such as LNA units.

The Locked Nucleic Acid (LNA) used in the RNA complex according to the invention has the structure of the general formula Scheme 1

X and Y are independently selected among the groups —O—, —S—, —N(H)—, N(R)—, —CH$_2$— or —CH— (if part of a double bond), —CH$_2$—O—, —CH$_2$—S—, —CH$_2$—N(H)—, —CH$_2$—N(R)—, —CH$_2$—CH$_2$— or —CH$_2$—CH— (if part of a double bond), —CH=CH—, where R is selected form hydrogen and C$_{1-4}$-alkyl; Z and Z* are independently selected among an internucleotide linkage, a terminal group or a protecting group; B constitutes a natural or non-natural nucleobase; and the asymmetric groups may be found in either orientation.

Phosphorothioate linkages may be preferred. However, the molecules which form the RNA complex may comprise other linkages, or mixtures of different linkages—for example both phosphate and phosphorothioate linkages, or just phosphate linkages, or other linkages as disclosed herein.

The term "thio-LNA" comprises a locked nucleobase in which at least one of X or Y in Scheme 1 is selected from S or —CH$_2$—S—. Thio-LNA can be in both beta-D and alpha-L-configuration.

The term "amino-LNA" comprises a locked nucleobase in which at least one of X or Y in Scheme 1-N(H)—, N(R)—, CH$_2$—N(H)—, —CH$_2$—N(R)— where R is selected form hydrogen and C$_{1-4}$-alkyl. Amino-LNA can be in both beta-D and alpha-L-configuration.

The term "oxy-LNA" comprises a locked nucleotide in which at least one of X or Y in Scheme 21 represents —O— or —CH$_2$—O—. Oxy-LNA can be in both beta-D and alpha-L-configuration.

The term "ena-LNA" comprises a locked nucleotide in which Y in Scheme 1 is —CH$_2$—O— (where the (wherein the oxygen atom of —CH$_2$—O— is attached to the 2-position relative to the nucleobase B).

The term "alpha-L-LNA" comprises a locked nucleotide represented as shown in Scheme 2 (structure to the right).

The term "LNA derivatives" comprises all locked nucleotide in Scheme 1 as well as beta-D-methylene LNA, e.g. thio-LNA, amino-LNA, alpha-L-oxy-LNA and ena-LNA, except beta-D-oxy-LNA.

The term 'locked nucleotide' refers to a 'locked nucleobase', and is not used in the same context as the term 'nucleotide' as defined herein.

In Scheme 1, the 4 chiral centers are shown in a fixed configuration. However, the configurations in Scheme 1 are not necessarily fixed. Also comprised in this invention are compounds of the general Scheme 1 in which the chiral centers are found in different configurations, such as those represented in Scheme 2. Thus, the intention in the illustration of Scheme 1 is not to limit the configuration of the chiral centre. Each chiral center in Scheme 1 can exist in either R or S configuration. The definition of R (rectus) and S (sinister) are described in the IUPAC 1974 Recommendations, Section E, Fundamental Stereochemistry: The rules can be found in Pure Appl. Chem. 45, 13-30, (1976) and in "Nomenclature of organic Chemistry" pergamon, New York, 1979.

Z and Z* are independently selected among an internucleoside linkage, a terminal group or a protecting group The internucleoside linkage may be selected form the group consisting of: —O—P(O)$_2$—O—, —O—P(O,S)—O—, —O—P(S)$_2$—O—, —S—P(O)$_2$—O—, —S—P(O,S)—O—, —S—P(S)$_2$—O—, —O—P(O)$_2$—S—, —O—P(O,S)—S—, —S—P(O)$_2$—S—, —O—PO(R$^H$)—O—, O—PO(OCH$_3$)—O—, —O—PO(NR$^H$)—O—, —O—PO(OCH$_2$CH$_2$S—R)—O—, —O—PO(BH$_3$)—O—, —O—PO(NHR$^H$)—O—, —O—P(O)$_2$—NR$^H$—, —NR$^H$—P(O)$_2$—O—, —NR$^H$—CO—O—, —NR$^H$—CO—NR$^H$—, and/or the internucleoside linkage may be selected form the group consisting of: —O—CO—O—, —O—CO—NR$^H$—, —NR$^H$—CO—CH$_2$—, —O—CH$_2$—CO—NR$^H$—, —CH$_2$—CH$_2$—NR—, —CO—NR$^H$—CH$_2$—, —CH$_2$—NR$^H$—CO—, —O—CH$_2$—CH$_2$—S—, —S—CH$_2$—CH$_2$—O—, —S—CH$_2$—CH$_2$—S—, —CH$_2$—SO$_2$—CH$_2$—, —CH$_2$—CO—NR$^H$—, —O—CH$_2$—CH$_2$—NR$^H$—CO—, —CH$_2$—NCH$_3$—O—CH$_2$—, where R$^H$ is selected from hydrogen and C$_{1-4}$-alkyl, The terminal groups are selected independently among from hydrogen, azido, halogen, cyano, nitro, hydroxy, Prot-O—, Act-O—, mercapto, Prot-S—, Act-S—, C$_{1-6}$-alkylthio, amino, Prot-N(R$^H$)—, Act-N(R$^H$)—, mono- or di(C$_{1-6}$-alkyl) amino, optionally substituted C$_{1-6}$-alkoxy, optionally substituted C$_{1-6}$-alkyl, optionally substituted C$_{2-6}$-alkenyl, optionally substituted C$_{2-6}$-alkenyloxy, optionally substituted C$_{2-6}$-alkynyl, optionally substituted C$_{2-6}$-alkynyloxy, monophosphate, monothiophosphate, diphosphate, dithiophosphate triphosphate, trithiophosphate, DNA intercalators, photochemically active groups, thermochemically active groups, chelating groups, reporter groups, ligands, carboxy, sulphono, hydroxymethyl, Prot-O—CH$_2$—, Act-O—CH$_2$—, aminomethyl, Prot-N(R$^H$)—CH$_2$—, Act-N(R$^H$)—CH$_2$—, carboxymethyl, sulphonomethyl, where Prot is a protection group for —OH, —SH, and —NH(R$^H$), respectively, Act is an activation group for —OH, —SH, and —NH(R$^H$), respectively, and R$^H$ is selected from hydrogen and C$_{1-6}$-alkyl;

The protection groups of hydroxy substituents comprises substituted trityl, such as 4,4'-dimethoxytrityloxy (DMT), 4-monomethoxytrityloxy (MMT), and trityloxy, optionally substituted 9-(9-phenyl)xanthenyloxy (pixyl), optionally substituted methoxytetrahydro-pyranyloxy (mthp), silyloxy such as trimethylsilyloxy (TMS), triisopropylsilyloxy (TIPS), tert-butyldimethylsilyloxy (TBDMS), triethylsilyloxy, and phenyldimethylsilyloxy, tert-butylethers, acetals (including two hydroxy groups), acyloxy such as acetyl or halogen substituted acetyls, e.g. chloroacetyloxy or fluoroacetyloxy, isobutyryloxy, pivaloyloxy, benzoyloxy and substituted benzoyls, methoxymethyloxy (MOM), benzyl ethers or substituted benzyl ethers such as 2,6-dichlorobenzyloxy (2,6-Cl$_2$Bzl). Alternatively when Z or Z* is hydroxyl they may be protected by attachment to a solid support optionally through a linker.

In the embodiment above, Act designates an activation group for —OH, —SH, and —NH(R$^H$), respectively. Such activation groups are, e.g., selected from optionally substituted O-phosphoramidite, optionally substituted O-phosphotriester, optionally substituted O-phosphordiester, optionally substituted H-phosphonate, and optionally substituted O-phosphonate.

In the present context, the term "phosphoramidite" means a group of the formula —P(OR$^x$)—N(R$^y$)$_2$, wherein R$^x$ designates an optionally substituted alkyl group, e.g. methyl, 2-cyanoethyl, or benzyl, and each of R$^y$ designate optionally substituted alkyl groups, e.g. ethyl or isopropyl, or the group —N(R$^y$)$_2$ forms a morpholino group (—N(CH$_2$CH$_2$)$_2$O). R$^x$ preferably designates 2-cyanoethyl and the two R$^y$ are preferably identical and designate isopropyl. Thus, an especially relevant phosphoramidite is N,N-diisopropyl-O-(2-cyanoethyl)-phosphoramidite.

B constitutes a natural or non-natural nucleobase and selected among adenine, cytosine, 5-methylcytosine, isocytosine, pseudoisocytosine, guanine, thymine, uracil, 5-bromouracil, 5-propynyluracil, 5-propyny-6-fluorouracil, 5-methylthiazoleuracil, 6-aminopurine, 2-aminopurine, inosine, diaminopurine, 7-propyne-7-deazaadenine, 7-propyne-7-deazaguanine, and 2-chloro-6-aminopurine. In some embodiment, the Locked Nucleic Acid (LNA) used in the oligomeric compound of the invention comprises the nucleobases which are modified nucleobases selected from the group consisting of 5-methylcytosine, isocytosine, pseudoisocytosine, 5-bromouracil, 5-propynyluracil, 6-aminopurine, 2-aminopurine, inosine, diaminopurine, 2-chloro-6-aminopurine.

Preferably, the Locked Nucleic Acid (LNA) used in the oligomeric compound, such as an antisense oligonucleotide, of the invention comprises at least one nucleotide comprises a Locked Nucleic Acid (LNA) unit according any of the formulas Scheme 2

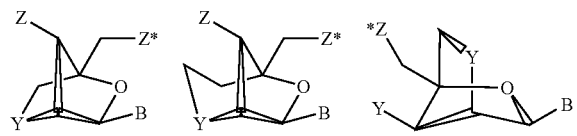

wherein Y is —O—, —S—, —NH—, or N(R$^H$); Z and Z* are independently selected among an Internucleoside linkage, a terminal group or a protecting group; and B constitutes a natural or non-natural nucleobase.

LNA monomers and their preparation are described in WO 99/14226 and subsequent applications, WO 00/56746, WO 00/56748, WO 00/66604, WO 00/125248, WO 02/28875, WO 2002/094250 and WO 2003/006475. One particular example of a thymidine LNA monomer is the (1S,3R,4R,7S)-7-hydroxy-1-hydroxymethyl-5-methyl-3-(thymin-1yl)-2,5-dioxa-bicyclo[2:2:1]heptane.

Specifically preferred LNA units are shown in Scheme 3 where B and Z* and Z are as previously defined, and wherein R$^H$ is selected from hydrogen and C$_{1-4}$-alkyl.

In one embodiment the nucleotide analogue is a pyrene 2'-amino-LNA monomer or a adamantly 2'-amino-LNA monomer.

As well as LNA monomers (eg alpha-L-LNA, thio-LNA, amino-LNA, ENA, other nucleotide analogues which may be used are those which either do not disrupt the A-form configuration of the sisiRNA complex, or those which actual encourage the A-form configuration. In one embodiment HNA—hexitol nucleic acids may be used, for example either as the only nucleotide analogue or in conjunction with LNA nucleotides.

In a preferred embodiment, the RNA complex comprises phosphorothioate linkages.

Preferred nucleotide analogues of the invention is nucleotide analogues selected from the group of 2'-O-alkyl-RNA monomers, 2'-amino-DNA monomers, 2'-fluoro-DNA monomers, LNA monomers, and INA monomers.

In one embodiment, the passenger strand, such as the first and/or second RNA molecules, comprises one or more LNA monomers (nucleotide analogues).

In one embodiment, the antisense strand comprises one or more LNA monomers (nucleotide analogues).

In one embodiment, the RNA complex of the invention has reduced off target effects as compared to native RNA complexes with a continuous passenger strand, as outlined earlier in the specification.

In another embodiment, the RNA complex of the invention produces a reduced immune response as compared to native RNA complexes with a continuous passenger strand.

In still another embodiment, the RNA complexes of the invention have a prolonged effect as compared to native RNA complexes with a continuous passenger strand. Accordingly, in a preferred embodiment, the effect of RNA complexes of the invention is effective for a longer period of time as compared to native RNA complexes with a continuous passenger strand.

In yet another embodiment, the RNA complexes of the invention have an increased effect as compared to native RNA complexes with a continuous passenger strand. Accordingly, in a preferred embodiment, the RNA complex mediate RNAi more effectively than the native RNA complex, e.g. by more efficient degradation of target mRNA or by more efficient translational inhibition of target mRNA.

Another aspect of the invention is a method of preparing the RNA complex of the invention comprising incubating the antisense strand with the passenger strand under conditions wherein a RNA complex comprising a core double stranded region is formed, said RNA complex being capable of mediating RNA interference of a corresponding cellular RNA.

Still another aspect of the invention is a method of mediating nucleic acid modification of a target nucleic acid in a cell or an organism comprising the steps:
  a. Contacting a cell or organism with the RNA complex of the invention under conditions wherein modification of a target nucleic acid can occur
  b. Thereby mediating modification of a target nucleic acid In an embodiment, the method of mediating nucleic acid modification of a target nucleic acid is performed in vitro (but still within a cell).

In an embodiment, the method of mediating nucleic acid modification of a target nucleic acid is performed in vivo (in an organism).

In yet another embodiment, the method is performed on an isolated cell.

In a preferred embodiment, the nucleic acid modification of the method is RNA interference, preferable degradation of target mRNA or translational inhibition of target mRNA or inhibition of other types of RNA, e.g. non-coding RNA.

In another embodiment, the nucleic acid modification is DNA methylation.

Another aspect of the invention is a method of examining the function of a gene in a cell or organism comprising:
a. Introducing a RNA complex of the invention that targets the RNA encoded by the gene, such as an mRNA or other functional RNA, for degradation or silencing, into the cell or organism, thereby producing a test cell or test organism, thereby producing a test cell or test organism
b. Maintaining the test cell or test organism under conditions under which degradation or silencing of the RNA encoded by the gene occurs, thereby producing a test cell or test organism in which RNA levels of the gene is reduced
c. Observing the phenotype of the test cell or organism produced in step b and optionally comparing the observed phenotype with the phenotype of an appropriate control cell or control organism, thereby providing information about the function of the gene.

The RNA complex of the invention can be introduced into cells e.g. using transfection, as outlined in the appended examples.

The phenotype of the organism or cell may be observed e.g. using proteomics to assess protein levels or using microarrays to assess mRNA levels. Also a more defined phenotype may be used, e.g. the expression of one particular gene.

The information obtained about the function of a gene may be used to determine whether a gene product is a suitable target for therapeutic intervention in relation to a particular disease. Thus, if it is demonstrated that a certain gene product act in a certain biochemical pathway known to be affected in e.g. a specific subtype of cancer, the gene product might be a suitable target for therapeutic intervention for treatment of the aforementioned subtype of cancer.

In a preferred embodiment of the method of examining the function of a gene in a cell or organism, the nucleic acid modifications of the method are RNA interference, preferable degradation of target mRNA or translational inhibition of target mRNA.

In another embodiment, modification of nucleic acid modifications is DNA methylation.

In preferred embodiments of the method of examining the function of a gene in a cell or organism, the method is performed in vitro.

In yet another embodiment, the method is performed on an isolated cell.

Another aspect of the invention is a method of assessing whether an agent acts on a gene product comprising the steps:
a. Introducing the RNA complex of the invention corresponding to said gene into a cell or organism, thereby producing a test cell or test organism
b. Maintaining the test cell or test organism under conditions under which modification of a target nucleic acid occurs
c. Introducing the agent into the test cell or test organism
d. Observing the phenotype of the test cell or organism produced in step c and optionally comparing the observed phenotype with the phenotype of an appropriate control cell or control organism, thereby providing information about whether the agent acts on the gene product A preferred control in step d is a test cell or test organism that has not had the RNA complex of step a introduced.

In a preferred embodiment of the method of assessing whether an agent acts on a gene or gene product, the nucleic acid modifications of the method are RNA interference, preferable degradation of target mRNA or translational inhibition of target mRNA. In another embodiment, modification of nucleic acid modifications is DNA methylation.

In yet another embodiment, the method is performed on an isolated cell.

In a further aspect the invention provides for a method of preparing an RNA complex comprising incubating an antisense strand as described herein with the at least two RNA molecules which form a discontinuous passenger strand as described herein, and optionally further RNA molecules of the passenger strand as described herein, under conditions wherein a RNA complex comprising a core double stranded region is formed. Suitably, said RNA complex is capable of mediating RNA interference of a corresponding cellular RNA.

In a further aspect the invention provides for a method of preparing a pharmaceutical composition comprising an RNA complex comprising incubating an antisense strand as described herein with the at least two RNA molecules which form a discontinuous passenger strand as described herein, and optionally further RNA molecules of the passenger strand as described herein, under conditions wherein a RNA complex comprising a core double stranded region is formed, said RNA complex being capable of mediating RNA interference of a corresponding cellular RNA, wherein either said incubation occurs within a pharmaceutically acceptable diluent, carrier, or adjuvant, or said RNA complex is subsequently admixed with a pharmaceutically acceptable diluent, carrier, or adjuvant.

The invention provides for the use of a RNA complex as defined herein as a medicament.

The invention provides for the use of a RNA complex as defined herein as a medicament for the treatment of cancer.

The invention provides for the use of a RNA complex as defined in herein for the manufacture of a medicament for the treatment of cancer, The invention provides for a method for treating a patient, said method comprising administering the pharmaceutical composition according to the invention to a patient in need thereof. Such a method may be for the treatment of cancer (e.g. by targeting p21 ras, such as H-ras).

Still another aspect of the invention is the RNA complex and a pharmaceutically acceptable diluent, carrier or adjuvant (i.e. the invention refers to a pharmaceutical composition or a therapeutic composition comprising the RNA complex according to the invention). It will be apparent to the skilled man that the RNA complexes of the invention can be designed to target specific genes and gene products. It is to be understood that the RNA complexes will target a DNA sequence or a RNA sequence, and not a protein. However, the level of a gene product such as a protein may be affected indirectly, if its mRNA is modified e.g. by mRNA degradation or translational inhibition. Also the expression of the gene encoding the protein may be affected, e.g. because of DNA methylation.

Thus, another aspect is the RNA complex of the invention for use as a medicament. Once a therapeutic target has been validated, the skilled man can design RNA complexes that affect the level and the activity of the target, because the specificity of the RNA complexes lies exclusively within the sequence of the antisense strand. For native RNA complexes with a continuous passenger strand, there remains a problem with off-target effects due to the passenger strand acting as a guide sequence.

Pharmaceutical Composition

Directions for the preparation of pharmaceutical compositions can be found in "Remington: The Science and Practice of Pharmacy" by Alfonso R. Gennaro, and in the following.

Preferably, the compound of the invention is included in a unit formulation such as in a pharmaceutically acceptable carrier or diluent in an amount sufficient to deliver to a patient a therapeutically effective amount without causing serious side effects in the treated patient. However, in some forms of therapy, serious side effects may be acceptable in terms of ensuring a positive outcome to the therapeutic treatment.

The dosage of the pharmaceutical composition is dependent on severity and responsiveness of the disease state to be treated, and the course of treatment lasting from several days to several months, or until a cure is effected or a diminution of the disease state is achieved. Optimal dosing schedules can be calculated from measurements of drug accumulation in the body of the patient. Optimum dosages may vary depending on the relative potency of individual oligonucleotides. Generally it can be estimated based on $EC_{50}$s found to be effective in in vitro and in vivo animal models. In general, dosage is from 0.01 µg to 1 g per kg of body weight, and may be given once or more daily, weekly, monthly or yearly, or even once every 2 to 10 years or by continuous infusion for hours up to several months. The repetition rates for dosing can be estimated based on measured residence times and concentrations of the drug in bodily fluids or tissues. Following successful treatment, it may be desirable to have the patient undergo maintenance therapy to prevent the recurrence of the disease state.

The formulated drug may comprise pharmaceutically acceptable binding agents and adjuvants. Capsules, tablets and pills etc. may contain for example the following compounds: microcrystalline cellulose, gum or gelatin as binders; starch or lactose as excipients; stearates as lubricants; various sweetening or flavouring agents. For capsules the dosage unit may contain a liquid carrier like fatty oils. Likewise coatings of sugar or enteric agents may be part of the dosage unit. The oligonucleotide formulations may also be emulsions of the active pharmaceutical ingredients and a lipid forming a micellular emulsion.

The pharmaceutical compositions of the present invention may be administered in a number of ways depending upon whether local or systemic treatment is desired and upon the area to be treated. Administration may be (a) oral (b) pulmonary, e.g., by inhalation or insufflation of powders or aerosols, including by nebulizer; intratracheal, intranasal, (c) topical including epidermal, transdermal, ophthalmic and to mucous membranes including vaginal and rectal delivery; or (d) parenteral including intravenous, intraarterial, subcutaneous, intraperitoneal or intramuscular injection or infusion; or intracranial, e.g., intrathecal or intraventricular, administration. In one embodiment the active oligo is administered IV, IP, orally, topically or as a bolus injection or administered directly in to the target organ.

Pharmaceutical compositions and formulations for topical administration may include transdermal patches, ointments, lotions, creams, gels, drops, sprays, suppositories, liquids and powders. Conventional pharmaceutical carriers, aqueous, powder or oily bases, thickeners and the like may be necessary or desirable. Preferred topical formulations include those in which the oligonucleotides of the invention are in admixture with a topical delivery agent such as lipids, liposomes, fatty acids, fatty acid esters, steroids, chelating agents and surfactants. Compositions and formulations for oral administration include but is not restricted to powders or granules, microparticulates, nanoparticulates, suspensions or solutions in water or non-aqueous media, capsules, gel capsules, sachets, tablets or minitablets. Compositions and formulations for parenteral, intrathecal or intraventricular administration may include sterile aqueous solutions which may also contain buffers, diluents and other suitable additives such as, but not limited to, penetration enhancers, carrier compounds and other pharmaceutically acceptable carriers or excipients.

Pharmaceutical compositions of the present invention include, but are not limited to, solutions, emulsions, and liposome-containing formulations. These compositions may be generated from a variety of components that include, but are not limited to, preformed liquids, self-emulsifying solids and self-emulsifying semisolids. Delivery of drug to tumour tissue may be enhanced by carrier-mediated delivery including, but not limited to, cationic liposomes, cyclodextrins, porphyrin derivatives, branched chain dendrimers, polyethylenimine polymers, nanoparticles and microspheres (Dass C R. J Pharm Pharmacol 2002; 54(1):3-27). The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient(s). In general the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels and suppositories. The compositions of the present invention may also be formulated as suspensions in aqueous, non-aqueous or mixed media. Aqueous suspensions may further contain substances, which increase the viscosity of the suspension including, for example, sodium carboxymethylcellulose, sorbitol and/or dextran. The suspension may also contain stabilizers.

For parenteral, subcutaneous, intradermal or topical administration the formulation may include a sterile diluent, buffers, regulators of tonicity and antibacterials. The active compound may be prepared with carriers that protect against degradation or immediate elimination from the body, including implants or microcapsules with controlled release properties. For intravenous administration the preferred carriers are physiological saline or phosphate buffered saline.

An RNA complex of the invention may be mixed with any material that do not impair the desired action, or with material that supplement the desired action. These could include other drugs including other nucleoside compounds.

Optionally, the pharmaceutical according to the invention comprises therapeutic agents, such as further antisense compounds, chemotherapeutic compounds, anti-inflammatory compounds, antiviral compounds and/or immuno-modulating compounds. Anti-inflammatory drugs, including but not limited to nonsteroidal anti-inflammatory drugs and corticosteroids, antiviral drugs, and immuno-modulating drugs may also be combined in compositions of the invention.

Two or more combined compounds may be used together or sequentially, i.e. the compound (RNA complex) according to the invention may be used prior to, during or subsequent to one or more of the other therapeutic agents referred to herein.

Oligonucleotides used in the RNA complexes according to the invention may also be conjugated to active drug substances, for example, aspirin, ibuprofen, a sulfa drug, an antidiabetic, an antibacterial or an antibiotic.

In one embodiment, the pharmaceutical composition according to the invention further comprises at least one chemotherapeutic agent. Said chemotherapeutic agent is preferably selected from the group consisting of adrenocorticosteroids, such as prednisone, dexamethasone or decadron; altretamine (hexylen, hexamethylmelamine (HMM)); amifostine (ethyol); aminoglutethimide (cytadren); amsacrine (M-AMSA); anastrozole (arimidex); androgens, such as testosterone; asparaginase (elspar); bacillus calmette-gurin; bicalutamide (casodex); bleomycin (blenoxane); busulfan (myleran); carboplatin (parapiatin); carmustine (BCNU, BICNU); chlorambucil (leukeran); chlorodeoxyadenosine (2-CDA, cladribine, leustatin); cisplatin (platinol); cytosine arabinoside (cytarabine); dacarbazine (DTIC); dactinomycin (actinomycin-D, cosmegen); daunorubicin (cerubidine); docetaxel (taxotere); doxorubicin (adriomycin); epirubicin; estramustine (emcyt); estrogens, such as diethylstilbestrol (DES); etopside (VP-16, VePesid, etopophos); fludarabine (fludara); flutamide (eulexin); 5-FUDR (floxuridine); 5-fluorouracil (5-FU); gemcitabine (gemzar); goserelin (zodalex); herceptin (trastuzumab); hydroxyurea (hydrea); Idarubicin (idamycin); ifosfamide; IL-2 (proleukin, aldesleukin); interferon alpha (Intron A, roferon A); irinotecan (camptosar); leuprolide (lupron); levamisole (ergamisole); lomustine (CCNU); mechlorathamine (mustargen, nitrogen mustard); melphalan (alkeran); mercaptopurine (purinethol, 6-MP); methotrexate (mexate); mitomycin-C (mutamucin); mitoxantrone (novantrone); octreotide (sandostatin); pentostatin (2-deoxycoformycin, nipent); plicamycin (mithramycin, mithracin); prorocarbazine (matulane); streptozocin; tamoxifin (nolvadex); taxol (paclitaxel); teniposide (vumon, VM-26); thiotepa; topotecan (hycamtin); tretinoin (vesanoid, all-trans retinoic acid); vinblastine (valban); vincristine (oncovin) and vinorelbine (navelbine).

In a certain embodiments, the present invention provides pharmaceutical compositions containing (a) one or more RNA complexes as described herein and (b) one or more other chemotherapeutic agents which function by a non-antisense mechanism. When used with the compounds (RNA complexes) of the invention, such chemotherapeutic agents may be used individually (e.g. mithramycin and oligonucleotide), sequentially (e.g. mithramycin and oligonucleotide for a period of time followed by another agent and oligonucleotide), or in combination with one or more other such chemotherapeutic agents or in combination with radiotherapy. All chemotherapeutic agents known to a person skilled in the art are here incorporated as combination treatments with compound according to the invention.

In another embodiment, compositions of the invention may contain one or more RNA complexes targeted to a first nucleic acid and one or more additional compounds, such as antisense oligonucleotides targeted to a second nucleic acid target. Two or more combined compounds may be used together or sequentially. i.e. the compound according to the invention may be used prior to, during or subsequent to one or more of the other therapeutic agents referred to herein.

The pharmaceutical composition of the invention may constitute a pro-drug. Therefore, in one embodiment of the invention the RNA complex of the invention may be in the form of a pro-drug. Oligonucleotides are by virtue negatively charged ions. Due to the lipophilic nature of cell membranes the cellular uptake of oligonucleotides are reduced compared to neutral or lipophilic equivalents. This polarity "hindrance" can be avoided by using the pro-drug approach (see e.g. Crooke, R. M. (1998) In Crooke, S. T. *Antisense research and Application*. Springer-Verlag, Berlin, Germany, vol. 131, pp. 103-140). In this approach the oligonucleotides are prepared in a protected manner so that the oligo is neutral when it is administered. These protection groups are designed in such a way that so they can be removed then the oligo is taken up be the cells. Examples of such protection groups are S-acetylthioethyl (SATE) or S-pivaloylthloethyl (t-butyl-SATE). These protection groups are nuclease resistant and are selectively removed intracellulary.

Preferably the pharmaceutical composition of the invention further comprises anti-inflamatory compounds and/or antiviral compounds.

The invention described herein encompasses a method of preventing or treating cancer comprising administering a therapeutically effective amount of the pharmaceutical composition or RNA complex of the invention.

Conjugates

In one embodiment of the invention, one or more of the oligonucleotides which form the RNA complex may be linked to ligands/conjugates, which may be used, e.g. to increase the cellular uptake of RNA complex. This conjugation can take place at the terminal positions 5'/3'-OH but the ligands may also take place at the sugars and/or the bases. As the RNA complex according to the invention typically comprises more terminals (due to the discontinuous passenger strand), there are more sites which to conjugate moieties which enhance chemical uptake.

In a preferred embodiment, at least one of the molecules which form the RNA complex, preferably the first, second and/or further RNA molecules that form the passenger strand are conjugated with a moiety which improvise the in vivo uptake of the RNA complex, such as cholesterol (See Soutschek et al., Nature 432 (11) pp 173-178).

In one embodiment, the growth factor to which the oligonucleotide may be conjugated, may comprise transferrin or folate. Transferrin-polylysine-oligonucleotide complexes or folate-polylysine-oligonucleotide complexes may be prepared for uptake by cells expressing high levels of transferrin or folate receptor. Other examples of conjugates/ligands are cholesterol moieties, duplex intercalators such as acridine, poly-L-lysine, "end-capping" with one or more nuclease-resistant linkage groups such as phosphoromonothioate, and the like.

The invention also provides for a conjugate comprising the RNA complex according to the invention as herein described, and at least one non-nucleotide or non-polynucleotide moiety covalently attached to said complex.

In a preferred embodiment the pharmaceutical composition according to the invention comprises a nucleic acid delivery agent, i.e. an agent which enhances update and distribution of the therapeutic agent within the body. Preferred delivery agents include chitosan, which is known to be a very good agent which binds nucleic acids, with low toxicity and is typically well tolerated in the body. It is thought to minimise the charge of the nucleotide thereby allowing better uptake. An alternative delivery agent which may be used, optionally with other agents, such as chitosan, include polyethyleneimine. As such formulations of the RNA complex and delivery ganets are a preferred embodiment of the invention. Such embodiments may be combined with the conjugation embodiments above, for example incorporation of a terminal, such as by the incorporation of a 3' terminal cholesterol conjugated nucleobase during oligonucleotide synthesis.

Suitable Therapeutic Targets

The following are only by way of example.

ApoB: As described in WO 2007/031081, the Apo B mRNA is a suitable target for therapeutic Intervention, for example for the treatment of for example atherosclerosis, hypercholesterolemia or hyperlipidemia.

Survivin: As described in WO 2006/050732, the survivn mRNA is a suitable target for therapeutic intervention, for example for the treatment of, for example cancer. Hif-1alpha: As described in WO 2006/050734, the Hif-1alpha mRNA is a suitable target for therapeutic intervention for example, for the treatment of, for example cancer diseases, inflammatory diseases and eye diseases, such as cancer: multiple myeloma, renal cancer, cervical cancer, colon cancer, brain cancer, and breast cancer multiple myeloma, renal cancer, cervical cancer, colon cancer, brain cancer, and breast cancer, other: artherosclerosis, psoriasis, diabetic retinopathy, macular degeneration, rheumatoid arthritis, asthma, inflammatory bowel disease, warts, allergic dermatitis, inflammation, and skin inflammation Bcl2: As described in WO 2005/061710, the Bcl2 mRNA is a suitable target for therapeutic intervention, for example for the treatment of, for example cancer, such as a cancer selected from the group consisting of acute myelocytic leukemia, diffuse B-cell lymphoma, acute lymphocytic leukemia, hepatic cancer, renal cancer, urinary tract cancer, and colorectal cancer.

P21-Ras: As described in PCT/DK2006/000512, the mRNAs of p21 ras, such as K-ras, Ha-ras and N-ras are suitable targets for therapeutic intervention, for example for the treatment of cancer, such as solid tumors, carcinoma, sarcoma, or glioma.

In the way of example the above targets and conditions may be targeted using the pharmaceutical compositions according to the invention.

Further embodiments which may be combined with the other embodiments of the invention disclosed herein:

1. An RNA complex capable of mediating nucleic acid modifications of a target nucleic acid to which it corresponds, comprising a core double-stranded region, said core double stranded region comprising an antisense strand and a discontinuous passenger strand, that is hybridised to the antisense strand.
2. An RNA complex according to claim 1, wherein said nucleic acid modification is selected from the group of RNA Interference and DNA methylation.
3. An RNA complex according to embodiment 2, wherein RNA interference mediate degradation of a target RNA or translational inhibition of a target RNA or a combination of both.
4. An RNA complex according to embodiment 1, wherein the core double-stranded region comprises a number of base pairs between 15 and 40.
5. An RNA complex according to embodiment 4, wherein the core double-stranded region comprises a number of base pairs selected from the group of 18 base pairs, 19 base pairs, 20 base pairs, 21 base pairs, 22 base pairs and 23 base pairs.
6. An RNA complex according to any of embodiments 1-5 comprising an overhang.
7. An RNA complex according to embodiment 6 comprising two overhangs.
8. An RNA complex according to any of embodiments 6 and 7, wherein the antisense strand comprises a 3'-overhang.
9. An RNA complex according any of embodiments 6 and 7, wherein the passenger strand comprises a 3'-overhang.
10. An RNA complex according to any of embodiments 6-9, wherein the length of the overhang is between 1 and 8 nucleotides.
11. An RNA complex according to embodiment 10, wherein the length of the overhang is selected from the group of overhangs with a length of 1 nucleotide, 2 nucleotides and 3 nucleotides.
12. An RNA complex according to any of embodiments 1-6, comprising at least one blunt end.
13. An RNA complex according to any of embodiments 1-5, wherein the RNA complex is blunt ended in both ends.
14. An RNA complex according to any of embodiments 1-5, wherein the core double-stranded region comprises 18-22 base pairs, and wherein the antisense strand and the passenger strand each comprise a 3'-overhang of 1-3 nucleotides.
15. An RNA complex according to any of the preceding embodiments, wherein the discontinuous passenger strand comprises a first and a second RNA-molecule, which together forms the discontinuous passenger strand, wherein the first RNA molecule is hybridised to the downstream part of the antisense strand and the second RNA molecule is hybridised to the upstream part of the antisense strand.
16. An RNA complex according to embodiment 15, wherein the first and second RNA molecule is separated by a nick.
17. An RNA complex according to embodiment 15, wherein the first and second RNA molecule is separated by a gap, selected from the group of: a 1 nucleotide gap, a 2 nucleotide gap, a 3 nucleotide gap, a 4 nucleotide gap, a 5-nucleotide gap, a 6-nucleotide gap, a 7-nucleotide gap, an 8-nucleotide gap, a 9-nucleotide gap, a 10-nucleotide gap, an 11-nucleotide gap and a 12-nucleotide gap.
18. An RNA complex according to embodiments 15-17, wherein the first RNA molecule is connected to the antisense strand by a linker.
19. An RNA complex according to embodiments 15-17, wherein the second RNA molecule is connected to the antisense strand by linker.
20. An RNA complex according to embodiments 18 and 19, wherein the first RNA molecule is connected to the antisense strand by a first linker and the second RNA molecule is connected to the antisense strand by a second linker.
21. An RNA complex according to any of embodiments 15-20, wherein the first and the second RNA molecule is connected by a linker.
22. An RNA complex according to any of embodiments 15-21, wherein a linker is not a single stranded RNA linker.
23. An RNA complex according to embodiment 15, wherein the first and the second RNA molecule are not linked such that the RNA complex comprises three individual RNA molecules, namely the antisense strand, and the first and the second RNA molecule which together form the discontinued passenger strand.
24. An RNA complex according to any of embodiments 15-23, wherein the discontinued passenger strand has a discontinuity at a position selected from the group of: position 3, position 4, position 5, position 6, position, position 7, position 8, position 9, position 10, position 11, position 12, position 13, position 14, position 15, position 16, position 17, position 18, position 19, position 20, position 21, position 22, position 23, position 24, position 25, wherein the position is calculated in the 5' to 3' direction from the first nucleotide of the passenger strand base paired to the antisense strand in the of the passenger strand.

25. An RNA complex according to any of the preceding embodiments, wherein 5-ends of the complex are phosphorylated or available for phosphorylation.
26. An RNA complex according to embodiment 15, wherein the first RNA molecule comprises a 5'-end phosphate group and a 3'-end hydroxy group.
27. An RNA complex according to embodiment 15, wherein the second RNA molecule comprises a 5'-end phosphate group and a 3'-end hydroxy group.
28. An RNA complex according to any of the preceding embodiments, wherein the RNA complex comprises nucleotide analogues.
29. An RNA complex according to embodiment 28, wherein the antisense strand comprises nucleotide analogues.
30. An RNA complex according to embodiment 28, wherein the passenger strand comprises nucleotide analogues.
31. An RNA complex according to embodiments 28-30, wherein the first and the second RNA molecule of the passenger strand comprise nucleotide analogues.
32. An RNA complex according to any of embodiments 28-31, wherein nucleotide analogues are selected from the group of 2'-O-alkyl-RNA monomers, 2'-amino-DNA monomers, 2'-fluoro-DNA monomers, LNA monomers, PNA monomers, INA monomers.
33. An RNA complex according to any of embodiments 1-32, which has reduced off-target effects as compared to a native RNA complex comprising a non-modular passenger strand.
34. An RNA complex according to any of embodiments 1-32, which produce a reduced immune response as compared to a native RNA complex comprising a non-modular passenger strand.
35. An RNA complex according any of embodiments 1-32, which have a prolonged effect on target nucleic acids as compared to an RNA complex comprising a non-modular passenger strand.
36. An RNA complex according to any of embodiments 1-32, which have an increased effect on its target nucleic acid as to compared to an RNA complex comprising a non-modular passenger strand.
37. A method of preparing an RNA complex according to any one of embodiments 1-36 comprising incubating the antisense strand with the passenger strand under conditions wherein a RNA complex comprising a core double stranded region is formed, said RNA complex being capable of mediating RNA interference of a corresponding cellular RNA.
38. A method of mediating nucleic acid modifications of a target nucleic acid in a cell or an organism comprising the steps:
    a. Contacting said cell or organism with the RNA complex of any of embodiments 1-36 under conditions wherein target specific nucleic acid modifications can occur
    b. Thereby mediating a target specific nucleic acid modification guided by the antisense strand of the RNA complex.
39. A method according to embodiment 38, said method being performed in vitro.
40. A method according to embodiment 39, said method being performed on an isolated cell.
41. A method of examining the function of a gene in a cell or organism comprising:
    a. Introducing an RNA complex of any of embodiments 1-36 that targets mRNA for degradation into the cell or organism, thereby producing a test cell or test organism
    b. Maintaining the test cell or test organism under conditions under which degradation of mRNA of the gene occurs, thereby producing a test cell or test organism in which mRNA levels of the gene is reduced
    c. Observing the phenotype of the test cell or organism produced in step b and optionally comparing the observed phenotype with the phenotype of an appropriate control cell or control organism, thereby providing information about the function of the gene.
42. A method according to embodiment 41, used for determination of whether a gene product is a suitable target for therapeutic intervention.
43. A method according to embodiments 41 and 42, said method being performed in vitro.
44. A method according to embodiment 43, said method being performed on an isolated cell.
45. A method of assessing whether an agent acts on a gene product comprising the steps:
    a. Introducing an RNA complex of any of embodiments 1-36 that targets mRNA for degradation into the cell or organism, thereby producing a test cell or test organism
    b. Maintaining the test cell or test organism under conditions under which degradation of mRNA of the gene occurs, thereby producing a test cell or test organism in which mRNA levels of the gene is reduced
    c. Introducing the agent into the test cell or test organism
    d. Observing the phenotype of the test cell or organism produced in step c and optionally comparing the observed phenotype with the phenotype of an appropriate control cell or control organism, thereby providing information about whether the agent acts on the gene product
46. A method according to any of embodiments 45, said method being performed in vitro.
47. A method according to embodiment 46, said method being performed on an isolated cell.
48. A pharmaceutical composition comprising the RNA complex of embodiment 1-36 and a pharmaceutically acceptable diluent, carrier or adjuvant
49. The RNA complex of any of embodiments 1-36 for use as a medicament
50. Use of the RNA complex of any of embodiments 1-36 for mediating nucleic acid modification of a target nucleic acid to which it corresponds.
51. Use according to embodiment 50, wherein said nucleic acid modification is selected from the group of RNA interference and DNA methylation.
52. Use according to embodiment 51, wherein RNA interference mediate degradation of target RNA or translational inhibition of target RNA or a combination of both.
53. Use according to any of embodiments 50-52 with reduced off target effects.
54. Use according to any of embodiments 50-52 with a reduced interferon response.
55. Use of the RNA complex of any of embodiments 1-36 for diagnosis or prognosis

EXAMPLES

Experimentals

LNA oligonucleotides can be made and purified according to the methods disclosed or referenced in PCT/DK2006/000512 or WO2005/073378.

Oligonucleotides were synthesised using standard techniques for RNA synthesis and LNA synthesis.

LNA is an oligonucleotide containing one or more 2'-O,4'-C-methylene-linked ribonucleotides (LNA nucleotides) [M. Petersen; 1. Wengel, Trends Biotechnol. 2003, 21, 74-81].

LNA modified RNA is an RNA strand containing one or more 2'-O,4'-C-methylene-linked ribonucleotides (LNA nucleotides).

LNA modified siRNA (siLNA) is an siRNA construct containing one or more 2'-O,4'-C-methylene-linked ribonucleotides (LNA nucleotides).

Constructs

The human lung cancer cell line H1299 produced to stably express EGFP (EGFP half-life 2 h) was a gift from Dr Anne Chauchereau (CNRS, Villejuif, France). The two reporter constructs, The pISO$_{antisense-target}$ and pISO$_{sense-target}$, were constructed by annealing equimolar amounts of the following DNA oligos 5'-GCGACGTAAACGGCCACAAGTTC-3' (SEQ ID NO 29) and 3-TCGACGCTGCATTTGCCGGTGT-TCAAGGATC-5' (SEQ ID NO 30) (antisense target) or 5'-CTAGGCGACGTAAACGGCCACAAGTTCAGCT-3 (SEQ ID NO 31) and 3'-CGCTGCATTTGCCGGTGT-TCAAG-5'-(SEQ ID NO 32) (sense target) into SacI/NheI digested pSO (kindly provided by David Bartel) (Lewis, B. P. et al., (2003) Cell, 115, 787-798.) downstream of the firefly luciferase coding sequence.

Oligonucleotide Preparation

LNA-modified RNA oligos were prepared on an automated DNA synthesizer as described earlier (Singh, S. K. and Wengel, 3 (1988) Chem. Commun. 1247-8.

Synthesis of the derivatives Nu-2 (via Nu-1) to allow incorporation into RNA of the adamantly amino-LNA monomer aT (FIG. 18) on an automated synthesizer using amidite Nu-2 and conventional methods as described in the literature (Singh, S. K. and Wengel, J (1988) Chem. Commun. 1247-8.

A) Synthesis of (1R,3R,4R,7S)-1-(4,4'-Dimethoxytrityloxymethyl)-7-hydroxy-5-(1-adamantylmethylcarbonyl)-3-(thymin-1-yl)-2-oxa-5-azabicyclo[2.2.1]heptane (Nu-1). N-acylation of the starting nucleoside (572 mg, 1.0 mmol) (Nucleoside 3f" In Sørensen, M. D., Petersen, M. and Wengel, J. (2003) Chem. Commun. 2130-1) with 1-adamantane acetic acid (233 mg, 1.2 mmol) was carried out in the presence of EDC.HCl (230 mg, 1.2 mmol) in anhydrous CH$_2$Cl$_2$ (10 mL).

After stirring at room temperature until completion (~6 h), the reaction mixture was diluted with CH$_2$Cl$_2$, washed with sat aq. NaHCO$_3$ (two times) and the combined organic phases were dried (Na$_2$SO$_4$), filtered and concentrated to dryness under reduced pressure. The residue obtained after work-up procedure was purified by column chromatography (80-95% EtOAc in light petroleum, v/v) to afford a rotameric mixture (~1:1 by $^1$H NMR) of nucleoside Nu-1 (680 mg, 91%) as a white solid material. $^1$H NMR (CDCl$_3$) δ 7.66 (s, 1H), 7.63 (s, 1H), 7.48-7.44 (m, 4H), 7.37-7.20 (m, 14H), 6.85-6.81 (m, 8H), 5.53 (s, 1H), 5.44 (s, 1H), 5.14 (s, 1H), 4.65 (s, 1H), 4.35 (s, 2H), 3.77 (s, 12H), 3.61-3.42 (m, 8H), 2.29 (d, J=13.8 Hz, 1H), 2.18 (d, J=13.9 Hz, 1H), 1.97 (d, J=5.6 Hz, 1H), 1.93-1.89 (m, 9H), 1.73-1.60 (m, 28H); $^{13}$C NMR (CDCl$_3$) δ 171.4, 171.3, 164.7, 164.5, 158.7, 158.6, 150.3, 149.8, 144.5, 135.6, 135.5, 135.4, 135.3, 135.1, 134.9, 130.2, 130.1, 128.2, 128.0, 127.1, 113.4, 110.3, 110.0, 88.9, 88.1, 87.5, 87.2, 86.7, 70.2, 68.6, 64.4, 61.6, 59.6, 59.3, 55.2, 53.5, 51.3, 47.6, 47.4, 42.8, 37.1, 36.8, 36.7, 33.8, 33.5, 28.9, 28.7, 28.6, 12.6; MALDI-HRMS: m/z 770.3396 ([M+Na]$^+$, C$_{44}$H$_{49}$N$_3$O$_8$Na$^+$ calcd 770.3417).

B. Synthesis of (1R,3R,4R,7S)-7-(2-Cyanoethoxy(diisopropylamino)phosphinoxy)-1-(4,4'-dimethoxytrityloxymethyl)-5-(1-adamantylmethylcarbonyl)-3-(thymin-1-yl)-2-oxa-5-azabicyclo[2.2.1]heptane (Nu-2). 2-Cyanoethyl N,N-diisopropylphosphoramidochloridite (247 mg, 1.04 mmol) was added dropwise to a stirred solution of nucleoside Nu-1 (650 mg, 0.87 mmol) and N,N-(diisopropyl)ethylamine (1.0 mL) in anhydrous CH$_2$Cl$_2$ (10 mL). After stirring for 14 h at room temperature the reaction mixture was diluted with CH$_2$Cl$_2$ (50 mL). The organic phase was washed with sat. aq. NaHCO$_3$ (2×50 mL), dried (Na$_2$SO$_4$), filtered and concentrated under reduced pressure. The residue obtained was purified by column chromatography (50-60% EtOAc in n-hexane, v/v) to give nucleoside amidite Nu-2 (685 mg, 83%) as a white foam. $^{31}$P NMR (CDCl$_3$) δ 151.1, 151.0, 150.7, 149.4; MALDI-HRMS: m/z 970.4457 ([M+Na]$^+$, C$_{53}$H$_{66}$N$_5$O$_9$PNa$^+$ calcd 970.4496).

Incorporation into RNA of the pyrenyl amino-LNA monomer pT (FIG. 18) on an automated synthesizer was performed as described in the literature (Sørensen, M. D., Petersen, M. and Wengel, J. (2003) Chem. Commun. 2130-1).

Oligonucleotides applied in this study:

```
siRNA controls:
eGFPsiRNA
SEQ ID NO:1                       5'-GACGUAAACGGCCACAAGUUC
SEQ ID NO:2                       3'-CGCUGCAUUUGCCGGUGUUCA siRNA-mismatch
SEQ ID NO:3                       5'-GACUUAGACUGACACAAGUUC
SEQ ID NO:4                       3'-CGCUGAAUCUGACUGUGUUC SiRNA-BCR-ABL
SEQ ID NO:5                       5'-GCAGAGUUCAAAAGCCCUUUU
SEQ ID NO:6                       3'-UUCGUCUCAAGUUUUCGGGAA Sense oligonucleotides:
SEQ ID NO:7, also termed W004:    5'-GAC^{MeL}GUAAAC^{MeL}G
SEQ ID NO:8, also termed W005:    5'-GCC^{MeL}AC^{MeL}AAGUT^LC^{MeL}U
SEQ ID NO:9, also termed W037:    5'-GAC^{MeL}GUAAAC^{MeL}GGCC^{MeL}AC^{MeL}AAGUT^LC^{MeL}U
SEQ ID NO:10, also termed JW1106: 5'-GAC^{MeL}GUAAAC^{MeL}GGCCAC^{MeL}AAGUT^LC^{MeL}U
SEQ ID NO:11, also termed W034:   5'-GAC^{MeL}GUAAAC^{MeL}GG
SEQ ID NO:12, also termed W035:   5'-C C^{MeL}AC^{MeL}AAGUT^LC^{MeL} U
SEQ ID NO:13, also termed W036:   5'-GC C^{MeL}AC^{MeL}AAGUT^LC
SEQ ID NO:14, also termed W040:   5'-GACGUAAACG
SEQ ID NO:15, also termed W041:   5'-GCCACAAGUUCU
SEQ ID NO:17, also termed JW1105: 5'-GA^LCG^LUAAACGGCCACAAGUT^LC^{MeL}U Antisense oligonucleotides
SEQ ID NO:16, also termed JW1103: 5'-ACUUGUGGCCGUUUACGUCG^LC^{MeL}U
SEQ ID NO:18, also termed W010:   5'-ACT^LUGT^LGGCCGUUT^LACGT^LCG^LC^{MeL}U
```

```
Further oligonucleotides
SEQ ID NO:19    W006_GFP1-a    ACUUGUGGCCGUUUACGUCG$^L$C$^{MeL}$U
SEQ ID NO:20    W038_GFP1-s    GAC$^M$GUAAAC$^M$G
SEQ ID NO:21    W039_GFP1-s    GCC$^M$AC$^M$AAGUU$^M$C$^M$U
SEQ ID NO:22    W056_GFP1-s    GAC$^f$GUAAAC$^f$G
SEQ ID NO:23    W057_GFP1-s    GCC$^f$AC$^f$AAGUT$^f$C$^f$U
SEQ ID NO:24    W058_GFP1-s    GCC$^f$ACAAGUT$^f$C$^f$U
SEQ ID NO:25    W074_GFP1-a    ACUUGUGGCCGUUUACGUCG$^L$C
SEQ ID NO:26    W075_GFP1-a    ACUUGUGGCCGUUUACGUC$^{MeL}$G$^L$C
SEQ ID NO:27    W038_GFP1-s    GAC$^M$GUAAAC$^M$G
SEQ ID NO:28    W039_GFP1-s    GCC$^M$AC$^M$AAGUU$^M$C$^M$U
```

Short sisiRNA Strands for Multiple Stranded Passenger Strand:

```
Two short strands to be used with W004:

SEQ ID NO 33    W141    5'-GC$^{MeL}$C$^{MeL}$AC$^{MeL}$
SEQ ID NO 34    W142    5'-AA$^L$G$^L$ UT$^L$C$^L$ U

Three short strands to be used instead
of W004 + W005:

SEQ ID NO 35    W143    5'-GAC$^{MeL}$ GT$^L$A
SEQ ID NO 36    W144    5'-AAC$^{MeL}$ GG$^L$C C
SEQ ID NO 37    W145    5'-AC$^{MeL}$ AAG$^L$ UT$^{LMeL}$ U

Short strands to be used for T$_m$-studies
related to sisiRNA constructs:

SEQ ID NO 38    W146    5'-GAC GUA
SEQ ID NO 39    W147    5'-GAC$^{MeL}$ GUA
SEQ ID NO 40    W148    5'-GAC G$^L$UA
SEQ ID NO 41    W149    5'-GAC$^{MeL}$ G$^L$T$^L$A
SEQ ID NO 42    W150    5'-G$^L$AC GUA
SEQ ID NO 43    W151    5'-GAC GUA$^L$
```

W037 corresponds to a continuous version of W004 and W005. W034 and W035 is a variant of the W004 and W005 pair where the nick has been shifted one position towards the 3'-end. W040 and W041 are the RNA versions of W004 and W005. W036 is equivalent to W005 but without a 3' terminal U-residue.

W004 is 5'SS1, W005 is 3'SS1, W037 is SS1, W034 is 5'SS3, W035 is 3 SS3, W036 is 3'SS5 and JW1103 is AS1.

A small "L" in superscript indicates that the residue is LNA nucleobase.

A small "MeL" in superscript indicates that the residue is LNA nucleobase with a 5-methylcytosine base.

A capital "M" in superscript indicates that the residue is a 2'-OMe nucleobase

A small "f" in superscript indicates that the residue is a 2'-fluoro nucleobase

Therapeutic sisiRNA Complexes for use in Compositions of the present invention.

```
ApoB-1-      SEQ ID 52  5'-GUC$^{MeL}$AUC$^{MeL}$CAC-3'
sisiRNA      SEQ ID 53  5'-UG$^{MeL}$AAUAC$^{MeL}$AAU-Cl-3'
             SEQ ID 54  3'-CAC$^{MeL}$AG$^{MeL}$UAGUGUGAC$^{MeL}$UUAUG$^{MeL}$UUA-5'

ApoB-1-      SEQ ID 55  5'-GUC$^{MeL}$AUC$^{MeL}$CAC-3'
sisiRNA      SEQ ID 56  5'-UG$^{MeL}$AAUAC$^{MeL}$AAU-Cl-3'
             SEQ ID 57  3'-CAC$^{MeL}$AGUAGUGUGACUUAUGUUA-5'

ApoB-2-      SEQ ID 58  5'-AG$^{MeL}$G$^{MeL}$UGUAUGG-3'
sisiRNA      SEQ ID 59  5'-CUUCC$^{MeL}$AAC$^{MeL}$CUG-Cl-3'
             SEQ ID 60  3'-UC$^{MeL}$UC$^{MeL}$CACAUACCGAAG$^{Me}$UUGGG$^{Me}$AC-5'

ApoB-2-      SEQ ID 61  5'-AG$^{MeL}$G$^{MeL}$UGUAUG-3'
sisiRNA      SEQ ID 62  5'-G$^{MeL}$CUUCC$^{MeL}$AAC$^{MeL}$CUG-Cl-3'
             SEQ ID 63  3'-UC$^{MeL}$UC$^{MeL}$CACAUACCGAAGUUGGGAC-5'

Survivln 1   SEQ ID 64  5'-GC$^{MeL}$AUUC$^{MeL}$GUC$^{MeL}$C-3'
sisiRNA      SEQ ID 65  5'-GG$^{MeL}$UUGCG$^{MeL}$CUUU-Cl-3'
             SEQ ID 66  3'-UUC$^{MeL}$GUAAG$^{MeL}$CAGGCCAACGCGA-5'

Survivin 2a  SEQ ID 67  5'-UUUC$^{MeL}$UGAG$^{MeL}$CU-3'
sisiRNA      SEQ ID 68  5'-GCAG$^{MeL}$GUUC$^{MeL}$UU-Cl-3'
             SEQ ID 69  3'-AG$^{MeL}$AC$^{MeL}$UCGACGUCCAAGGUU-5'

Survivin 2b  SEQ ID 70  5'-UUUC$^{MeL}$UGAG$^{MeL}$CU-3'
sisIRNA      SEQ ID 71  5'-GCAG$^{MeL}$GUUC$^{MeL}$UU-Cl-3'
             SEQ ID 72  3'-AG$^{MeL}$AC$^{MeL}$UCGACGUCCAAG$^{Me}$GUU-5'
```

—Cl-3' indicates a 3' terminal cholesterol conjugated oligonucleotide.

The sisiRNA therapeutic compounds are optionally conjugated with cholesterol at the 3' end of the RNA molecule, such as either the first or second passenger strand or antisense strand.

The pharmaceutical compositions according to the invention suitably comprise chitosan, which may for example be added as particles formed using 800 µl of chitosan in a 1 mg/ml solution at pH 5.5 to which 200 µl of a 0.2 M sodium acetate buffer at pH 5.5 is added. Complexes may be made using, for example 20 µl of 250 µM sisiRNA solution.

Using the sisiRNA designs as described herein, therapeutic sisiRNA complexes can also be designed against numerous other therapeutic targets, for instance against targets where siRNAs have been used previously, such as the target sequences identified in the following references:

Survivin:
Beltrami et al., *J. Biol. Chem.,* 279, 2077-2084.
Coma, S. et al, *Oligonucleotides,* 14, 100-113.
Ning et al., *Int. J. Oncol.,* 25, 1065-1071.
ApoB:
Soutschek, et al., Nature, 432, 173-178.
Hif-1a:
Jiang G et al., Eur J Pharmacol. 2007 Feb. 8
Jiang M et al., J Vasc Res. 2006; 43(6):511-21.
Ono Y et al., J Cell Biochem. 2006 Jun. 1; 98(3):642-9.
K-ras:
Chen L M et al., World J Gastroenterol. 2005 Feb. 14; 11(6): 831-8.
siRNA Sequence:
Kim I A, et al., Cancer Res. 2005 Sep. 1; 65(17):7902-10.
Bcl2:
Miura Y et al., Apoptosis. 2006 October; 11(10):1825-35.

Transfection

Sense and antisense strands where mixed in annealing buffer (10 mM Tris-HCl, pH 7.3, 50 mM NaCl) at 20 mM equimolar concentration and incubated at 95° C. for 1 min and at 1 h at 37° C. Cells used for flow cytometry were plated in 6-well plates and grown in RPMI-1640 containing 10% FBS, 1% penicillin/streptomycin to 60-80% confluence. Cells were transfected using Mirus TransIT-TKO reagent according to manufacturers directions. The final RNA complex concentration was 10-50 nM. After 24 h incubation fresh media was added and the cells were incubated for another 24 h before RNA and protein analysis. EGFP protein expression was quantified by flow cytometric analysis counting approximately 5×04 cells and averaged. Cells used for northern and western analysis were seeded at approximately 20% confluency and transfected using Bio-Rad Silentfect transfection reagent (50 nM final RNA concentration) according to manufacturer's instructions. 24 h later cells were replenished with fresh medium and incubated for another 24 h before either re-transfection using Lipofectamine-2000 (50 nM final RNA concentration) according to manufacturers directions or harvested for western or northern analysis. Western blotting was performed as follows: Cells were washed twice in PBS and an equal amount of cells were lysed in 2×SDS sample buffer [4% Sodium Dodecyl-Sulphate (SDS), 20% glycerol, 125 mM Tris/HCl pH 6.8, 0.01 mg/ml Bromphenol Blue, 10% b-mercaptoethanol] at 90° C. for 2×10 min separated by gentle pippeting. Proteins were separated in 12% SDS acrylamide gels, and electroblotted overnight onto a PVDF membrane (Immobilon). The filter was blocked for 1 h with PBS containing 10% w/v milk. EGFP protein was detected using a 1:1000 dilution of a rabbit polyclonal EGFP antibody. The mouse hnRNP C1 antibody was a gift from Seraphin Pinol-Roma. A horseradish peroxidase (hrp) conjugated secondary antibody (DAKO) was used with ECL reagent (Amersham Blosciences) for visualization. EGFP mRNA was analyzed by Northern blotting according to standard procedures.

mRNA and Protein Quantification

Expression of eGFP protein was analysed by flow cytometric analysis. Western blotting was performed as follows: Cells were washed twice in PBS and an equal amount of cells were lysed in 2×SDS sample buffer [4% Sodium Dodecyl-Sulphate (SDS), 20% glycerol, 125 mM Tris/HCl pH 6.8, 0.01 mg/ml Bromphenol Blue, 10% b-mercaptoethanol] at 90° C. for 2×10 min separated by gentle pippeting. Proteins were separated in an 8% SDS-acrylamide gel, and electroblotted overnight onto a PVDF membrane (Immobilon). The filter was blocked for 1 h with PBS containing 10% w/v milk. EGFP protein was detected using a 1:1000 dilution of a rabbit polyclonal EGFP antibody (Santa Cruz Biotechnology). The mouse hnRNP C1 antibody was a gift from Seraphin Pinol-Roma. A horse radish peroxidase (hrp) conjugated secondary—antibody (DAKO) was used with the ECL reagent (Amersham Biosciences) for visualization. eGFP mRNA was analysed by Northern blotting according to standard procedures.

Stability Assay

RNA/LNA complexes were incubated at 37° C. in 10% foetal bovine serum (Gibco) diluted in D-MEM (Gibco). Samples of 5 µl were collected at indicated time points and immediately frozen on dry ice in 15 µl 1.33×TBE/10% glycerol loading buffer and subjected to non-denaturing PAGE on a 15% gel. RNA's were visualised with SYBR gold (Invitrogen).

Interferon Response Assay siRNA-variants (80 nM) or poly(I:C) (0.8 µg/ml) were transfected into T98G cells using the TransIT-TKO® transfection reagent (Mirus) according to the manufactures protocol. T98G cells were grown in 10% FCS in DMEM (Gibco). Total RNA was purified using Trizol (Invitrogen), DNase treated and subjected to oligo-dT-primed reverse transcription. qPCR was performed using the platinum SYBR®Green qPCR supermix (Invitrogen) on a Stratagene Mx3005p qPCR system. Primers used for amplification of ISG56: 5'-AAG-GCAGGCTGTCCGCTTA-3' and 5-TCCTGTCCTTCATC-CTGAAGCT-3'. Primers for amplifying GADPH: 5-GAAG-GTGAAGGTCGGAGT-3' and 5'-GAAGATGGTGATGGGATTTC-3'.

The PCR conditions are: 1 cycle: 95° C. 10 min. 40 cycles: 95° C. 30 sec, 55° C. 1 min, 72° C. 30 sec. 1 cycle: 95° C. 30 sec, 55° C. 1 min, 95° C. 1 min. Relative quantification of mRNAs levels were done by using the ΔΔCT-method. The experiments were done in triplicates and ISG56 levels for siRNA-treated cells were normalized to TransIT-TKO treated controls.

Dual Luciferase Assay

H1299 cells were plated in 6-well plates in RPMI supplemented with 10% fetal bovine serum and grown ON to 40-60% confluence. pISO$_{antisense-target}$ and pISO$_{sense-target}$ (1 µg) were co-transfected with 0.002 µg pRluc-N2 (Perkin-Elmer) and the siRNA duplexes (10 nM final concentration) by simultaneous use of 6 µl TransIT-LT1 (Mirus) and 6 µl TransIT-TKO (Mirus) according to the manufactures protocol. The Dual-luciferase assay was done 48 hours posttransfection using the "Dual-luciferase reporter assay system" (Promega) according to the manufactures protocol. The luciferase activities were measured on a Lumat LB 950 luminometer (Berthold) and normalized to the renilla luciferase signal.

Example 1

Formation of a Trimeric RNA Complex with High Stability in Serum

Small internally segmented interfering RNA (sisiRNA) refers to a duplex that contains a discontinuous antisense strand and a continuous antisense strand. We initially tested a sisiRNA construct composed of an antisense strand containing two LNA residues near the 3'-end (JW1103) and a discontinuous passenger strand comprising two RNA molecules; W004, a 10 nucleotide RNA molecule with two LNA residues and W005, a 12 nucleotide RNA molecule comprising three LNA residues.

Figure 7:
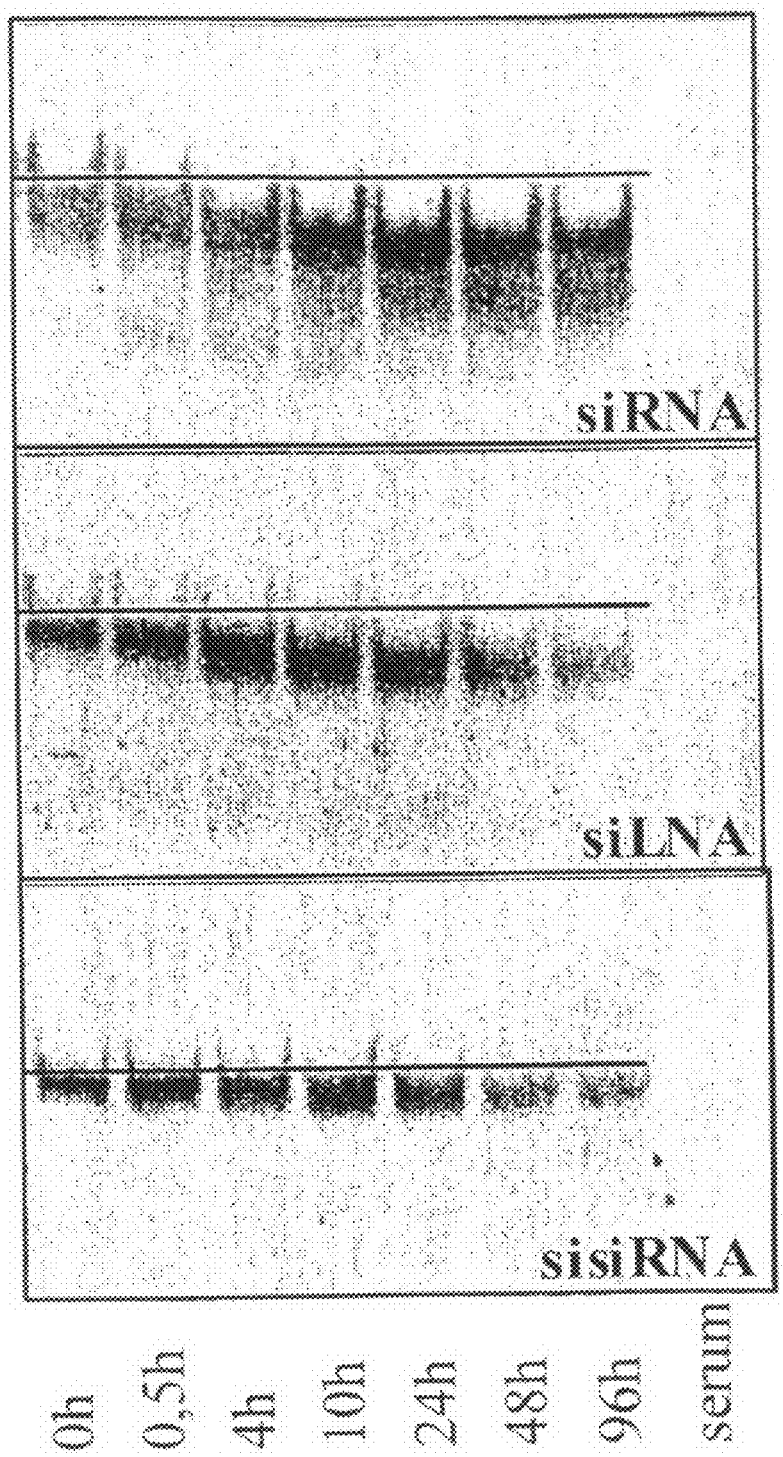

The LNA modified sisiRNA was significantly more stable in 10% serum than ordinary siRNA (eGFPsiRNA), which was rapidly shortened a few nucleotides in a few hours and further degraded in 1-2 day (FIG. 7, compare upper panel). In contrast, only a very small decline in sisiRNA size was observed over a 5-day incubation period, which may reflect the removal of the 3'U residue in the 3-end of W005 (FIG. 7, lower panel). Since this U is only added as an extra unmodified nucleotide to ease the synthesis, this should only increase the potency of the sisiRNA. When comparing the sisiRNA to an ordinary LNA-modified construct (siLNA comprising JW1103 and JW1106; FIG. 7, middle panel) without a hick in the sense strand the overall stability was similar, although the ordinary siLNA yielded a slightly shorter degradation product. The exact reason for this difference in mobility shift was not characterized further.

Example 2

RNAi Activity of sisiRNA

An siRNA containing a nicked sense strand is fully functional: Together with a standard siRNA and unrelated control siRNA the constructs were tested by transfection into a H1299 lung carcinoma cell line that stably expresses destabilized EGFP. Subsequently, the level of EGFP mRNA and protein expression was monitored on the basis of fluorescence microscopy, northern blotting, western blotting and flow cytometry. Treating cells with 50 nM LNA-modified sisiRNA or siRNA yielded a comparable 10-fold knock down after 48 hours. Omitting one or both of the short sense strands (5'SS1 or 3'SS1) eliminated the activity of the sisiRNA, suggesting that the activity of the LNA modified sisiRNA was strictly depending on the presence of all three strands. Hence, the sisiRNA design has similar potent silencing efficiency as standard siRNAs in short-term studies.

To eliminate sense strand incorporation into activated RISC, we applied a novel siRNAs design characterized by an intact antisense strand complemented with two shorter sense strands. We anticipated that by incorporating LNA nucleotides into such tri-molecule construct, sufficiently stability and dsRNA structural mimicry would be achieved to allow RNA interference activity. We initially designed an sisiRNA composed of a 10 nt and 12 nt sense strand directed towards a previously established functional target in the mRNA encoding enhanced green fluorescent protein (EGFP). To stabilize the sisiRNA construct we incorporated LNA at two and four positions in the sense 5' and 3' half-strands, respectively, and near the 3' end of the antisense strand and assembled the construct from these three strands ((JW1103, W004 and W0OS). The sisiRNA, comprising an antisense strand and a discontinuous passenger strand (JW1103, W004 and W005), remains fully active based on visual inspection of eGFP expression in the cells (FIG. 8) and its capacity to knock down eGFP protein (FIG. 9A) and eGFP mRNA (FIG. 9B; lanes 1-6).

Figure 8:
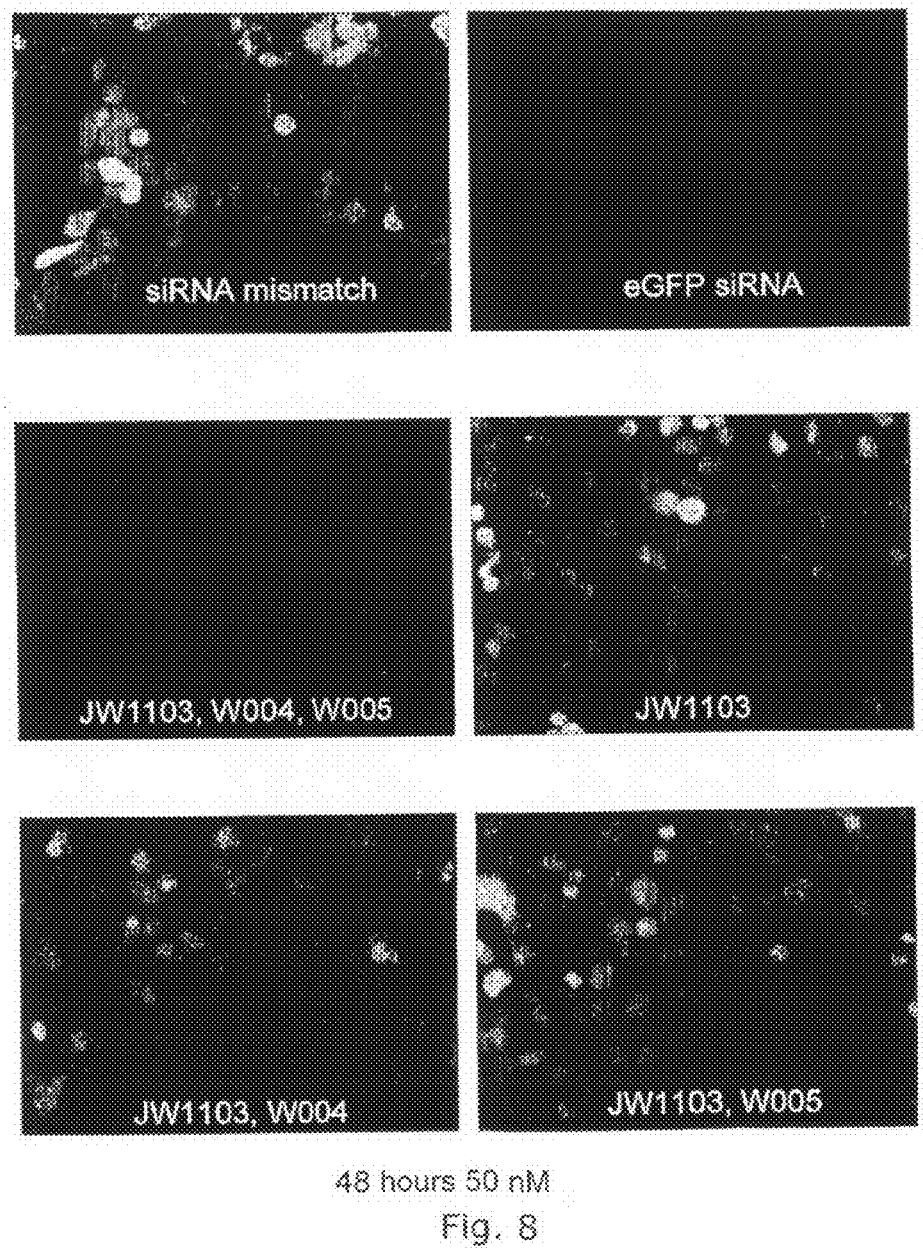
Figure 9:
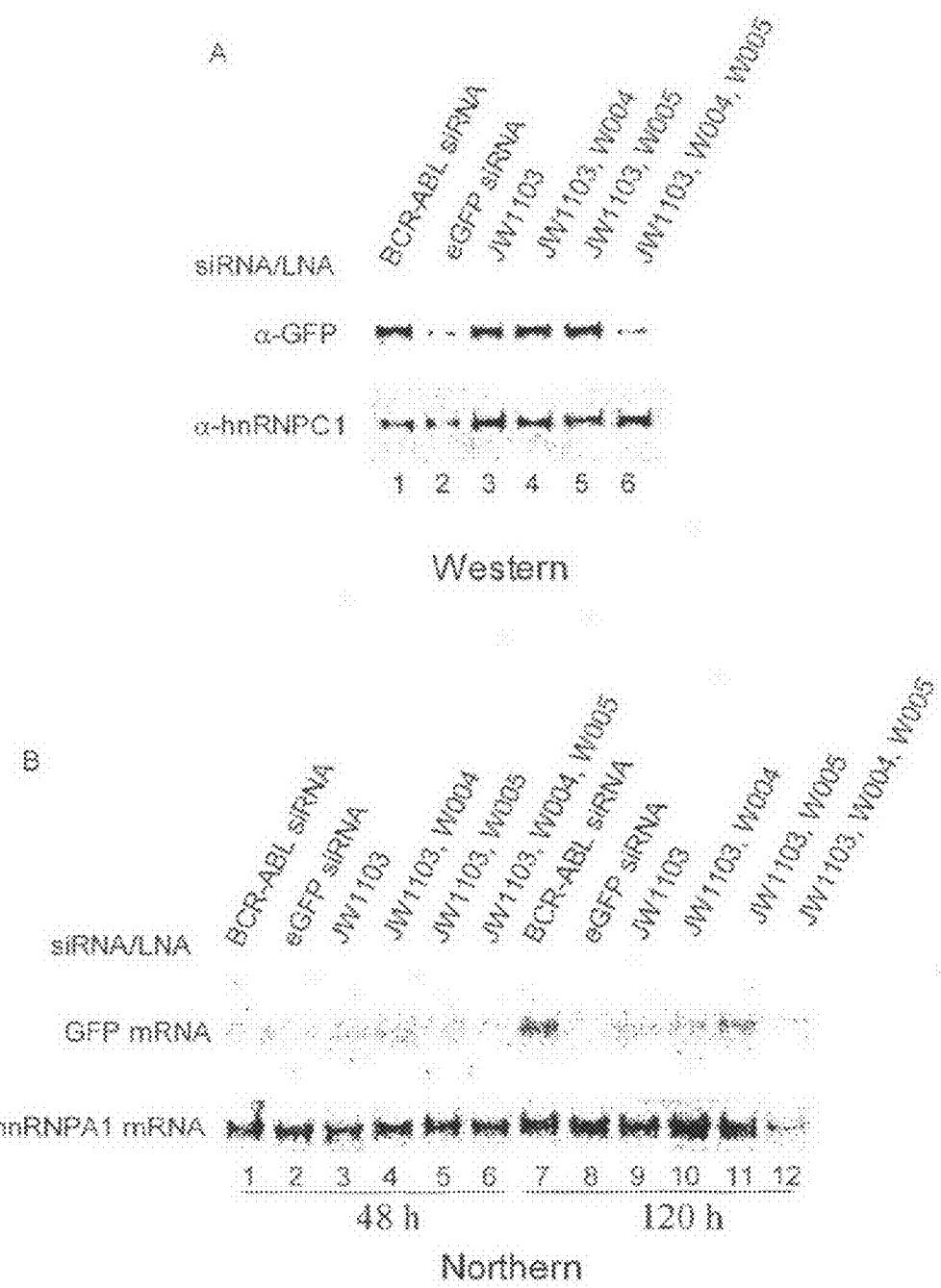

It is important that both sense strands are present (the two RNA molecules making up the discontinuous passenger strand) since omitting either W004 or W005 or both from the complex completely abolished the interference activity, both at the level of the mRNA and protein expression (FIGS. 8 and 9).

Figure 10A:
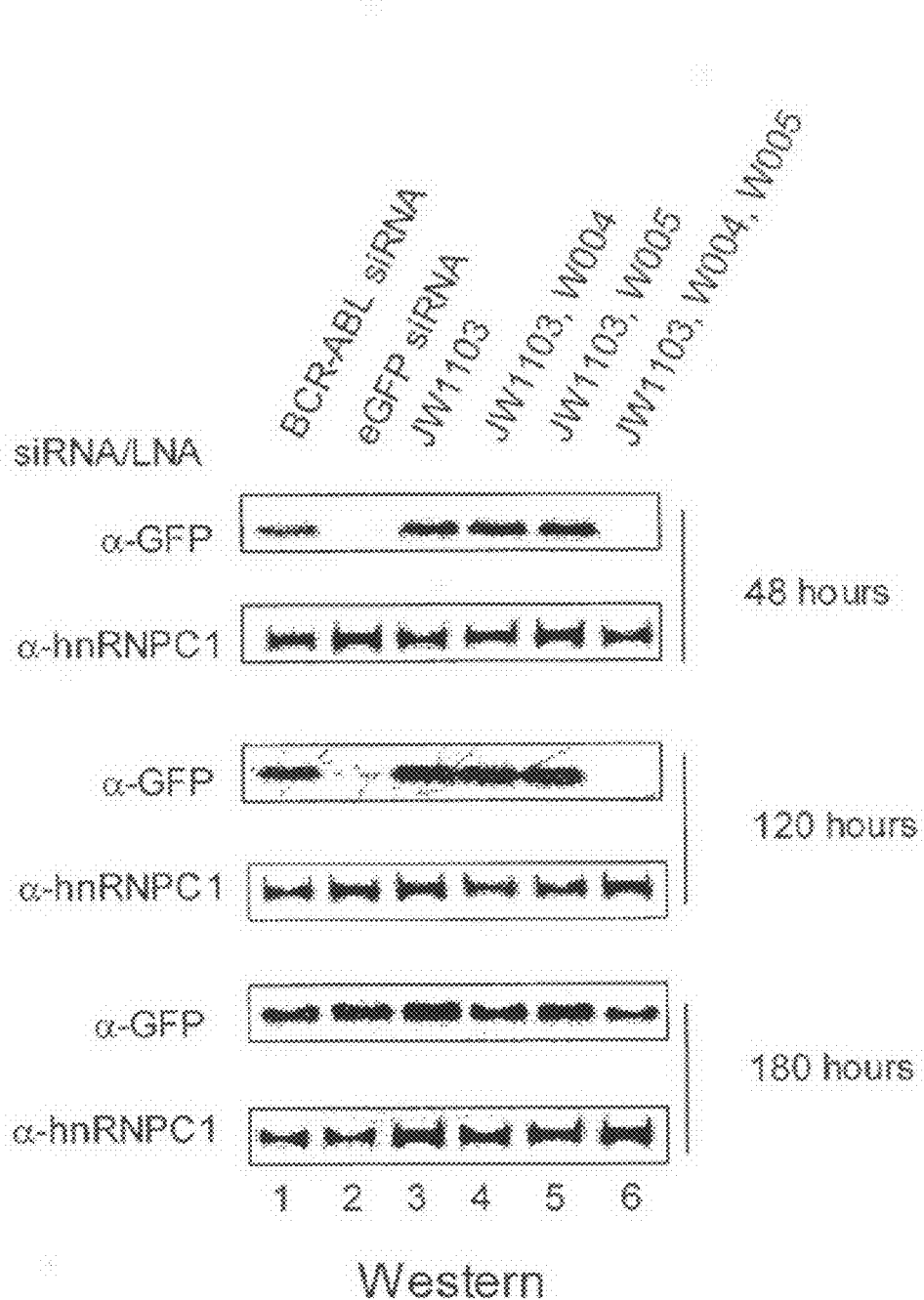
Figure 10B:
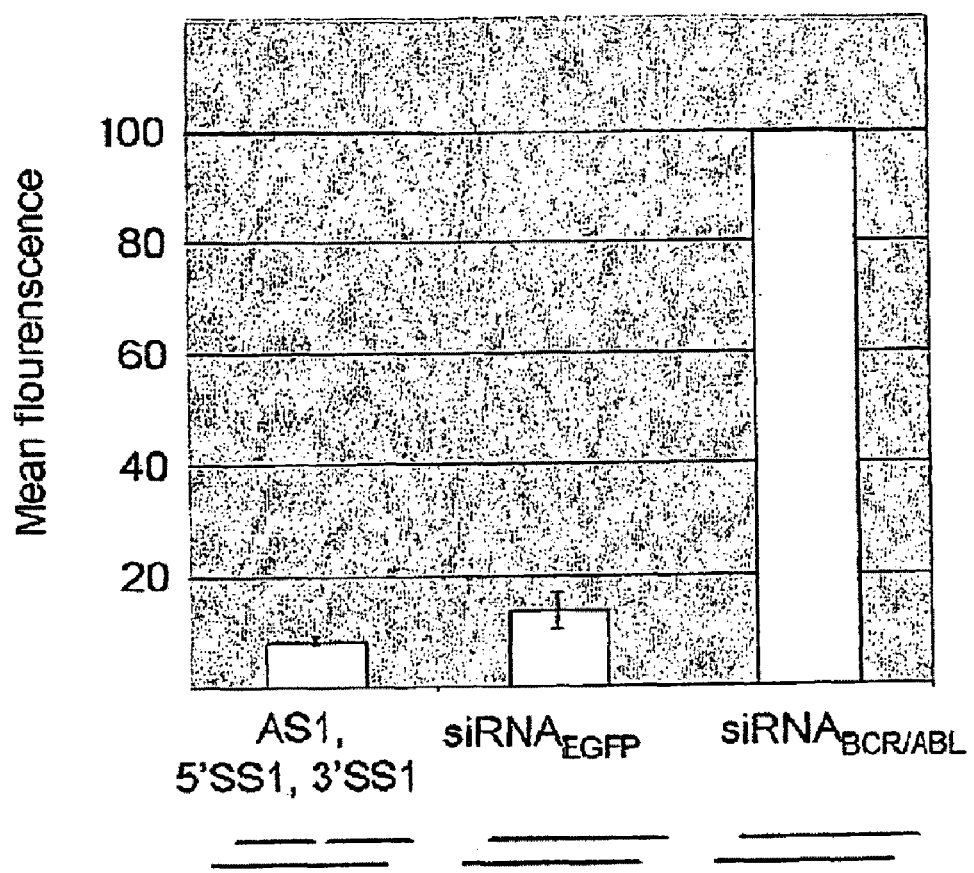

To test the performance of LNA-modified sisiRNA and standard siRNAs in long-term knock down, cells were retransfected after 48 hours and harvested after 120 (5 days) or 180 hrs (7.5 days). After 120 hours the siRNA treated cells had regained approximately 50% of EGFP mRNA and some EGFP protein expression (FIG. 9B). In contrast, the LNA modified sisiRNA treated cells remained low in both EGFP mRNA and protein expression (FIGS. 9 & 10). Even after 180 hours a significant knock down of EGFP expression was still observed in cells treated with LNA modified sisiRNA whereas EGFP expression was fully recovered in cells treated with the standard siRNA (FIG. 10A). Hence, sisiRNA exhibits prolonged silencing activity in cell culture as compared to standard siRNAs.

Example 3

Comparing the Activity of sisiRNA to Other siRNA/LNA Constructs

To assess the efficacy of sisiRNA compared to ordinary siRNA/LNA we transfected HT1092 cells with sisiRNA, two siLNA constructs (JW1103+JW1105 and JW1103+JW1106) that previously have been characterized as highly active siLNA constructs and ordinary siRNA.

The efficiencies of the sisiRNA, the siLNA and the normal siRNA were very similar, all giving an 80-90% knock down at 10-50 nM concentrations (FIG. 11A).

To investigate whether differences in activity would be revealed at lower concentration the duplexes were applied in 10 μM-100 nM concentrations. Moreover a continuous duplex (JW1103 and W037), which contains the identical LNA modification pattern as the sisiRNA, was included. Again, no significant differences in RNAi potency were observed (FIG. 11B). Notably, all duplexes resulted in an approximately 50% knock down when the duplex was applied at very low concentration of (10 μM).

Example 4

Optimization of sisiRNA Design

To investigate the flexibility in the sisiRNA design we tested a series of different sense and antisense strand designs.

Figure 12:
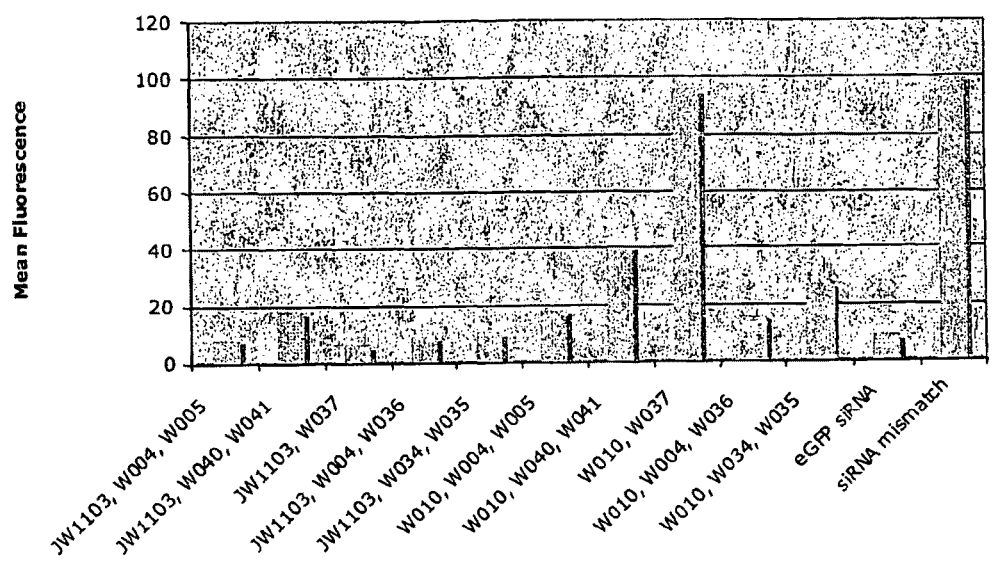

Using unmodified discontinuous sense RNAs, W040 and W041 corresponding to W004 and W005, respectively, resulted in a complex that induced RNAi activity, though with a somewhat decreased activity compared with LNA-modified sisiRNA (compare columns 1 and 2 In FIG. 12).

Moving the nick in the sense strand of the sisiRNA one nucleotide towards the 3' end (11+11 design) did not interfere with the RNAi activity (column 5, FIG. 12).

For technical reasons in the synthesis an additional U-residue was present at the 3' end of W005. To test whether this residue affects the activity of the RNA complex a new oligo was synthesized without the terminal U-residue (W036). This change did not alter the activity of the construct significantly (column 4, FIG. 12).

JW1103 only contains 2 LNA residues near the 3' end since we have previously found that extensive modification of the antisense strand strongly interferes with RNAi activity. To investigate whether the discontinuous sense strand may influence the requirement for an antisense with a limited number of modified nucleotides we tested the same set of sense strand with a highly modified antisense strand that contains 6 LNA residues (W010). This antisense strand is essentially inactive when paired with a continuous modified sense strand (W037; column 8, FIG. 12).

Interestingly, this requirement was less stringent when a discontinuous sense strand is used where only an approximately two-fold decrease in knock down efficiency was observed (Compare columns 6, 7, 9 and 10 with 1, 2, 4 and 5, respectively; FIG. 12). Thus, when using a discontinuous passenger strand, it may be possible to use a potentially more stable antisense strand with more LNA residues.

Example 5

Immune Response of sisiRNA

Figure 13:
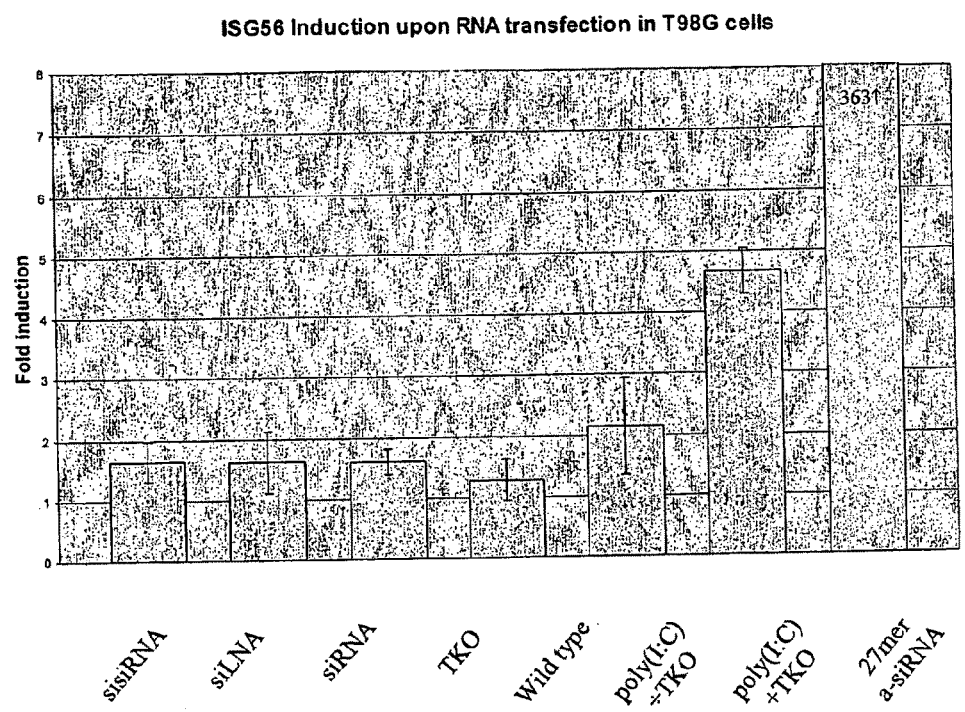
FIG. 13: ISG56 induction upon RNA transfection in T98G cells. Assessing the interferon response induced by sisiRNA and other siRNA constructs. The level of IGH56, that is a downstream marker for interferon alpha response was measured by quantitative RT-PCR. Poly(I/C) was included as a positive control (drawn out of scale). The 27-mer siRNA is composed of a 27- and a 25-nucleotides guide- and passenger strand, respectively, has previously been shown to induce interferon moderately. LNA-modified sisiRNA and LNA-modified siRNA do not activate the interferon system as evaluated by induction of ISG56 in T98G cells. The glioblastoma cell line T98G was transfected with 80 nM of the siRNA variants or 0.8 µg poly(I:C) as indicated and ISG56 mRNA levels evaluated by qPCR analysis 48 hours post-transfection. Only transfection of poly(I:C) (pos. control) lead to high levels of ISG56 induction, whereas ISG56 levels for all siRNA-variants were indistinguishable from untreated cells or cells treated with transfection reagent alone (Mirus Trans-IT TKO®).

Chemical modifications of nucleic acids can have a dramatic influence on the cellular immune response in cultured cells and in animals. To analyze the immunogenic properties of the sisiRNA constructs we transfected the Human glioblastoma T98G cell line with 80 nM of the different siRNA constructs and measured the induction of ISG56, which is strongly induced by both type I IFN and dsRNA. PKR-mediated ISG56 induction upon siRNA transfection has previously been reported in T98G cells, yet no significant differences in ISG56 induction were observed between sisiLNA, siLNA and unmodified siRNA (FIG. 13). In contrast, poly(I/C) induced the ISG56 several hundred fold. We conclude that the sisiRNA does not induce interferon alpha to any significant extent at an siRNA concentration of 80 nM.

Example 6

Reduced Off Target Effects

Figure 14:
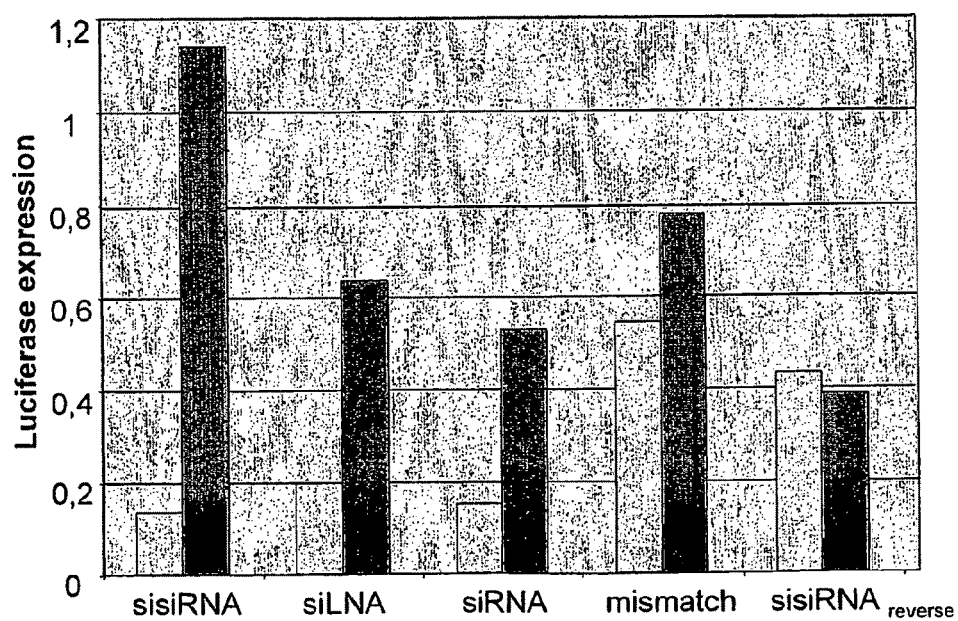
FIG. 14. Measuring the off-target effect of sisiRNA.

The discontinuity of the intended passenger strand will probably eliminate its incorporation into the RISC complex. To test this hypothesis, the EGFP target sequence was inserted either in the sense or antisense orientation within the 3'UTR of a luciferase reporter construct (FIG. 14). This strategy allowed us to assess the knock down effect derived from passenger strand incorporation. As intended, the sisiLNA construct was significantly more specific than the equivalent siRNA and siLNA duplexes. Luciferase expression from the mRNA harboring the EGFP sense target was 8-fold more reduced by sisiRNA than from the mRNA containing the reversed target. In comparison, siLNA and siRNA only differentiated between the two constructs with an approximately 3-fold difference. This gain in specificity is surprising considering that the EGFP target sequence used in this study corresponds to a commercial EGFP siRNA from Dharmacon that fulfills most of the thermodynamic rules for being an optimal target. To test whether it is possible to force the suboptimal passenger strand into RISC anyway, a new LNA-modified sisiRNA with an intact passenger strand and a nicked antisense strand (sisiLNA$_{reverse}$) was synthesised and tested for the ability knock down mRNA containing a forward and reversed target. Although the target preference was not completely reversed, the sisiLNA$_{reverse}$ exhibited the strongest knock down (50%) of the transcripts containing the reverse target than any of the other siRNA constructs, and was the least active on the sense target (FIG. 14). These data clearly demonstrate that the sisiRNA is significantly more specific for the intended target.

Example 7

Stability in 80% Serum

Figure 15B:
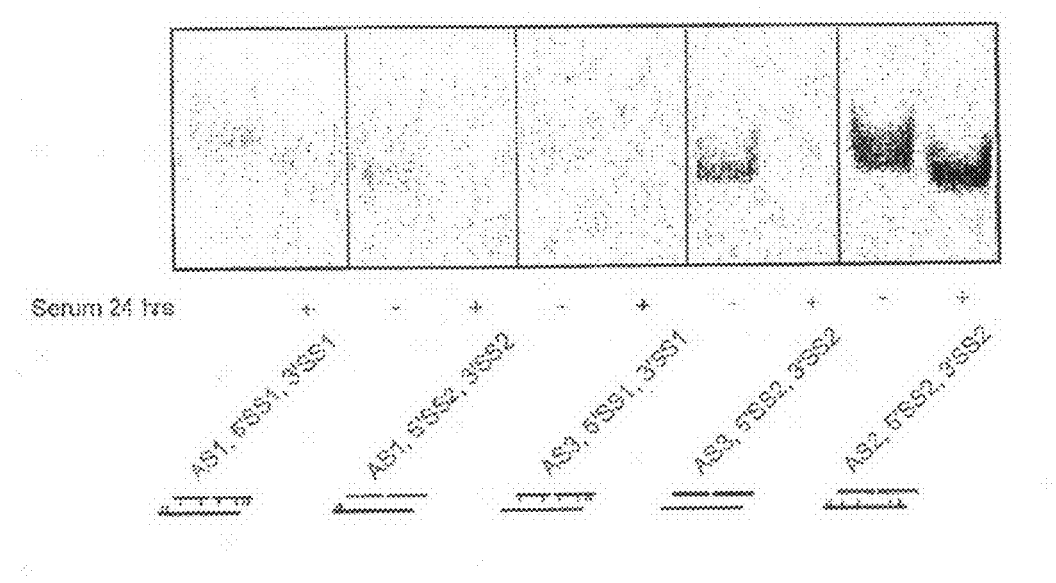

The stability of siRNA, sisiRNA and siLNA was further tested by incubation in 80% FCS (FIG. 15). Both sisiRNA and siLNA exhibit increased serum stability compared unmodified to siRNA.

Example 8

Position and Size of the sisiRNA Sense Strand Nick

To further optimize the sisiRNA design we tested a series of different sense and antisense strands. In one experiment the position of the gap in the sense strand was either shifted one position towards the 5' end (AS1+5'SS4+3'SS4; sisiRNA$_{9+13}$) which since the initiation of the work has been reported to be the natural cleavage site for Ago2 in RISC or one position towards the 3' end (AS1+5'SS3+3'SS3; sisiRNA$_{11+11}$). For the sisiRNA$_{11+11}$ design only a minor decline in silencing was observed whereas the sisiRNA$_{9+13}$ design was slightly less efficient in gene silencing (FIG. 16A). Increasing the gap size of the sense strand to 1-2 nucleotides resulted in a dramatic decline in sisiRNA activity irrespectively of gap position (data not shown). Hence the sisRNA$_{10+12}$ design has proven most efficient among all sisiRNAs tested. The 3'SS1 strand was initially designed to contain an additional U-residue at the 3' end in order to ease the chemical synthesis. To test whether this residue affects sisiRNA activity, 3'SS5 was synthesized without this terminal U-residue (3'SS5). This alteration did not alter the activity of the construct significantly (compare column 2 and 4, FIG. 16B).

Example 9

The Discontinuity of the Sense Strand Completely Eliminates its Guide Activity

To test whether the discontinuity of the intended sense strand eliminates its contribution to gene silencing we inserted the EGFP target sequence for either the siRNA$_{EGFP}$ antisense or sense strand within the 3'UTR of a luciferase reporter construct (FIG. 17). This strategy allowed us to differentially assess the knock down effect derived from the antisense- and the sense-strand incorporation. As predicted, the LNA modified sisiRNA construct was significantly more specific than the equivalent siRNA and LNA modified siRNA duplexes since approximately 50% knockdown was constantly seen from the sense strand with standard siRNA design (Columns 1 and 2, FIG. 17). In contrast, the sisiRNA design completely abrogated the silencing of the "sense target" as compared to mismatch controls without compromising the potent knockdown mediated by the antisense strand (Column 3, FIG. 17). To test whether it is possible to abrogate the silencing function of an otherwise optimal antisense strand with a nick, another LNA modified sisiRNA with an intact sense strand and a discontinuous antisense strand (5'AS2, 3'AS2, SS3) was tested for the ability to knock down the antisense and sense targets. This design completely eliminated silencing of the antisense target yet retained silencing of the sense target to a level comparable to the standard siRNA (column 4, FIG. 17). Collectively these data clearly demonstrate that the sisiRNA construct exhibits a much higher level of specificity for the intended target compared to the usual siRNA design.

Example 10

The sisiRNA Design is Compatible with Higher Levels of Antisense Strand Modification We and others have previously found that extensive LNA-modification of antisense strands strongly interfere with RNAi activity in standard siRNA designs (FIG. 18, Column 5 and data not shown) (Elmen, J., et al. (2005) Nucleic Acids Res, 33, 439-447., Braasch, D. A. et al., (2003) Biochemistry, 42, 7967-7975.). Therefore we initially designed AS1 to contain only two LNA residues near the 3' end. To investigate whether the discontinuity of the sense strand influences the requirement for unmodified residues in the body of the antisense strand we tested an LNA modified sisiRNA with a highly modified antisense strand containing six LNA residues (AS2). This antisense strand is essentially inactive when paired with an all-RNA sense strand (data not shown) or a LNA modified sense strand (LNA modified siRNA duplex AS2+SS1 FIG. 18B, column 2). Interestingly, the requirement for unmodified residues in the antisense strand was less stringent when using the sisiRNA design (compare columns 2 and 3, FIG. 18B). A similar improvement in knock down efficiency was observed using the 3' end shortened sense construct and the LNA modified sisiRNA$_{11+11}$ design. This suggests that the sisiRNA design may partly rescue the impaired loading of heavily modified antisense strands into activated RISC. To test if a similar effect applies to other types of chemical modifications that do not increase siRNA thermodynamic stability, we tested three designs containing either additional single N2'-adamantyl (AS4 and AS5) or N2'-pyren-1-yl 2'-amino-LNA-T (AS6) (FIG. 18A) modifications in the antisense strand. These types of modifications render the siRNA almost non-functional when paired to SS1 in a standard (LNA-modified) siRNA design (FIG. 18B, Column 4, 6, 8). However, in the context of the sisiRNA design, both the adamantyl and pyrenyl modified antisense strands caused a significant ~2.5 to 4 fold increase in knock down efficiency (FIG. 18B, Column 5, 7, 9). Collectively this shows that the sisiRNA design can accommodate a wide variety of bulky chemical modifications that otherwise are incompatible with the activity of standard siRNA.

Figure 18C:
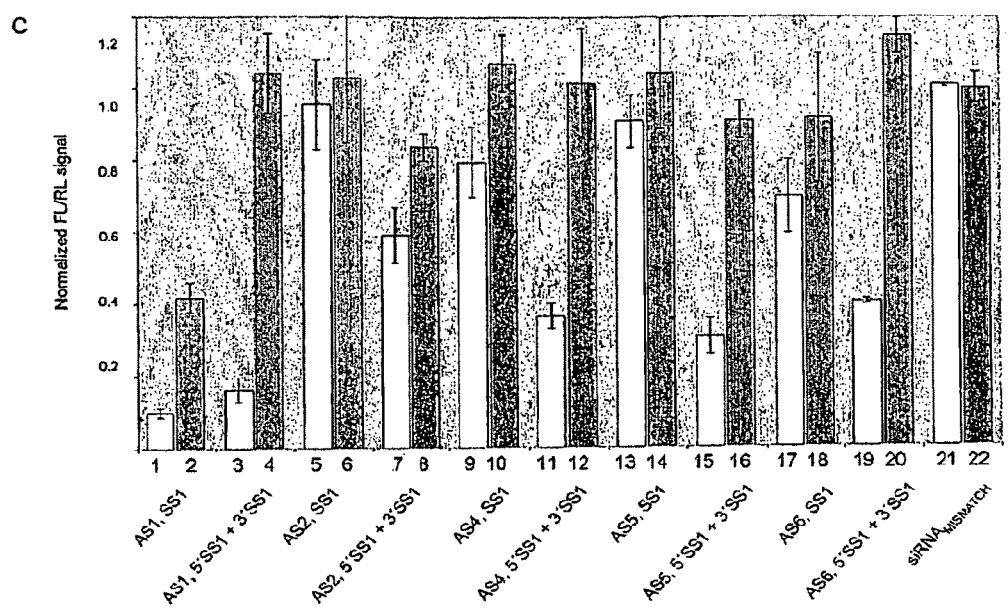
FIG. 18. The sisiRNA design supports the silencing effects of chemically modified antisense strands. (A) molecular structure of an LNA-monomer, a N2'-adamantylmethylcarbonyl 2'-amino-LNA monomer (aT) and a N2'-pyren-1-ylmethyl 2'-amino-LNA-thymine monomer (pT). (B) Analyzing the effect of the sisiRNA design on the silencing efficiency of heavily-modified antisense strands. The Mean fluorescence of approximately 50.000 cells was measured by flow cytometry. The siRNA mismatch represents a siRNA that contains four mismatches to the EGFP target (C) The knockdown activity of the two strands was assessed by measuring luciferase expression from reporter constructs containing either the target sequence in the sense or the antisense orientation (light and dark grey bars, respective). The experiment was performed in triplicates and for each reporter construct the firefly luciferase (FL)/renilla luciferase (RL) ratio was normalized to mismatch controls.
Figure 26:
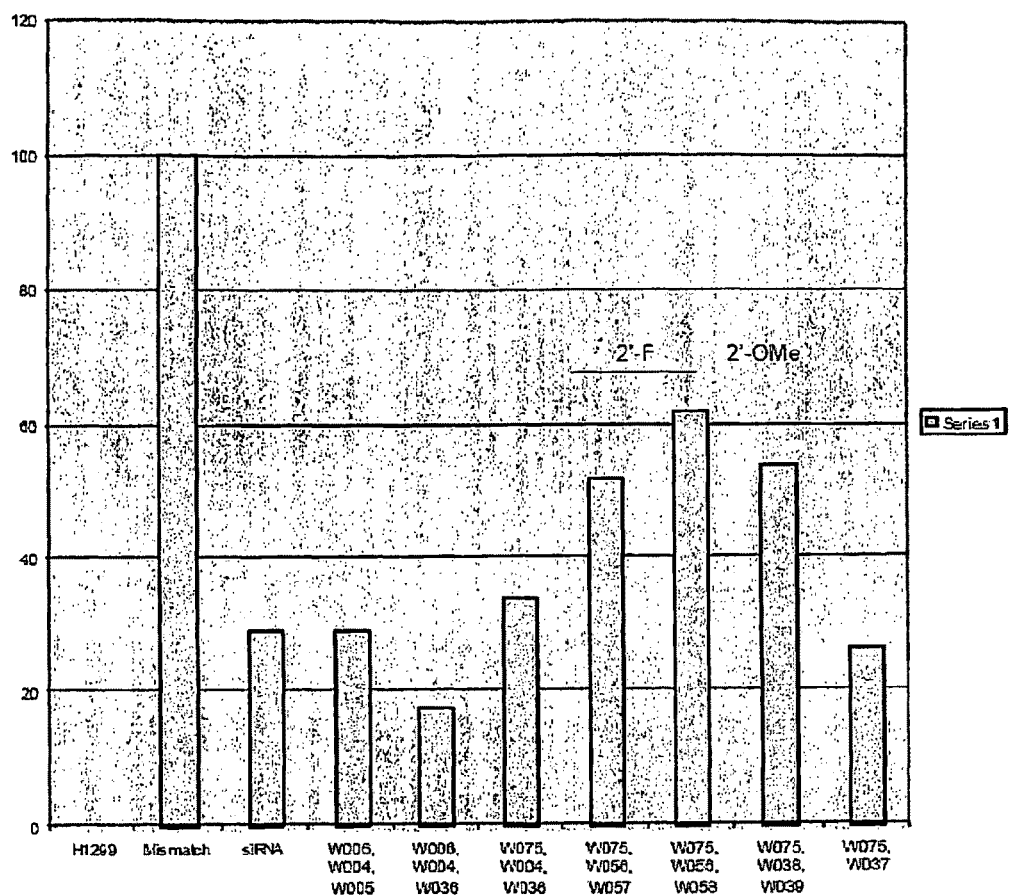
FIG. 26 shows the testing of 2° F. and 2'OMe sisRNA constructs as compared to LNA sisRNA constructs and illustrates that when the passenger strand is modified with 2'-F or 2'OMe that the down regulation is not nearly as effective as compared to comparative constructs using LNA.
Figure 27:
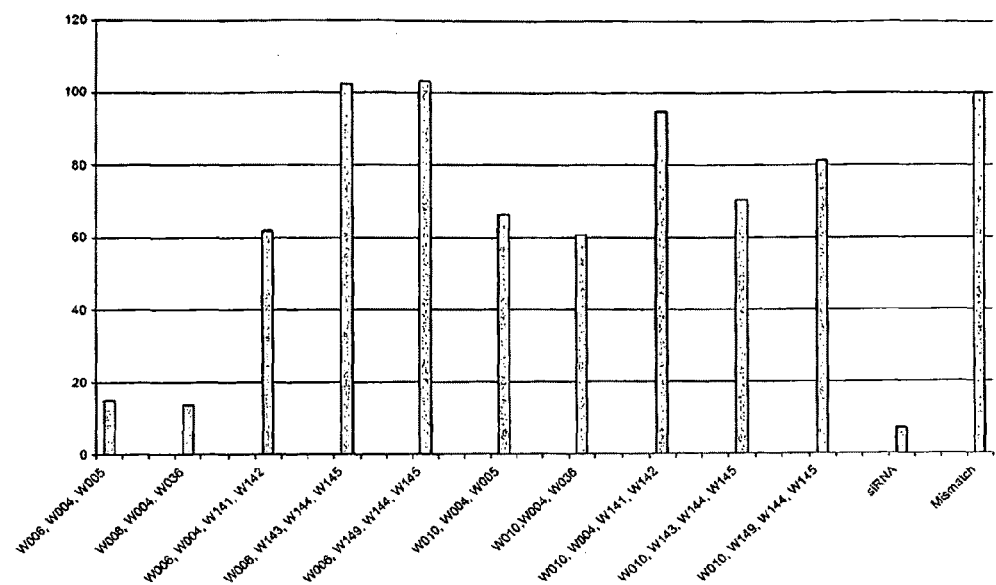
FIG. 27 illustrates that sisiRNA constructs with three RNA molecules in the passenger strand are also effective in down-regulating their target mRNA, although the effect is not as pronounced as equivalent '3 molecule' sisiRNA where the passenger strand consists of only two RNA molecules.

To characterize the mechanism for the relax stringency of the antisense structure further, we investigated the fate of the sense strand (SS1) in the highly functional light antisense-modified siRNA (AS1, SS1) as compared to the heavy antisense-modified siRNAs (AS2, SS1; AS4, SS1; AS5, SS1; AS6, SS1). The LNA-modified siRNA (AS1, SS1) caused a ~2.5 fold reduction of reporter levels from the reverse target (FIG. 18C, column 2) whereas no significant reduction was observed for this target using highly modified siRNAs (AS2, SS1; AS4, SS1; AS5, SS1; AS6, SS1) (FIG. 18C, column 6, 10, 14, 18). This strongly suggests that RISC loading is defective for either strands if the antisense is heavily modified and that the sisiRNA design may facilitate RISC loading of heavily modified siRNA duplexes rather than affecting strand selection prior to or during RISC loading.

Example 11

Evaluation of Different Entropies of Chitosan-siRNA on Delivery from Nose to Brain and Nose to Lung Delivery The mucoseoadhesive and mucopermeation properties of chitosan are utilised for mucosal delivery of siRNA and sisiRNA e.g. nasal, pulmonary, oral and vaginal routes in an EGFP transgenic mice and diseased animal models. In addition, local routes of administration such as intraperitoneally and intradermal will be evaluated using the chitosan-based system. In one study that has recently been conducted, the difference in the distribution to the lung and olfactory region of Cy3-labelled siRNA and sisiRNA formulated into discrete particles with Chitosan at different entropies or siRNA delivered with Chitosan in a mixture prepared just prior to nasal administration. In this study the mice received 30 µl volume (15 µl per nostril), containing 5 µg Cy3-siRNA at day 1 and 3 intranasally delivered. Subsequently, whole body perfusion was performed at day 5. Lung, liver and brain are currently being dissected and sectioned at Stereology Research Laboratory, AU and Ortopeadic Research Laboratory, respectively.
Optimizing Delivery and Efficacy of siRNA and sisiRNA in Pulmonary Delivery We have implemented a catheter-based nebuliser system for endotracheal delivery of aerosolised formulations (chitosan/siRNA and naked siRNA) and demonstrated better lung deposition at a lower dosage compared to intranasal administration of liquid formulations.
Analyses of the Interferon Response and Off-Target Effects In Vitro and In Vivo Whole genome expression profiling are conducted to assess RNAi-induced off-target/interferon induced effects from different siRNA and sisiRNA constructs in an in vitro assay. In an in vivo study, blood samples from mice treated with same set of modified siRNA using different delivery routes (pulmonary, intravenous, intraperitoneal) are profiled for cytokine expression using luminex expression profiling system.
Assessment of the Pharmacokinetic Properties of Chemically Modified siRNA and sisiRNA Inhibitors Against Reporter Genes in Reporter Mouse Models Different siRNAs, siLNA and sisiRNAs are tested in transgenic eGFP mice for functional properties including efficacy, bioavailability, organ distribution, siRNA stability (half life and clearance), toxicity and immune response. Different delivery routes (ex vivo, nasal, pulmonary, intravenous, intraperitoneal and local) are explored. The optimised RNAi inhibitors are tested in combination with delivery systems (naked, chitosan polyplex, liposome). The possibility of targeting ligand conjugated siRNA to specific cells or tissues are analysed in mice. Radiolabelled or fluorescently labelled siRNA are used to visualise the localisation.

Example 12

Evaluation of the Knockdown Effect of siLNA and sisiRNA on EGFP Expression in the Lung after Nasal Delivery and Intravenous Delivery The aim of this study is to test the knockdown of EGFP in lung bronchiole epithelial cells after nasal administration or intravenous injection of naked siLNA and naked or chitosan-formulated sisiRNA.
Test Article Formulation and Preparation HMW chitosan is used to form nanoparticles containing sisiRNA, in acetate buffer (0.2 M, pH 5.5) at 250 µg/ml sisiRNA. The particles are concentrated in acetate buffer (for intranasal formulations) using vivaspin concentration columns to 1 mg/ml sisiRNA.

Unformulated siLNA/sisiRNA will be concentrated in PBS (1 mg/ml) for intravenous delivery and in acetate buffer for intranasal delivery.

Constructs:

| | | |
|---|---|---|
| siRNA | SEQ ID 44 | 5'-GACGUAAACGGCCACAAGUUC |
| | SEQ ID 45 | 3'-CGCUGCAUUUGCCGGUGUUCA |
| siRNA-mismatch | SEQ ID 46 | 5'-GACUUAGACUGACACAAGUUC |
| | SEQ ID 47 | 3'-CGCUGAAUCUGACUGUGUUC |
| siLNA | SEQ ID 48 | 5'-GACGUAAACGGCCACAAGUTCU-3' |
| | SEQ ID 49 | 3'-UCGCUGCAUUUGCCGGUGUUCA-5' |
| sisiRNA | SEQ ID 50 | 5'-GACGUAAACG GCCACAAGUTCU-3' |
| | SEQ ID 51 | 3'-UCGCUGCAUUUGC-CGGUGUUCA-5' |

Residues in bold = LNA

Dose Regime and Groups

15 EGFP transgenic mice will be distributed into the following groups and treated with:
Group 1: Naked siLNA, intranasally (3 mice)
Group 2: Naked sisiRNA, intranasally (3 mice)
Group 3: chitosan-sisiRNA particles, intranasally (3 mice)
Group 4: Naked sisiRNA, intravenously (3 mice)
Group 5: Control nasal delivery, siRNA-mismatch (3 mice)

While anesthetized each mouse each day for 5 successive days receives 30 µl volume (15 µl per nostril), when intranasally administered, or 50 µl, when intravenously administered.

Subsequently, whole body perfusion is performed and organs are dissected (lung, liver, spleen, head, kidney).

Example 13

Knock-Down of EGFP in the Lungs of Transgenic Green Mice Using an Aerosolizing Catheter The aim of this study is to test the knockdown of EGFP in lung bronchiole epithelial cells after intratrachael administration chitosan-formulated siRNA, siLNA and sisiRNA.

The study investigates the knock-down efficiency of chitosan particles containing siRNA against EGFP in lungs of transgenic green mice. The particles were delivered via the endotracheal route using a nebulising catheter to increase the delivery of siRNA to deep pulmonary regions such as the alveoli.

Constructs:

| | |
|---|---|
| siRNA | as Example 11 |
| siRNA-mismatch | as Example 11 |
| sisiRNA | as Example 11 |

Study Design:

12 transgenic mice expressing EGFP are dosed twice.
Group 1: Chitosan/siRNA (4 mice)
Group 2: Chitosan/siRNA mismatch (4 mice)
Group 3: Chitosan/sisiRNA (4 mice)

While anesthetized each mouse receives 2 doses each delivering 2 µl of the particle solution on day 1 and 2 doses again the next day (day 2). 48 hours later the tissue is fixated by whole body perfusion (day 4).

Sections are taken from the lungs and are investigated for knock-down of EGFP.

Particles are formed using 800 µl of chitosan in a 1 mg/ml solution at pH 5.5 to which 200 µl of a 0.2 M sodium acetate buffer at pH 5.5 was added. Complexes are made using 20 µl of 250 µM siRNA solution.

Example 14

Cell Culture Model

The following sisRNA constructs are prepared according to the methods disclosed in WO2005/073378.

The effect of the sisiRNAs on target nucleic acid expression can be tested in any of a variety of cell types provided that the target nucleic acid is present at measurable levels. Target can be expressed endogenously or by transient or stable transfection of a nucleic acid encoding said nucleic acid. The expression level of target nucleic acid can be routinely determined using, for example, Northern blot analysis, Real-Time PCR, Ribonuclease protection assays. The following cell types are provided for illustrative purposes, but other cell types can be routinely used, provided that the target is expressed in the cell type chosen.

Cells are cultured in the appropriate medium as described below and maintained at 37° C. at 95-98% humidity and 5% $CO_2$. Cells are routinely passaged 2-3 times weekly.

BNCL-2: Mouse liver cell line BNCL-2 was purchased from ATCC and cultured in DMEM (Sigma) with 10% FBS+Glutamax i+non-essential amino acids+gentamicin.

Hepa1-6: Mouse liver cell line Hepa1-6 was purchased from ATCC and cultured in DMEM (Sigma) with 10% FBS+Glutamax i+non-essential amino acids+gentamicin.

HepG2: Human liver cell line HepG2 was purchased from ATCC and cultured in Eagle MEM (Sigma) with 10% FBS+Glutamax i+non-essential amino acids+gentamicin.

Example 15

Treatment with sisiRNA Therapeutics

The following examples are used for illustration of how sisiRNA complexes can be used in down-regulation of a therapeutic target. In general, the use of sisRNAs can be used using similar procedures as used for siRNA or antisense oligonucleotides. However, it is preferred that the RNA complexes are either cholesterol complexed and/or formulated with chitosan as described previously. Typically between 3 and 5× dosage of sisiRNA (or siRNA) is required as compared to an antisense oligonucleotide.

For example see the detailed protocols disclosed in:
Bcl2: WO2005/061710
Survivin: WO2006/050732
Hif1-alpha: WO2006/050734
P21-ras: PCT/DK2006/000512.
Apo-B: PCT/DK2006/000481

Numerous siRNA therapeutic designs are known in the prior art. The present analysis tests these in the form of sisiRNA, such as sisiLNA therapeutics. Suitably, sisiRNAs targeting ApoB are used.

Example 16

Treatment with Antisense Oligonucleotide

BNCL-2 or Hepa1-6 cells are seeded in 12-well plates at 37° C. (5% $CO_2$) in growth media supplemented with 10%

FBS, Glutamax I and Gentamicin. When the cells are 60-70% confluent, they are transfected in duplicates with different concentrations of oligonucleotides (0.04-25 nM) using Lipofectamine 2000 (5 µg/mL). Transfections are carried out essentially as described by Dean et al. (1994, JBC 269: 16416-16424). In short, cells are incubated for 10 min. with Lipofectamine in OptiMEM followed by addition of oligonucleotide to a total volume of 0.5 mL transfection mix per well. After 4 hours, the transfection mix is removed, cells are washed and grown at 37° C. for approximately 20 hours (mRNA analysis and protein analysis in the appropriate growth medium. Cells were then harvested for protein and RNA analysis.

Example 17

Extraction of RNA and cDNA Synthesis

Total RNA Isolation

Total RNA is isolated using RNeasy mini kit (Qiagen). Cells are washed with PBS, and Cell Lysis Buffer (RTL, Qiagen) supplemented with 1% mercaptoethanol is added directly to the wells. After a few minutes, the samples are processed according to manufacturer's instructions.
First Strand Synthesis First strand synthesis is performed using either OmniScript Reverse Transcriptase kit or M-MLV Reverse transcriptase (essentially as described by manufacturer (Ambion)) according to the manufacturer's instructions (Qiagen). When using OmniScript Reverse Transcriptase 0.5 µg total RNA each sample, is adjusted to 12 µl and mixed with 0.2 µl poly $(dT)_{12-18}$ (0.5 µg/µl) (Life Technologies), 2 µl dNTP mix (5 mM each), 2 µl 10×RT buffer, 0.5 µl RNAguard™ RNase inhibitor (33 units/mL, Amersham) and 1 µl OmniScript Reverse Transcriptase followed by incubation at 37° C. for 60 min. and heat inactivation at 93° C. for 5 min. When first strand synthesis is performed using random decamers and M-MLV-Reverse Transcriptase (essentially as described by manufacturer (Ambion)) 0.25 µg total RNA of each sample was adjusted to 10.8 µl in $H_2O$. 2 µl decamers and 2 µl dNTP mix (2.5 mM each) is added. Samples were heated to 70° C. for 3 min. and cooled immediately in ice water and added 3.25 µl of a mix containing (2 µl 10×RT buffer; 1 µl M-MLV Reverse Transcriptase; 0.25 µl RNAase inhibitor). cDNA is synthesized at 42° C. for 60 min followed by heating inactivation step at 95° C. for 10 min and finally cooled to 4° C.

Example 18

Analysis of Oligonucleotide Inhibition of Apo-B100 Expression by Real-Time PCR

Antisense modulation of Apo-B100 expression can be assayed in a variety of ways known in the art. For example, Apo-B100 mRNA levels can be quantitated by, e.g., Northern blot analysis, competitive polymerase chain reaction (PCR), or real-time PCR. Real-time quantitative PCR is presently preferred. RNA analysis can be performed on total cellular RNA or mRNA.

Methods of RNA isolation and RNA analysis such as Northern blot analysis is routine in the art and is taught in, for example, Current Protocols in Molecular Biology, John Wiley and Sons. Real-time quantitative (PCR) can be conveniently accomplished using the commercially IQ Multi-Color Real Time PCR Detection System available from BioRAD. Real-time Quantitative PCR is a technique well known in the art and is taught in for example Heid et al. Real time quantitative PCR, Genome Research (1996), 6: 986-994.
Real-Time Quantitative PCR Analysis of Apo-B100 mRNA Levels To determine the relative mouse ApoB mRNA level in treated and untreated samples, the generated cDNA is used in quantitative PCR analysis using an iCycler from BioRad.

To 8 µl of 5-fold (Gapdh and Beta-actin) diluted cDNA is added 52 µl of a mix containing 29.5 µl Platinum qPCR Supermix-UDG (in-vitrogen), 1030 nM of each primer, 0.57×SYBR Green (Molecular probes) and 11.4 nM Fluorescein (Molecular probes).

Duplicates of 25 µl was is for Q-PCR: 50° C. for 120 sec., 95° C. for 120 sec. and 40 cycles [95° C. for 30 sec. and 60° C. for 60 sec.].

ApoB expression is quantified using a 50-fold diluted cDNA and a standard Q-PCR protocol. The primers (final conc of respectively forward and reverse primers 0.6 µM and 0.9 µM) and probe (final conc. 0.1 µM) are mixed with 2× Platinum Quantitative PCR SuperMix UDG (cat. # 11730, Invitrogen) and added to 3.3 µl cDNA to a final volume of 25 µl. Each sample is analysed in duplicates. PCR program: 50° C. for 2 minutes, 95° C. for 10 minutes followed by 40 cycles of 95° C., 15 seconds, 60° C., 1 minutes.

ApoB mRNA expression is normalized to mouse β-actin or Gapdh mRNA which is similarly quantified using Q-PCR.

```
Primers:
mGapdh:
                                    (SEQ ID NO: 73)
    5'-agcctcgtcccgtagacaaaat-3'
and (SEQ ID NO: 74)
    5'-gttgatggcaacaatctccactttt-3' mβ-actin:
                                    (SEQ ID NO: 75)
    5'-ccttccttcttgggtatggaa-3'
and (SEQ ID NO: 76)
    5'-gctcaggaggagcaatgatct-3' mApoB:
                                    (SEQ ID NO: 77)
    5'-gcccattgtggacaagttgatc-3'
and (SEQ ID NO: 78)
    5'-ccaggacttggaggtcttgga-3' mApoB Taqman probe:
                                    (SEQ ID NO: 79)
    5'-fam-aagccagggcctatctccgcatcc-3'
2-fold dilutions of cDNA synthesised from
untreated mouse Hepatocyte cell line (Hepa1-6
cells) (diluted 5 fold and expressing both ApoB
and β-actin or Gapdh) is used to prepare
standard curves for the assays. Relative quanti-
ties of ApoB mRNA were determined from the calcu-
lated Threshold cycle using the iCycler iQ Real
Time Detection System software.
```

Example 19

Western Blot Analysis of Apo-B100 Protein Levels

The in vitro effect of Apo-B100 oligos on Apo-B100 protein levels in transfected cells is determined by Western Blotting.

Cells are harvested and lysed in 50 mM Tris-HCl pH 6.8, 10% glycerol, 2.5% SDS, 5 mM DTT and 6 M urea supplemented with protease inhibitor cocktail (Roche). Total protein concentrations is measured using a BCA protein assay kit (Pierce). 50 μg total protein is run on 10-12% Bis-Tris gels in MOPS buffer or on 3-8% Tris Acetate gels and blotted onto a PVDF membranes according to manufacture's instructions (Invitrogen). After overnight incubation in blocking buffer (PBS-T supplemented with 5% low fat milk powder), the membranes are incubated overnight with primary antibody detecting ApoB-100. As control of loading, tubulin or actin is detected using monoclonal antibodies from Neomarker. Membranes are then incubated with secondary antibodies and ApoB-100 is visualized using a chromogenic immunodetection kit (Invitrogen) or a chemiluminescent ECL$^+$ detection kit (Amersham).

Example 20

Antisense Inhibition of Human Apo-B100 Expression Using Antisense Oligonucleotides In accordance with the present invention, a series of sisiRNA oligonucleotides are designed to target different regions of the human Apo-B100 sisiRNA. compounds are evaluated for their potential to knockdown Apo-B100 mRNA in mouse hepatocytes (Hepa1-6 cells) following lipid-assisted uptake and comparison of knockdown of ApoB-100 in BNLCL2 by sisiRNA complexes and in Hepa 1-6 cells.

Transcript steady state was monitored by Real-time PCR and normalised to the GAPDH transcript steady state. It appears from initial analysis that sisiRNA may be effective.

Example 20

In-Vivo Target Downregulation of LNA Containing Oligonucleotide Compounds

C57BL/6 mice (20 g) receive 50 mg/kg i.v. on three consecutive days (group size of 7 mice). sisiRNAs are dissolved in 0.9% saline (NaCl) and given at 10 mL/kg body weight (~0.2 ml per injection). At sacrifice the weight of the liver is recorded. Tissues for measurement of ApoB mRNA expression is stored in RNA later (Ambion) at −20° C. until use. mRNA analysis on Jejunum and Liver and total cholesterol in plasma is performed 24 h after last i.v. injection.

Example 21

Cholesterol Levels in Plasma

Total cholesterol level is measured in plasma using a colometric assay Cholesterol CP from ABX Pentra. The cholesterol is measured following enzymatic hydrolysis and oxidation. 21.5 μL water is added to 1.5 μL plasma. 250 μL reagent is added and within 5 min the cholesterol content is measured at a wavelength of 540 nM. Measurements on each animal is made in duplicates. The sensitivity and linearity is tested with 2 fold diluted control compound (ABX Pentra N control). The relative Cholesterol level is determined by subtraction of the background and presented relative to the cholesterol levels in plasma of saline treated mice.

Example 22

In-Vivo Target Down-Regulation of LNA Oligonucleotide Compounds

C57BL/6 mice (20 g) receive 25 or 50 mg/kg i.v. on three consecutive days (group size of 7 mice). The sisiRNA constructs are dissolved in 0.9% saline (NaCl) and given at 10 mL/kg body weight (~0.2 mL per injection). Tissues for measurement of ApoB mRNA expression is stored in for later (Ambion) at −20° C. until use. mRNA analysis on Jejunum and Liver, total- and LDL cholesterol in plasma is performed 24 h after last i.v. injection.

It appears that sisiRNA constructs targeted against ApoB may be effective at down regulation ApoB mRNA, ApoB protein and relative cholesterol levels.

Further examples are illustrated by FIGS. 19 to 27.

The invention claimed is:

1. An RNA complex, capable of mediating RNA interference, comprising a core substantially double-stranded region of between 18-23 base pairs, said core substantially double stranded region consisting of an antisense strand and a discontinuous passenger strand; wherein the discontinuous passenger strand is hybridized to the antisense strand, and; wherein the discontinuity in the passenger strand is a nick or a gap of 1 nucleotide, and; wherein the RNA complex comprises one or more LNA units, and; wherein the discontinuous passenger strand comprises at least a first and a second RNA-molecule, and; wherein the first RNA molecule of the discontinuous passenger strand is 8-13 nucleobases in length and the second molecule of the discontinuous passenger strand is 8-14 nucleobases in length, and; wherein first and second RNA molecules of the passenger strand each comprises at least one LNA unit.

2. The RNA complex according to claim 1, wherein first RNA molecule of the passenger strand comprises at least two LNA units.

3. The RNA complex according to claim 1, wherein second RNA molecule of the passenger strand comprises at least two LNA units.

4. The RNA complex according to claim 1, wherein the first and the second RNA molecule of the passenger strand each comprise at least two LNA units.

5. The RNA complex according to claim 1, wherein an LNA unit is located within the three 3' terminal nucleotides of the first and second RNA molecules of the passenger strand.

6. The RNA complex according to claim 1, wherein the antisense strand comprises at least one LNA unit within the duplex region formed with the discontinuous passenger strand.

7. The RNA complex according to claim 1, wherein at least one the LNA units present in the discontinuous passenger strand forms a base pair with a complementary LNA unit present in the antisense strand.

8. The RNA complex according to claim 1, wherein the antisense strand comprises a 3'-overhang of 1, 2 or 3 nucleotides.

9. The RNA complex according to claim 1, wherein the passenger strand comprises a 3'-overhang of 1, 2 or 3 nucleotides.

10. The RNA complex according to claim 1, wherein both the antisense strand and the passenger strand comprises a 3'-overhang of 1, 2 or 3 nucleotides.

* * * * *

UNITED STATES PATENT AND TRADEMARK OFFICE
CERTIFICATE OF CORRECTION

PATENT NO. : 8,329,888 B2  
APPLICATION NO. : 12/294126  
DATED : December 11, 2012  
INVENTOR(S) : Jesper Wengel et al.

Page 1 of 1

It is certified that error appears in the above-identified patent and that said Letters Patent is hereby corrected as shown below:

On the Title Page, 2nd col., Item (56) (Other Publications), line 30, delete "anatonmy" and insert -- anatomy --

In Column 58, line 50, claim 7, after "one" insert -- of --

Signed and Sealed this
Nineteenth Day of March, 2013

Teresa Stanek Rea
*Acting Director of the United States Patent and Trademark Office*